(12) United States Patent
Scheffler et al.

(10) Patent No.: US 11,990,208 B2
(45) Date of Patent: May 21, 2024

(54) METHODS FOR ACCURATE COMPUTATIONAL DECOMPOSITION OF DNA MIXTURES FROM CONTRIBUTORS OF UNKNOWN GENOTYPES

(71) Applicant: ILLUMINA, INC., San Diego, CA (US)

(72) Inventors: Konrad Scheffler, San Diego, CA (US); Johann Felix Wilhelm Schlesinger, San Diego, CA (US); Ryan Matthew Kelley, San Diego, CA (US)

(73) Assignee: Illumina, Inc., San Diego, CA (US)

(*) Notice: Subject to any disclaimer, the term of this patent is extended or adjusted under 35 U.S.C. 154(b) by 537 days.

(21) Appl. No.: 16/622,814

(22) PCT Filed: Jun. 19, 2018

(86) PCT No.: PCT/US2018/038222
§ 371 (c)(1),
(2) Date: Dec. 13, 2019

(87) PCT Pub. No.: WO2018/236827
PCT Pub. Date: Dec. 27, 2018

(65) Prior Publication Data
US 2022/0262460 A1 Aug. 18, 2022

Related U.S. Application Data

(60) Provisional application No. 62/522,618, filed on Jun. 20, 2017.

(51) Int. Cl.
*G16B 40/00* (2019.01)
(52) U.S. Cl.
CPC .................. *G16B 40/00* (2019.02)

(58) Field of Classification Search
None
See application file for complete search history.

(56) References Cited

U.S. PATENT DOCUMENTS

| 2004/0157243 A1 | 8/2004 | Huang et al. |
| 2010/0042438 A1* | 2/2010 | Moore ............... G16H 50/20 |
| | | 705/3 |

(Continued)

FOREIGN PATENT DOCUMENTS

| CN | 103374518 A | 10/2013 |
| EP | 3285193 A1 | 2/2018 |

(Continued)

OTHER PUBLICATIONS

Benschop, C. C. G.; Sijen, T. LoCIM-Tool: An Expert's Assistant for Inferring the Major Contributor's Alleles in Mixed Consensus DNA Profiles. Forensic Science International: Genetics 2014, 11, 154-165.*

(Continued)

*Primary Examiner* — Soren Harward
(74) *Attorney, Agent, or Firm* — Fletcher Yoder, P.C.

(57) ABSTRACT

Computer methods and systems for quantifying a nucleic acid sample comprising nucleic acid of one or more contributors to: receive nucleic acid sequence reads obtained from the nucleic acid sample and mapped to alleles at polymorphism loci; determine, using the nucleic acid sequence reads, allele counts for each of the alleles at the polymorphism loci; use a probabilistic mixture model that applies a probabilistic mixture model to the allele counts, and that uses probability distributions to model the allele counts at the polymorphism loci; quantify, using the probabilistic mixture model, one or more fractions of nucleic acid of the one or more contributors in the nucleic acid sample; determine a probability that a specific contributor among the one or more contributors has a specific genotype; and call, (Continued)

based on the posterior probability, that the nucleic acid sample includes nucleic acid from the specific contributor.

22 Claims, 18 Drawing Sheets

(56) References Cited

U.S. PATENT DOCUMENTS

| | | |
|---|---|---|
| 2012/0264121 A1 | 10/2012 | Rava et al. |
| 2013/0059733 A1 | 3/2013 | Lo et al. |
| 2013/0196862 A1 | 8/2013 | Rabinowitz et al. |
| 2015/0051087 A1 | 2/2015 | Rabinowitz et al. |
| 2016/0194703 A1 | 7/2016 | Rava et al. |

FOREIGN PATENT DOCUMENTS

| | | |
|---|---|---|
| JP | 2006519977 A | 8/2006 |
| JP | 2016184429 A | 10/2016 |
| WO | 2007062164 A2 | 5/2007 |
| WO | 2013/130848 A1 | 9/2013 |
| WO | 2014/014498 | 1/2014 |
| WO | 2016/167408 A1 | 10/2016 |
| WO | 2018/236827 A1 | 12/2018 |
| WO | 2018/236911 A1 | 12/2018 |

OTHER PUBLICATIONS

Bleka, Ø.; Storvik, G.; Gill, P. EuroForMix: An Open Source Software Based on a Continuous Model to Evaluate STR DNA Profiles from a Mixture of Contributors with Artefacts. Forensic Science International: Genetics 2016, 21, 35-44.*
Cowell, R. Combining Allele Frequency Uncertainty and Population Substructure Corrections in Forensic DNA Calculations. Forensic Science International: Genetics 2016, 23, 210-216.*
Graversen, T.; Lauritzen, S. Estimation of Parameters in DNA Mixture Analysis. Journal of Applied Statistics 2013, 40 (11), 2423-2436.*
Graversen, T.; Lauritzen, S. Computational Aspects of DNA Mixture Analysis: Exact Inference Using Auxiliary Variables in a Bayesian Network. Statistics and Computing 2015, 25 (3), 527-541.*
Hoogenboom, J.; van der Gaag, K. J.; de Leeuw, R. H.; Sijen, T.; de Knijff, P.; Laros, J. F. J. FDSTools: A Software Package for Analysis of Massively Parallel Sequencing Data with the Ability to Recognise and Correct STR Stutter and Other PCR or Sequencing Noise. Forensic Science International: Genetics 2017, 27, 27-40.*
Bornman, D.; Hester, M.; Schuetter, J.; Kasoji, M.; Minard-Smith, A.; Barden, C.; Nelson, S.; Godbold, G.; Baker, C.; Yang, B.; Walther, J.; Tornes, I.; Yan, P.; Rodriguez, B.; Bundschuh, R.; Dickens, M.; Young, B.; Faith, S. Short-Read, High-Throughput Sequencing Technology for STR Genotyping. BioTechniques 2012.*
Butler, J. Reported STR Alleles. In Forensic DNA Typing: Biology, Technology, and Genetics of STR Markers; Academic Press, 2005; pp. 561-576.*
Highnam, G.; Franck, C.; Martin, A.; Stephens, C.; Puthige, A.; Mittelman, D. Accurate Human Microsatellite Genotypes from High-Throughput Resequencing Data Using Informed Error Profiles. Nucleic Acids Research 2013, 41 (1), e32:1-7.*
Greenfield, P.; Roehm, U. Answering Biological Questions by Querying K-mer Databases. Concurrency and Computation: Practice and Experience 2013, 25 (4), 497-509.*
Li, H.; Homer, N. A Survey of Sequence Alignment Algorithms for Next-Generation Sequencing. Briefings in Bioinformatics 2010, 11(5), 473-483.*
Morin, P. Hash Tables. Chapter 1 of Handbook of Data Structures and Applications; Mehta, D. P., Sahni, S., Eds.; Chapman and Hall/CRC, 2005. pp. 9-1-9-19.*

Xin, H.; Lee, D.; Hormozdiari, F.; Yedkar, S.; Mutlu, O.; Alkan, C. Accelerating Read Mapping with FastHASH. BMC Genomics 2013, 14 (S1), S13:1-13.*
Anvar, S. Y., et al. TSSV: A Tool for Characterization of Complex Allelic Variants in Pure and Mixed Genomes. Bioinformatics 2014, 30 (12), 1651-1659.*
Kockan, C.; Hach, F.; Sarrafi, I.; Bell, R. H.; McConeghy, B.; Beja, K.; Haegert, A.; Wyatt, A. W.; Volik, S. V.; Chi, K. N.; Collins, C. C.; Sahinalp, S. C. SiNVICT: Ultra-Sensitive Detection of Single Nucleotide Variants and Indels in Circulating Tumour DNA. Bioinformatics 2017, 33 (1), 26-34.*
Jiang, P., et al., "FetalQuant: deducing fractional fetal DNA concentration from massively parallel sequencing of DNA in maternal plasma", Bioinformatics, vol. 28, No. 22, 2012, 2883-2890.
Kim, S., et al., "Estimation of allele frequency and association mapping using next-generation sequencing data", BMC Bioinformatics vol. 12 (1), Jun. 11, 2011, 231.
Nielsen, R., et al., "Genotype and SNP calling from next-generation sequencing data", Nat. Rev. Genet., Jun. 1, 2011, 443-451.
Cowell, R. G., et al.,; "Analysis of forensic DNA mixtures with artefacts," Journal of the Royal Statistical Society, Applied Statistics, Series C, 64, Part 1, Jan. 1, 2015, pp. 1-48.
PCT/US2018/038222, "International Search Report", dated Sep. 26, 2019.
Auchincloss, Jr., H.; "Xenogeneic transplatation. A review.," Transplantiation, 45(1), Jul. 1988, pp. 1-20. doi: 10.1097/00007890-198807000-00001. PMID: 3293272.
Makov, U. E.; "Mixture Models in Statistics," International Encyclopedia of the Social and Behavioral Sciences, vol. 15, Jan. 1, 2001, pp. 9910-9915. DOI: 10.1016/B0-08-043076-7/00464-2.
Li et al.; "Mapping short DNA sequencing reads and calling variants using mapping quality scores," Genome Res., 18 (11), Nov. 2008, pp. 1851-1858.
Shendure, J., et al.; "Next-generation DNA sequencing," Nat. Biotechnol 26, 2008, pp. 1135-1145. https://doi.org/10.1038/nbt1486.
Shalizi, C. S.; "Chapter 20: Mixture Models," Carnegie Mellon University, Lecture Notes, Apr. 5, 2011. Retrieved from the Internet: URL:https://www.stat.cmu.edu/~cshalizi/uADA/12/lectures/ch20.pdf [retrieved on Jan. 21, 2020].
Melsted, P., et al.; "Efficient counting of k-mers in DNA sequences using a bloom filter," BMC Bioinformatics, 12, 333, 2011. https://doi.org/10.1186/1471-2105-12-333.
Jun, G., et al.; "Detecting and estimating contamination of human DNA samples in sequencing and array-based genotype data," AM J Hum Genet., 91(5), Nov. 2, 2012, pp. 839-848. doi: 10.1016/j.ajhg.2012.09.004. Epub Oct. 25, 2012.
Bansal, V, et al.; "Fast individual ancestry inference from DNA sequence data leveraging allele frequencies for multiple populations," BMC Bioinformatics 16, 4, (2015). https://doi.org/10.1186/s12859-014-0418-7.
Heitzer, Ellen, et al.; "Circulating Tumor DNA as a Liquid Biopsy for Cancer," Clinical Chemistry, vol. 61, Iss. 1, Jan. 1, 2015, pp. 112-123.
Yuan, Shuai, et al.; "One size doesn't fit all—RefEditor: Building personalized diploid reference genome to improve read mapping and genotype calling in next generation sequencing studies," PLOS Computational Biology, 2015, pp. 1-20.
Shajii, Ariya, et al.; "Fast genotyping of known SNPs through approximate k-mer matching," Bioinformatics 32, 2016, pp. 538-544.
Cheng, F., et al., "Circulating tumor DNA: a promising biomarker in the liquid biopsy of cancer", Oncotarget, Jul. 26, 2016; 7(30): 48832-48841; (Year:2016).
Takai E., et al., "Circulating tumor DNA as a liquid biopsy target for detection pancreatic cancer", World J Gastroenterology, Oct. 14, 2016; 22(38); 8480-8488; (Year:2016).
Anvar, S. Y., et al.; "TSSV: A Tool for Characterization of Complex Allelic Variants in Pure and Mixed Genomes," Bioinformatics, 30(12), 2014, pp. 1651-1659.

(56) References Cited

OTHER PUBLICATIONS

Benschop, C. C. G., et al.; "LoCIM-Tool: An Expert's Assistant for Inferring the Major Contributor's Alleles in Mixed Consensus DNA Profiles," Forensic Science International: Genetics, 11, 2014, pp. 154-165.

Bleka, Ø, et al.; "EuroForMix: An Open Source Software Based on a Continuous Model to Evaluate STR DNA Profiles from a Mixture of Contributors with Artefacts," Forensic Science International: Genetics, 21, 2016, pp. 35-44.

Bornman, D., et al.; "Short Read, High-Throughput Sequencing Technology for STR Genotyping," BioTechniques, 2012.

Graversen, T., et al.; "Estimation of Parameters in DNA Mixture Analysis," Journal of Applied Statistics, 40(11), 2013, pp. 2423-2436.

Graversen, T., et al.; "Computational Aspects of DNA Mixture Analysis: Exact Inference Using Auxiliary Variables in a Bayesain Network," Statistics and Computing, 25(3), 2015, pp. 527-541.

Greenfield, P., et al.; "Answering Biological Questions by Querying K-mer Databases," Concurrency and Computation: Practice and Experience, 25(4), 2013, pp. 497-509.

Highnam, G., et al.; "Accurate Human Microsatellite Genotypes from High-Throughput Resequencing Data Using Informed Error Profiles," Nucleic Acids Research, 41(1), 2013, e32, pp. 1-7.

Hoogenboom, J., et al.; "FDSTools: A Software Package for Analysis of Massively Parallel Sequencing Data with the Ability to Recognize and Correct STR Stutter and Other PCR or Sequencing Noise," Forensic Science International: Genetics, 27, 2017, pp. 27-40.

Kockan, C., et al.; "SiNVICT: Ultra-Sensitive Detection of Single Nucleotide Variants and Indels in Circulating Tumour DNA," Bioinformatics, 33(1), 2017, pp. 26-34.

Li, H., et al.; "A survey of Sequence Alignment Algorithms for Next-Generation Sequencing," Briefing in Bioinformatics, 11(5), 2010, pp. 473-483.

Xin, H., et al.; "Accelerating Read Mapping with FastHASH," BMC Genomics, 14 (S1), 2013, S13, pp. 1-13.

\* cited by examiner

METHODS FOR ACCURATE COMPUTATIONAL DECOMPOSITION OF DNA MIXTURES FROM CONTRIBUTORS OF UNKNOWN GENOTYPES

CROSS-REFERENCE TO RELATED APPLICATIONS

This application is a National Stage Application claiming the priority of PCT Application No. PCT/US2018/038222, filed on Jun. 19, 2018, which claims priority to U.S. Provisional Patent Application No. 62/522,618, filed on Jun. 20, 2017, which are hereby incorporated by reference herein in their entireties.

BACKGROUND

Sequencing data from a nucleic acid (e.g., DNA or RNA) mixture of closely related genomes is frequently found in research as well as clinical settings, and quantifying the mixing contributors has been a challenge when the original genomes are unknown. For example, in the context of microbiology and metagenomics, researchers and clinicians may need to quantify closely related bacterial strains of the same species in an environmental sample. In the setting of forensics, law enforcement personnel may need to quantify as well as identify human individuals from a blood sample containing DNA of multiple individuals.

Another application is Next Generation Sequencing (NGS) coupled liquid biopsy. NGS-coupled liquid biopsy is an emerging diagnosis strategy with potential applications in various clinical settings. In the context of organ or tissue transplant, NGS-coupled liquid biopsy provides a non-invasive approach for monitoring the health of allogeneic graft by quantifying the amount of allogeneic DNA in recipient blood. In some applications, the donor and recipient genomes are unknown or partially unknown.

SUMMARY

Some implementations presented herein provide computer-implemented methods and systems for deconvolution of nucleic acid mixture samples including nucleic acid of two or more contributors of unknown genotypes. One aspect of the disclosure relates to methods for quantifying nucleic acid fractions in nucleic acid samples including nucleic acid (e.g., DNA or RNA) of two or more contributors having different genomes. In some implementations, the nucleic acid mixture samples include biological tissues, cells, peripheral blood, saliva, urine, and other biological fluid, as described below. In some applications, the nucleic acid sample includes the nucleic acid of only a single contributor, and the implementations described herein can determine that the single contributor's nucleic acid accounts for 100% of the nucleic acid in the sample. So although the description hereinafter refers to the nucleic acid sample as a nucleic acid mixture sample in some implementations, it is understood that the sample can include a single contributor's nucleic acid, with the contributor's fraction being 100% or 1. Of course, the methods can also be used to quantify a sample including nucleic acid of two or more contributors.

Because various methods and systems provided herein implement algorithms and processes that use probabilistic mixture models and Bayesian inference techniques, the embodiments provide technological improvements over conventional methods in deconvolution of nucleic acid (e.g., DNA or RNA) mixture samples. Some implementations described herein refer to a DNA sample, but it is understood that the implementations are also applicable to analyzing RNA samples. Some implementations provide improved analytical sensitivity and specificity, providing more accurate deconvolution and quantification of nucleic acid mixture samples. Some implementations allow accurate analysis of nucleic acid mixture samples with nucleic acid quantities that are too low to allow accurate quantification of contributor fractions or determination of contributor genotype.

In some embodiments, the method is implemented at a computer system that includes one or more processors and system memory configured to deconvolve a nucleic acid mixture sample including nucleic acid of two or more contributors.

Some embodiments provide a method for quantifying a fraction of nucleic acid of a contributor in a nucleic acid mixture sample comprising nucleic acid of the contributor and at least one other contributor. The method involves: (a) receiving, by the computer system, nucleic acid sequence reads obtained from the nucleic acid sample and mapped to one or more alleles at one or more polymorphism loci; (b) determining, using the nucleic acid sequence reads and by the one or more processors, allele counts for each of the one or more alleles at the one or more polymorphism loci; (c) using a probabilistic mixture model that applies a probabilistic mixture model to the allele counts, and that uses probability distributions to model the allele counts at the one or more polymorphism loci, the probability distributions accounting for errors in the nucleic acid sequence reads; (d) quantifying, using the probabilistic mixture model and by the one or more processors, one or more fractions of nucleic acid of the one or more contributors in the nucleic acid sample; (e) determining a probability that a specific contributor among the one or more contributors has a specific genotype; and (f) calling, based on the posterior probability, that the nucleic acid sample includes nucleic acid from the specific contributor.

In some implementations, the one or more contributors include two or more contributors.

In some implementations, the method further includes determining a total number of contributors in the one or more contributors.

In some implementations, one or more genotypes of the one or more contributors were unknown. In some implementations, the method further includes determining one or more allele configurations at each of the one or more polymorphism loci, each allele configuration including allele status of two or more alleles for each of the one or more contributors. In some implementations, the method further includes determining estimated probabilities for the one or more allele configurations.

In some implementations, obtaining the posterior probability that a specific contributor among the one or more contributors has a specific genotype includes: (i) multiplying prior probabilities of genotype configurations by likelihoods of the genotype configurations; (ii) normalizing a product of (i) by a sum over genotype space; and (iii) summing over genotype configurations containing the specific genotype to obtain the posterior probability.

In some implementations, the specific genotype includes a multiple-locus genotype, the method further including: summing, over all contributors, a posterior probability that a contributor has the specific genotype at all loci; and determining, based on the summed probability, the specified multiple-locus genotype appears in any contributor. In some implementations, the nucleic acid sample is a forensic sample and the data of the multiple-locus genotype is obtained from a person of interest, the method further including determining that the person of interest is a contributor of the nucleic acid sample.

In some implementations, the nucleic acid sample includes DNA molecules and/or RNA molecules. In some implementations, wherein the nucleic acid sequence reads were obtained by sequencing the DNA molecules and/or RNA molecules using unique molecular indices.

In some implementations, the probability distributions include a first binomial distribution. In some implementations, the first binomial distribution is expressed as follows:

$$n_{ij} \sim BN(n_i, p_{ij})$$

$n_{ij}$ is an allele count for allele j at locus i; $n_i$ is a total allele count at locus i; and $p_{ij}$ is a probability parameter indicating the probability of allele j at locus i.

In some implementations, the probability parameter $p_{ij}$ is a function of: (i) a fraction of nucleic acid of one of the one or more contributors in the nucleic acid sample, or β; (ii) genotypes of the one or more contributors, or G; and/or (iii) errors in the nucleic acid sequence reads, or θ.

In some implementations, the probabilistic mixture model uses a beta distribution to model the errors in the nucleic acid sequence reads. In some implementations, the beta distribution is defined by a mean parameter, μ, and a concentration parameter, k. In some implementations, the concentration parameter has a prior representing different noise conditions, and the concentration parameter varies across loci.

In some implementations, (c) includes combining the first binomial distribution and the beta distribution to obtain a marginal distribution of $n_{ij}$ that follows a beta-binomial distribution. In some implementations, the beta-binomial distribution has the form:

$$BB(n_{ij}|n_i,\mu,k).$$

In some implementations, (c) includes quantifying the one or more fractions of nucleic acid of the one or more contributors in the nucleic acid sample by maximizing a likelihood function of the nucleic acid sequence reads. In some implementations, (c) includes: calculating a plurality of likelihood values using a plurality of potential fraction values and a likelihood function of the allele counts determined in (b) identifying a potential fraction vector associated with a maximum likelihood value; and quantifying the one or more fractions of nucleic acid of the one or more contributors in the nucleic acid sample using the identified potential fraction vector.

In some implementations, the likelihood function depends on P(G|π), which is a prior probability of the genotype of the one or more contributors given a population allele frequency (π). In some implementations, the prior probability P(G|π) is calculated using marginal distributions that satisfy the Hardy-Weinberg equilibrium. In some implementations, the prior probability is calculated considering a dummy allele with a fixed prior probability representing mechanistic dropout. In some implementations, the probabilistic mixture model uses a second binomial distribution to model stutter errors in the allele data. In some implementations, the second binomial distribution is expressed as follows:

$$s_{ik} \sim BN(n_{i(k+1)}, r_i)$$

$s_{ik}$ is a stutter allele count at locus i of a stutter allele that appears to be allele k but actually results from a stutter error of allele k+1; $n_{i(k+1)}$ is an original allele count of allele k+1 at locus i; and $r_i$ is a stutter rate for locus i.

In some implementations, the stutter rate r varies across loci and has a prior representing different noise conditions, the prior being shared across loci. In some implementations, (d) includes quantifying fractions of nucleic acid of the one or more contributors in the nucleic acid sample using a likelihood function including a product of likelihoods of non-stutter allele counts and likelihoods of stutter allele counts. In some implementations, (c) includes adding a fixed number of molecules to an allele count assigned to allele k+1 when determining a number of molecules from which stutter can potentially originate.

In some implementations, the probabilistic mixture model uses a dummy out-of-sample allele to model natural dropout. In some implementations, the prior of the dummy out-of-sample allele is proportional to a number of unobserved alleles. In some implementations, the number of unobserved alleles is estimated by: interpolating all integers between the shortest and longest observed integer-valued alleles, adding any observed non-integer-valued alleles, and returning the maximum of the resulting value and a threshold value.

In some implementations, (c) includes pruning genotype configurations from data used to quantify the fractions of nucleic acid of the one or more contributors in the nucleic acid sample. In some implementations, pruning genotype configurations includes: limiting genotype configurations that are plausible by constructing a list of required alleles and excluding loci with not enough contributors to explain all required alleles. In some implementations, the list of required alleles consists essentially of alleles having allele counts above a threshold and too high to be plausible due to stutter drop-in. In some implementations, the threshold is a sum of (i) a maximum non-stutter allele count, and (ii) a value multiplied by a count of potential stutter donor alleles. In some implementations, pruning genotype configurations includes: removing genotype configurations that have poor matches between the allele data and expected allele counts. In some implementations, the genotype configurations that have poor matches have root mean squared error (RMSE) values larger than one or more thresholds.

In some implementations, the alleles at the one or more polymorphism loci include single nucleotide polymorphism (SNP) alleles and/or short tandem repeat (STR) alleles.

The disclosed embodiments also provide a computer program product including a non-transitory computer readable medium on which is provided program instructions for performing the recited operations and other computational operations described herein.

Some embodiments provide a system for quantifying a fraction of nucleic acid of a contributor in a nucleic acid mixture sample comprising nucleic acid of the contributor and at least one other contributor. The system includes a sequencer for receiving nucleic acids from the test sample providing nucleic acid sequence information from the sample, a processor; and one or more computer-readable storage media having stored thereon instructions for execution on the processor using the method recited herein.

One aspect of the disclosure provides a computer system including system memory and one or more processors. The processors are configured to: (a) receive nucleic acid sequence reads obtained from the nucleic acid sample and mapped to one or more alleles at one or more polymorphism loci; (b) determine, using the nucleic acid sequence reads, allele counts for each of the one or more alleles at the one or more polymorphism loci; and (c) using a probabilistic mixture model that applies a probabilistic mixture model to the allele counts, and that uses probability distributions to model the allele counts at the one or more polymorphism loci, the probability distributions accounting for errors in the nucleic acid sequence reads; (d) quantify, using the probabilistic mixture model, one or more fractions of nucleic acid of the one or more contributors in the nucleic acid sample; (e) determining a posterior probability that a specific contributor among the one or more contributors has a specific genotype; and (f) calling, based on the posterior probability, that the nucleic acid sample includes nucleic acid from the specific contributor.

In some implementations, the system further includes a tool for extracting nucleic acid from the nucleic acid sample.

In some implementations, the one or more processors are further configured to determine a total number of contributors in the one or more contributors.

In some implementations, the one or more processors are further configured to determine an allele configuration at each of the one or more polymorphism loci, the allele configuration including allele status of two or more alleles for each of the one or more contributors.

Another aspect of the disclosure provides a non-transitory computer-readable medium storing program code that, when executed by one or more processors of a computer system, causes the computer system to implement a method of quantifying a nucleic acid sample including nucleic acid of one or more contributors, said program code including: (a) code for receiving nucleic acid sequence reads obtained from the nucleic acid sample and mapped to one or more alleles at one or more polymorphism loci; (b) code for determining, using the nucleic acid sequence reads, allele counts for each of the one or more alleles at the one or more polymorphism loci; (c) code for using a probabilistic mixture model that applies a probabilistic mixture model to the allele counts, and that uses probability distributions to model the allele counts at the one or more polymorphism loci, the probability distributions accounting for errors in the nucleic acid sequence reads; (d) code for quantifying, using the probabilistic mixture model, one or more fractions of nucleic acid of the one or more contributors in the nucleic acid sample; (e) code for determining a posterior probability that a specific contributor among the one or more contributors has a specific genotype; and (f) code for calling, based on the posterior probability, that the nucleic acid sample includes nucleic acid from the specific contributor.

Although the examples herein concern humans and the language is primarily directed to human concerns, the concepts described herein are applicable to genomes from any plant or animal. These and other objects and features of the present disclosure will become more fully apparent from the following description and appended claims, or may be learned by the practice of the disclosure as set forth hereinafter.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

DETAILED DESCRIPTION

Definitions

Figure 1:
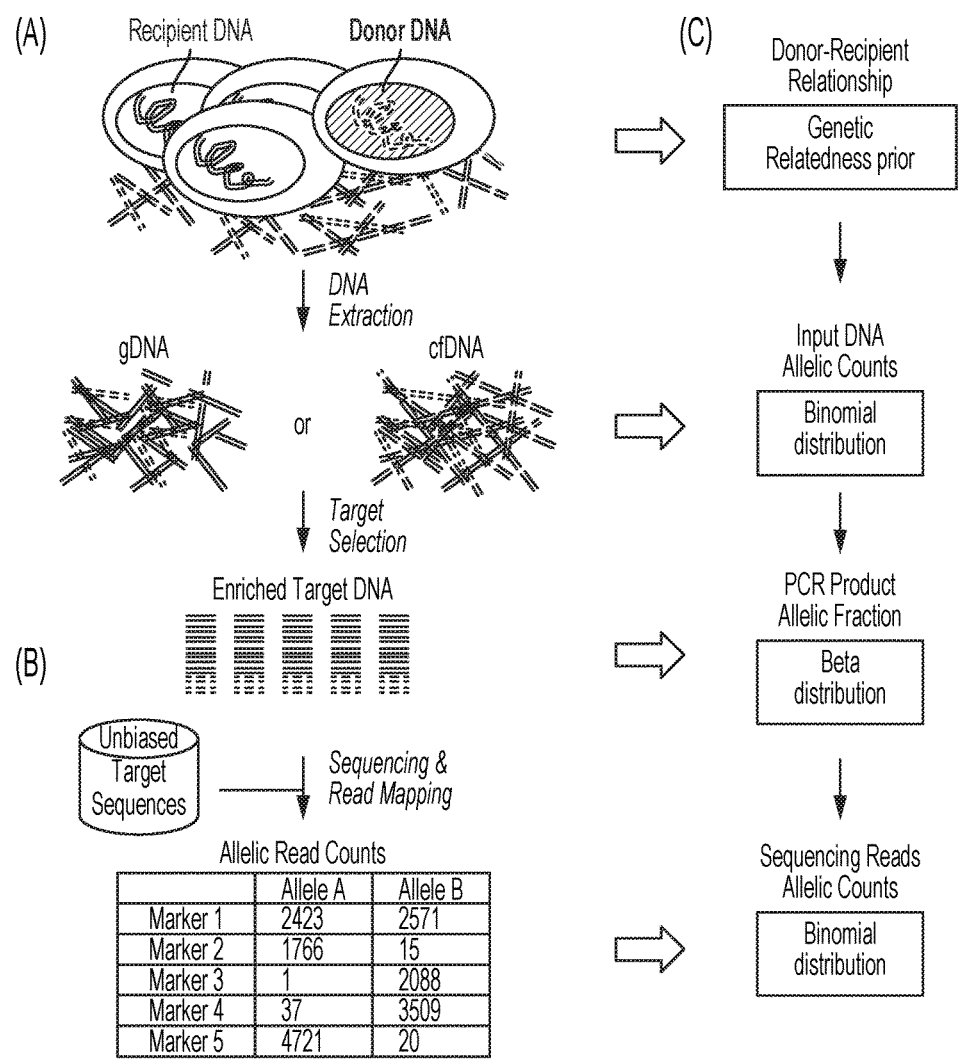
FIGS. 1A-1C show an overview of bioinformatics algorithm and statistical model designed for contributor DNA quantification.

Unless otherwise indicated, the practice of the method and system disclosed herein involves conventional techniques and apparatus commonly used in molecular biology, microbiology, protein purification, protein engineering, protein and DNA sequencing, and recombinant DNA fields, which are within the skill of the art. Such techniques and apparatus are known to those of skill in the art and are described in numerous texts and reference works (See e.g., Sambrook et al., "Molecular Cloning: A Laboratory Manual," Third Edition (Cold Spring Harbor), [2001]); and Ausubel et al., "Current Protocols in Molecular Biology" [1987]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art. As used herein, the singular terms "a," "an," and "the" include the plural reference unless the context clearly indicates otherwise.

Unless otherwise indicated, nucleic acids are written left to right in 5' to 3' orientation and amino acid sequences are written left to right in amino to carboxy orientation, respectively.

The term donor DNA (dDNA) refers to DNA molecules originating from cells of a donor of a transplant. In various implementations, the dDNA is found in a sample obtained from a donee who received a transplanted tissue/organ from the donor. In some implementations, the dDNA include Circulating cell-free DNA or simply cell-free DNA (cfDNA) are DNA fragments that are not confined within cells and are freely circulating in the bloodstream or other bodily fluids. It is known that cfDNA have different origins, in some cases originating from tumor cells or tumor affected cells, in other cases originating from fetal cells of a fetus carried by a pregnant mother and circulating in maternal blood. In general, cfDNA are fragmented and include only a small portion of a genome, which genome may be different from the genome of the organism from which the cfDNA is obtained.

The term non-circulating genomic DNA (gDNA) or cellular DNA are used to refer to DNA molecules that are confined in cells and often include a complete genome.

A beta distribution is a family of continuous probability distributions defined on the interval [0, 1] parametrized by two positive shape parameters, denoted by, e.g., $\alpha$ and $\beta$, that appear as exponents of the random variable and control the shape of the distribution. The beta distribution has been applied to model the behavior of random variables limited to intervals of finite length in a wide variety of disciplines. In Bayesian inference, the beta distribution is the conjugate prior probability distribution for the Bernoulli, binomial, negative binomial and geometric distributions. For example, the beta distribution can be used in Bayesian analysis to describe initial knowledge concerning probability of success. If the random variable X follows the beta distribution, the random variable X is written as X~Beta($\alpha$, $\beta$).

A binomial distribution is a discrete probability distribution of the number of successes in a sequence of n independent experiments, each asking a yes-no question, and each with its own boolean-valued outcome: a random variable containing single bit of information: positive (with probability p) or negative (with probability q=1−p). For a single trial, i.e., n=1, the binomial distribution is a Bernoulli distribution. The binomial distribution is frequently used to model the number of successes in a sample of size n drawn with replacement from a population of size N. If the random variable X follows the binomial distribution with parameters n$\in \mathbb{N}$ and p$\in$[0,1], the random variable X is written as X~B(n,p).

Poisson distribution, denoted as Pois( ) herein, is a discrete probability distribution that expresses the probability of a given number of events occurring in a fixed interval of time and/or space if these events occur with a known average rate and independently of the time since the last event. The Poisson distribution can also be used for the number of events in other specified intervals such as distance, area or volume. The probability of observing k events in an interval according to a Poisson distribution is given by the equation:

$$P(k \text{ events in interval}) = \frac{\lambda^k e^{-\lambda}}{k!}$$

where $\lambda$ is the average number of events in an interval or an event rate, also called the rate parameter e is 2.71828, Euler's number, or the base of the natural logarithms, k takes values 0, 1, 2, . . . , and k! is the factorial of k.

Gamma distribution is a two-parameter family of continuous probability distributions. There are three different parametrizations in common use: with a shape parameter k and a scale parameter $\theta$; with a shape parameter $\alpha$=k and an inverse scale parameter $\beta$=1/$\theta$, called a rate parameter; or with a shape parameter k and a mean parameter $\mu$=k/$\beta$. In each of these three forms, both parameters are positive real numbers. The gamma distribution is the maximum entropy probability distribution for a random variable X for which E[X]=k$\theta$=$\alpha$/$\beta$ is fixed and greater than zero, and E[ln(X)]=$\psi$(k)+ln($\theta$)=$\psi$($\alpha$)−ln($\beta$) is fixed ($\psi$ is the digamma function).

Polymorphism and genetic polymorphism are used interchangeably herein to refer to the occurrence in the same population of two or more alleles at one genomic locus, each with appreciable frequency.

Polymorphism site and polymorphic site are used interchangeably herein to refer to a locus on a genome at which two or more alleles reside.

Allele frequency or gene frequency is the frequency of an allele of a gene (or a variant of the gene) relative to other alleles of the gene, which can be expressed as a fraction or percentage. An allele frequency is often associated with a particular genomic locus, because a gene is often located at with one or more locus. However, an allele frequency as used herein can also be associated with a size-based bin of DNA fragments. In this sense, DNA fragments such as cfDNA containing an allele are assigned to different size-based bins. The frequency of the allele in a size-based bin relative to the frequency of other alleles is an allele frequency.

The term "parameter" herein refers to a numerical value that characterizes a property of a system such as a physical feature whose value or other characteristic has an impact on a relevant condition such as a sample or DNA molecules. In some cases, the term parameter is used with reference to a variable that affects the output of a mathematical relation or model, which variable may be an independent variable (i.e., an input to the model) or an intermediate variable based on one or more independent variables. Depending on the scope of a model, an output of one model may become an input of another model, thereby becoming a parameter to the other model.

The term "plurality" refers to more than one element.

The term "paired end reads" refers to reads from paired end sequencing that obtains one read from each end of a nucleic acid fragment. Paired end sequencing may involve fragmenting strands of polynucleotides into short sequences called inserts. Fragmentation is optional or unnecessary for relatively short polynucleotides such as cell free DNA molecules.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cfDNA or cellular DNA molecules. The term "polynucleotide" includes, without limitation, single- and double-stranded polynucleotide.

The term "test sample" herein refers to a sample typically derived from a biological fluid, cell, tissue, organ, or organism, comprising a nucleic acid or a mixture of nucleic acids. Such samples include, but are not limited to sputum/oral fluid, amniotic fluid, blood, a blood fraction, or fine needle biopsy samples (e.g., surgical biopsy, fine needle biopsy, etc.), urine, peritoneal fluid, pleural fluid, and the like. Although the sample is often taken from a human subject (e.g., patient), the assays can be used in samples from any mammal, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "read" refers to a sequence obtained from a portion of a nucleic acid sample. Typically, though not necessarily, a read represents a short sequence of contiguous base pairs in the sample. The read may be represented symbolically by the base pair sequence (in A, T, C, or G) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

The term "genomic read" is used in reference to a read of any segments in the entire genome of an individual.

As used herein, the terms "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

Aligned reads or tags are one or more sequences that are identified as a match in terms of the order of their nucleic acid molecules to a known sequence from a reference genome. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. Patent Application No. 61/552,374 filed Oct. 27, 2011 which is incorporated herein by reference in its entirety. The matching of a sequence read in aligning can be a 100% sequence match or less than 100% (non-perfect match).

The term "mapping" used herein refers to specifically assigning a sequence read to a larger sequence, e.g., a reference genome, a subsequence of the larger sequence using alignment or membership assignment.

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. In some embodiments, a reference Y chromosome is the Y chromosome sequence from human genome version hg19. Such sequences may be referred to as chromosome reference sequences. Other examples of reference sequences include genomes of other species, as well as chromosomes, sub-chromosomal regions (such as strands), etc., of any species.

In various embodiments, the reference sequence is a consensus sequence or other combination derived from multiple individuals. However, in certain applications, the reference sequence may be taken from a particular individual.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids, e.g., cfDNA, were naturally released by cells through naturally occurring processes such as necrosis or apoptosis. In another embodiment, a mixture of nucleic acids that is derived from two different genomes means that the nucleic acids were extracted from two different types of cells from a subject. For instance, a mixture of nucleic acids includes nucleic acids originating from donor cells and donee cells obtained from an organ transplant subject. In some implementations, a mixture of nucleic acids comprise biological materials of two or more contributor individuals. For example, a forensic sample including biological materials of two or more individuals includes DNA of the two or more individuals.

The term "based on" when used in the context of obtaining a specific quantitative value, herein refers to using another quantity as input to calculate the specific quantitative value as an output.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

As used herein, the term "corresponding to" sometimes refers to a nucleic acid sequence, e.g., a gene or a chromosome, that is present in the genome of different subjects, and which does not necessarily have the same sequence in all genomes, but serves to provide the identity rather than the genetic information of a sequence of interest, e.g., a gene or chromosome.

The term "contributor" herein refers to a human contributor as well as a non-human contributor such as a mammal, an invertebrate, a vertebrate, a fungus, a yeast, a bacterium, and a virus. Although the examples herein concern humans and the language is primarily directed to human concerns, the concepts disclosed herein are applicable to genomes from any plant or animal, and are useful in the fields of veterinary medicine, animal sciences, research laboratories and such.

The term "sensitivity" as used herein refers to the probability that a test result will be positive when the condition of interest is present. It may be calculated as the number of true positives divided by the sum of true positives and false negatives.

The term "specificity" as used herein refers to the probability that a test result will be negative when the condition of interest is absent. It may be calculated as the number of true negatives divided by the sum of true negatives and false positives.

The term "primer," as used herein refers to an isolated oligonucleotide that is capable of acting as a point of initiation of synthesis when placed under conditions inductive to synthesis of an extension product (e.g., the conditions include nucleotides, an inducing agent such as DNA polymerase, and a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, use of the method, and the parameters used for primer design.

Introduction

This disclosure provides methods and systems for deconvolution of nucleic acid mixture samples including nucleic acid of two or more contributors of unknown genotypes, providing various advantages and technological improvements. For instance, some implementations apply probabilistic mixture modeling, Bayesian inference techniques, and numerical optimization algorithms to quantify contributor DNA in a mixture without knowing contributor's genotypes.

Sequencing data from a nucleic acid (e.g., DNA or RNA) mixture of closely related genomes is frequently found in research as well as clinical settings, and quantifying the mixing contributors has been a challenge when the original genomes are unknown. Attempts have been made in the art to deconvolve DNA mixture with limited success. Such attempts were made using capillary-electrophoresis (CE) allele data, which data do not provide sequence information of alleles that may be useful in clinical settings. Moreover, capillary-electrophoresis-based analyses are often limited to a relatively small number of alleles known in databases and fail to capture information outside of those alleles. It is desirable to use next-generation-sequencing technology to analyze DNA mixture samples. However, conventional methods for deconvolving DNA samples have not be implemented to analyze NGS data. And even if one wanted to modify conventional methods for NGS data analyses, the modification would not be trivial and the success of such modification is questionable. For example, CE data for alleles are continuous, while allele counts based on sequencing data are discrete. One skilled in the art would appreciate that models for continuous data would not work at all for discrete data, or would perform suboptimally. It is therefore desirable to develop new methods for deconvolving sequencing data (e.g., NGS data) for DNA mixture samples.

Some implementations provide methods and systems for quantifying contributor DNA from multi-marker targeted-resequencing data of blood cfDNA or gDNA samples. Some implementations provide methods and systems for quantifying contributor DNA from multi-marker targeted-resequencing data of blood cfDNA or gDNA samples using novel probabilistic models and numerical optimization algorithms. Some implementations provide methods and systems for quantifying contributor DNA for genetically related donor and recipient of unknown genotypes using Bayesian modeling with prior distributions that encode genetic-relationship. By using genetic-relationship information to provide prior information in a Bayesian framework, quantification of DNA mixture can be improved compared to methods that do not use the genetic-relationship information.

Some implementations provide methods and systems for estimating the confidence interval of DNA quantification by using the Cramer-Rao bound on the estimated Hessian matrices of log-likelihood functions.

Allelic bias in short sequencing read mapping confounds DNA quantification. In some implementations, the confounding effect is reduced by using unbiased mapping of reads spanning variant sites.

Implementations described herein can accurately estimate the contributor DNA fraction even though the genotypes for the contributing genomes are totally unknown. The allele fraction of a marker site after PCR amplification can be reliably modeled with a beta-distribution.

Using the unbiased reference DNA sequence database, one can remove biases towards the reference alleles, and reliably estimate the allele counts and sequencing error at the variant sites.

Implementations described herein can estimate the confidence interval of the predicted contributor DNA fractions with a single sequencing run of a mixture DNA sample.

Experimental Pipeline

FIGS. 1A-1C show an overview of bioinformatics algorithm and statistical model designed for contributor DNA quantification. FIG. 1A shows an experimental pipeline for sequencing based allogeneic DNA detection. FIG. 1B shows an unbiased read mapping workflow for allele counting. FIG. 1C shows a hierarchical, probabilistic mixture model for allelic counts per marker locus.

Some implementations apply experimental pipeline as depicted in FIG. 1A. This generic experimental pipeline has the following steps.
1) A blood sample is obtained containing DNA from two individuals.
2) The appropriate type of DNA is extracted, e.g. cellular DNA or cell free DNA (cfDNA), depending on the application.
3) Specific variant sites or polymorphism sites of the genome is targeted and enriched by approaches such as PCR amplification and hybridization. The variant sites are prior-selected to be variable among diverse populations of human or bacteria. Alternatively, untargeted whole genome sequencing can be done, and all variant sites will be covered.
4) The enriched DNA is sequenced by NGS techniques such as some of the ones described hereinafter to obtain sequencing reads that are enriched for the target genomic regions.

Formal Problem Statement

Formally, the problem of contributor DNA quantification (CDQ) is stated as following: Given the sequencing data of a DNA sample comprised of two contributors, determine the fraction of each contributor in the sample. When the genotypes of the contributor genomes are unknown, the CDQ problem is referred to as blind contributor DNA quantification (blind-CDQ); the opposite is referred to as non-blind-CDQ. Some descriptions regarding some implementations refer to the two contributors as the donor and the recipient, but they do not limit the applications of the methods to the organ donation setting. In some description hereinafter regarding some implementations, a contributor or the contributor is equivalent to a donor, and the other contributor is equivalent to a donee.

Blind-CDQ is a harder problem compared to non-blind CDQ, but it is of wider application to all scenarios where only a single sequencing experiment of the mixture sample is achievable, while the non-blind-CDQ requires prior sequencing experiments to determine genotypes of the contributors (e.g. organ donors and recipients).

The computational methods described in this document address the blind-CDQ problem, and components of the methods can be easily simplified or adapted to be used for the non-blind-CDQ problem.

Overview of the Computational Methods

The computational method for blind-CDQ has two main steps:
1) Allele Counting: a bioinformatics workflow for unbiased counting of sequencing reads from each allele for each target marker site (FIG. 1B), and
2) Contributor DNA Quantification: using a hierarchical probabilistic model and the associated numerical optimization algorithm for quantifying the contributor DNA fraction (FIG. 1C).

Although some implementation only address "relative quantification" here, meaning that the implementations estimate the percentage or fraction of the DNA sample that is originated from the contributor sources, rather than the absolute amount (in terms of mass or copy numbers). Additional steps can be taken to convert the relative abundance to absolute abundance if the total amount of input DNA is known.

Figure 2A:
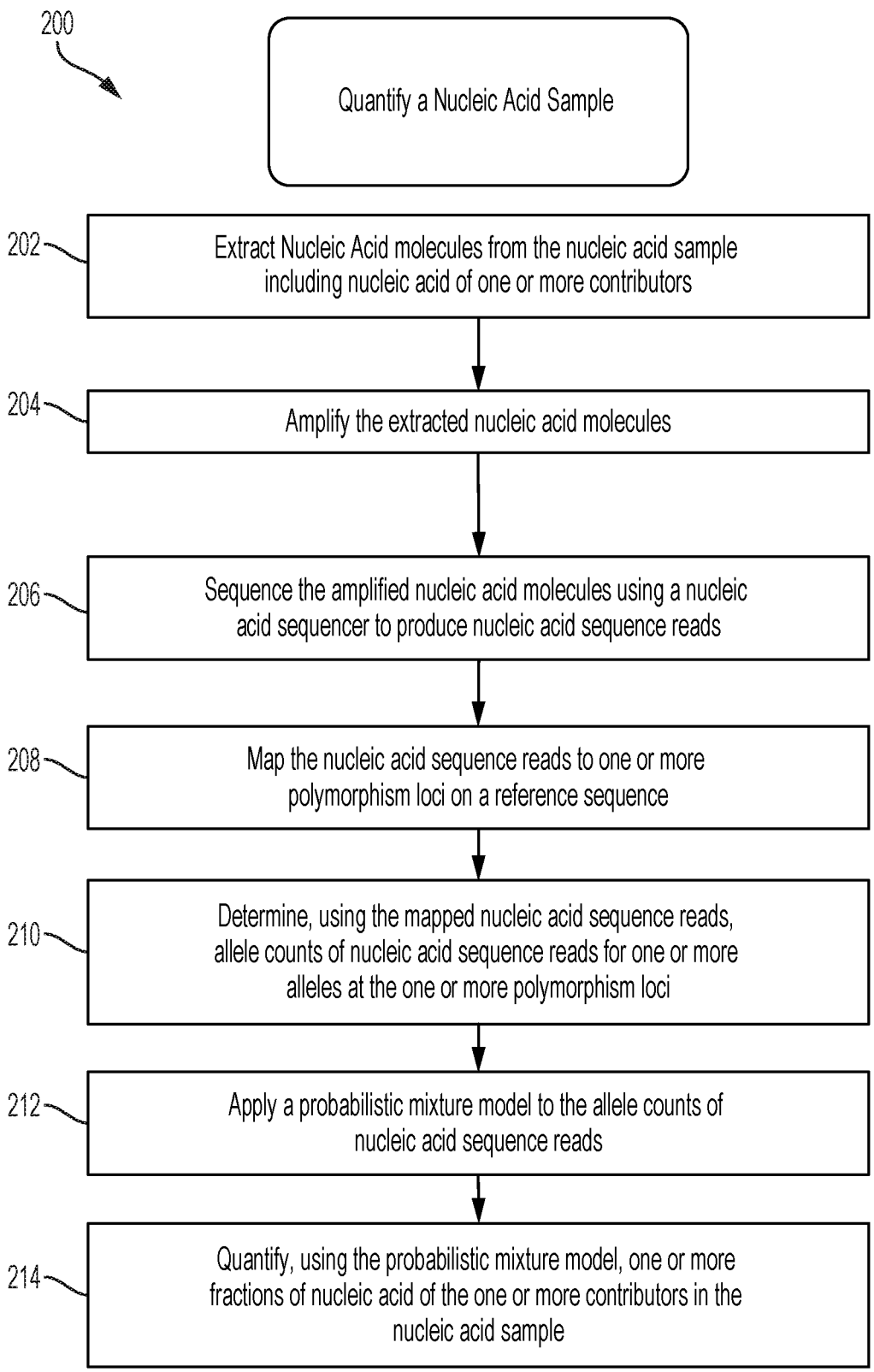
FIG. 2A shows a block diagram illustrating a process for quantifying one or more fractions of nucleic acid (e.g., DNA or RNA) of one or more contributors in the nucleic acid sample.

Overview of Processes for Quantifying Contributor Fractions in a Nucleic Acid Sample or Deconvolving a Nucleic Acid Mixture Sample FIG. 2A shows a block diagram illustrating a process 200 for quantifying one or more fractions of nucleic acid (e.g., DNA or RNA) of one or more contributors in the nucleic acid sample. The nucleic acid sample includes nucleic acid (e.g., DNA or RNA) of the contributor and at least one other contributor. The method is implemented on a computer system that includes one or more processors and system memory such as the systems described hereinafter. Descriptions herein refer to DNA in some implementations and applications, but one skilled in the art appreciates that RNA and other forms of nucleic acids can also be analyzed using the implementations described herein. The various implementations described herein can be used to analyze nucleic acid sample of nucleic acid from one or more contributors. In some implementations, methods and systems are provided to quantify one or more fractions of nucleic acid of the one or more contributors. In some descriptions herein, the nucleic acid sample is referred to as a mixture sample because the sample can include nucleic acid from two more contributors. However, it is understood that the use of the term "mixture" indicates the possibility that the sample includes two or more contributors' nucleic acid, and it does not exclude the possibility that the sample includes nucleic acid from only a single contributor. In the latter case, a fraction of 1 or a percentage of 100% (or values within a margin of error) may be determined for the one contributor.

In some implementations, the one or more contributors of the nucleic acid sample include a donor of a transplant in a donee of the transplant. In some implementations, the transplant includes an allogeneic or a xenogeneic transplant. In some implementations, the nucleic acid sample is a biological sample obtained from the donee. In some implementations, the nucleic acid sample includes cell-free nucleic acid. In some implementations, the sample includes cellular DNA.

Process 200 involves extracting nucleic acid molecules from the nucleic acid sample using techniques such as those described herein. See block 202.

Process 200 further involves amplifying the extracted nucleic acid molecules. See block 204. Various amplification techniques such as those described herein may be used. In some implementations, PCR are used to amplify the extracted nucleic acid molecules. In some implementations, the amplification targets specific polymorphisms. In other implementations, whole genome amplification may be performed, and allele data for specific polymorphism sites may be obtained by sequencing.

Process 200 also involves sequencing the amplified nucleic acid molecules using a nucleic acid sequencer to produce nucleic acid sequence reads. See block 206. Various sequencing techniques and devices are further described hereinafter, which may be applied in operation 206.

Process 200 further involves mapping the nucleic acid sequence reads to one or more polymorphism loci on a reference sequence. In some implementations, alignment techniques may be used to map the nucleic acid sequence reads to one or more polymorphism loci. In other implementations, an unbiased mapping techniques may be used to match the nucleic acid sequence reads to the polymorphism loci. See block 208. In some implementations, the nucleic acid sequence reads are mapped to specific alleles at the polymorphism loci. The unbiased mapping technique is further described hereinafter. In some implementations, the one or more polymorphism loci (or polymorphic loci) include biallelic loci. In some implementations, the alleles at the one or more polymorphism loci include single nucleotide polymorphism (SNP) alleles.

In some implementations, unique molecular indexes (UMIs) are attached to the extracted nucleic acid molecules, which are then amplified, sequenced, and mapped to the polymorphism loci or alleles. The unique molecular indices provide mechanisms to reduce the errors that can occur in the sample processing and analysis steps. For instance, different reads sharing a same unique molecular index (UMI) can be combined or collapsed to determine a sequence from which the reads are derived, effectively removing errors that have occurred during sample processing and sequencing.

Process 200 further involves determining, using the method nucleic acid sequence reads, allele counts of nucleic acid sequence reads for alleles at the one or more polymorphism loci. See block 210.

Process 200 also involves applying the probabilistic mixture model to the allele counts of nucleic acid sequence reads. The probabilistic mixture model uses probability distributions to model allele count of nucleic acid sequence reads at the one or more polymorphism loci. The probability distributions account for errors in the nucleic acid sequence reads. The probabilistic mixture model treats each allele count of nucleic acid sequence reads as a random sample from a probability distribution.

In some implementations, the probability distribution includes a first binomial distribution. In some implementations, the first binomial distribution includes a quantity parameter indicating the total allele count at a locus and a probably parameter indicating a probability of the first allele at the locus. In some implementations, the first binomial distribution is expressed as follows:

$$n_{ij} \sim BN(n_i, p_i)$$

wherein $n_{ij}$ is an allele count of nucleic acid sequence reads for allele j at locus i; $n_i$ is a total read count at locus i; and $p_{ij}$ is a probability parameter indicating the probability of allele j at locus i. The allele probabilities for all possible alleles at the locus add up to 1.

Figure 2B:
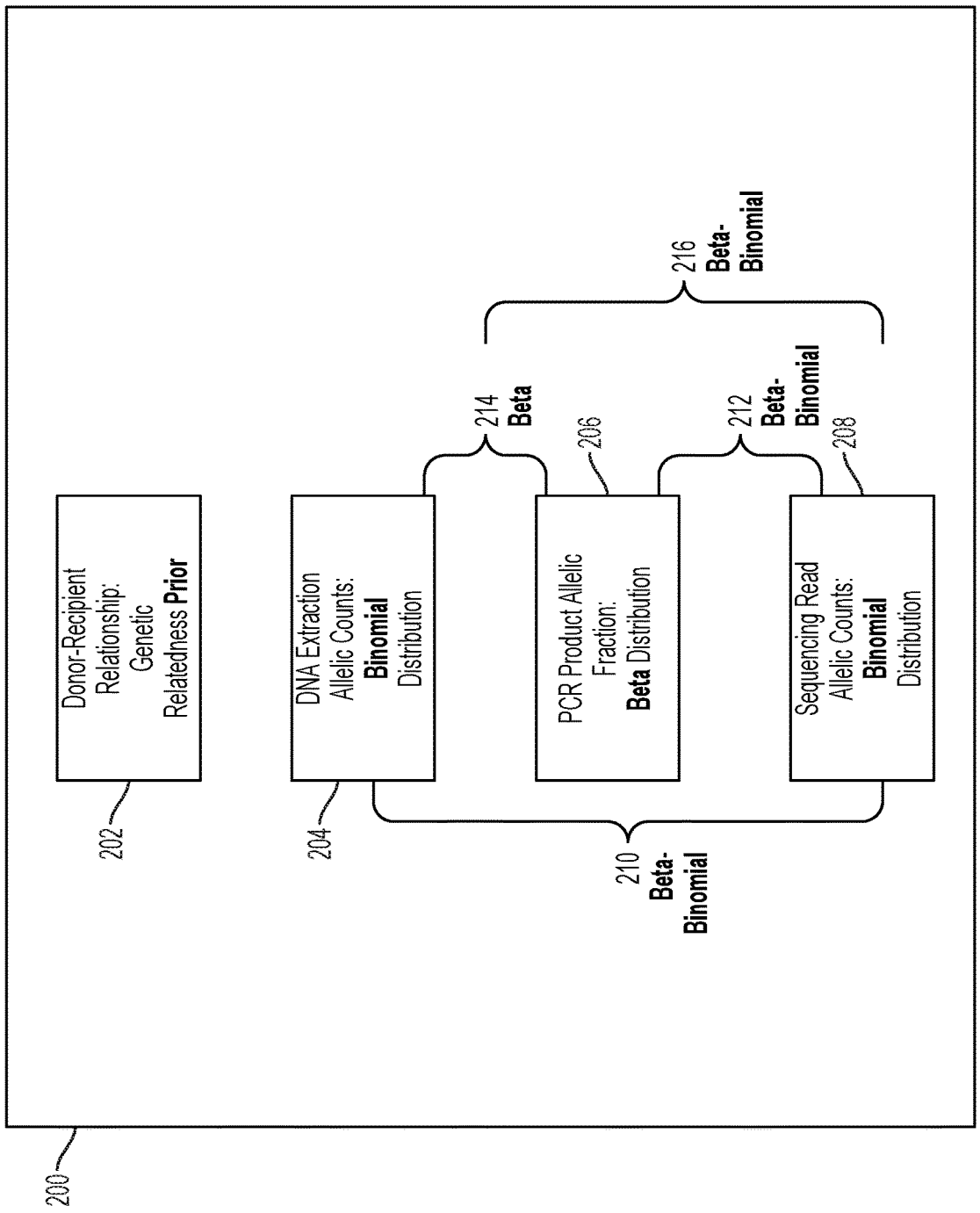
FIG. 2B shows a block diagram illustrating various components of a probabilistic mixture model.

In some implementations, the probability parameter is a function of a fraction of nucleic acid of a contributor, or β. The probably parameter is also a function of genotypes of the one or more contributors. The probability parameter is also a function of errors resulting from the sequencing operation of 206, or λ. In some implementations, the probability parameter is obtained using the $p_1'$ values in Table 3 described hereinafter. In some implementations, genotypes of one or more of the contributors were unknown. In some implementations the probabilistic mixture model includes various probability distributions as shown in FIG. 2B.

Returning to FIG. 2A, process 200 concludes quantifying, using the probabilistic mixture model, one or more fractions of nucleic acid of the one or more contributors in the nucleic acid sample. See block 214. In some implementations, the quantifying includes marginalizing over a plurality of possible combinations of genotypes to obtain the probability parameter. In some implementations, the quantifying includes quantifying the fractions of nucleic acid of the contributors using a likelihood function of the allele counts of nucleic acid sequence reads determined in operation 210 conditioned on parameters of the probabilistic mixture model.

In some implementations, the quantification includes calculating a plurality of likelihood values using a plurality of potential fraction values and a likelihood function of the allele counts of nucleic acid sequence reads. The quantification also involves identifying a potential fraction value that is associated with a likelihood value that is the maximum value among the plurality of likelihood values. In some implementations, the plurality of likelihood values is obtained for a plurality of parameters and the values thereof in a grid. The quantification also involves quantifying the fraction of nucleic acid of the contributor in the nucleic acid sample at the identified potential fraction value having the maximum likelihood. In some implementations, the likelihood function includes a plurality of marginal distributions for the one or more polymorphism loci.

In some implementations, the one or more contributors are modeled as two contributors and the likelihood function follows the following:

$$L(n_1, \ldots n_j | \beta, \pi) = \Pi_i \Pi_{g_{1j}g_{2j}} BN(n_{ij}, p_{ij}(g_{1j}, g_{2j}, \lambda, \beta)) \cdot P(g_{1j}, g_{2j} | \pi)$$

wherein $L(n_1, \ldots n_j | \beta, \pi)$ is the likelihood of observing allele counts $n_1$ to $n_j$ for alleles 1 to j given parameters β (the fraction of nucleic acid of the one of the contributors) and π (a population allele frequency); $p_{ij}(g_{1j}, g_{2j}, \lambda, \beta)$ is a probability parameter indicating a probability of allele j at locus i based on the two contributors' genotypes of allele j($g_{1j}$, $g_{2j}$); and $P(g_{1j}, g_{2j} | \pi)$ is a prior joint probability of observing the genotypes of allele j for the two contributors given a population allele frequency (π).

In some implementations, the probabilistic mixture model accounts for errors resulting from extracting the nucleic acid molecules performed in 202, as well as the errors resulting from the sequencing operation in 206.

In some implementations, the probabilistic mixture model uses a second binomial distribution to model allele counts of the extracted nucleic acid molecules for alleles at the one or more polymorphism loci. In some implementations, the second binomial distribution is expressed as follows:

$$n_{ij}'' \sim BN(n_i'', p_{ij})$$

wherein $n_{ij}''$ is an allele count of extracted nucleic acid molecules for allele j at locus i; $n_i''$ is a total extracted nucleic acid molecule count at locus i; and $p_{ij}$ is a probability parameter indicating the probability of allele j at locus i.

In some implementations, the first binomial distribution is conditioned on an allele fraction $n_{ij}''/n_i''$. In some implementations, the first binomial distribution is re-parameterized as follows:

$$n_{ij} | n_{ij}'', n_i'' \sim BN(n_i, n_{ij}''/n_i'')$$

wherein $n_{ij}$ is an allele count of nucleic acid sequence reads for allele j at locus i; $n_i"$ is a total number of extracted nucleic acid molecules at locus i, which equals to a total genome copy numbers n"; $n_i$ is a total read count at locus i; and $n_{ij}"$ is a number of extracted nucleic acid molecules for allele j at locus i.

In some implementations, the probabilistic mixture model uses a first beta distribution to approximate a distribution of $n_{ij}"/n"$. In some implementations, the first beta distribution has a mean and a variance that match a mean and a variance of the second binomial distribution.

In some implementations, locus i is modeled as biallelic and the first beta distribution is expressed as follows:

$$n_{i1}"/n" \sim Beta((n"-1)p_{i1}, (n"-1)p_{i2})$$

wherein $p_{i1}$ is a probability parameter indicating the probability of a first allele at locus i; and $p_{i2}$ is a probability parameter indicating the probability of a second allele at locus i.

In some implementations, the process includes combining the first binomial distribution and the first beta distribution to obtain a marginal distribution of nil that follows a first beta-binomial distribution.

In some implementations, the one or more contributors are modeled as two contributors and the first beta-binomial distribution has the form:

$$BB(n_{i1}, n_{i2}|n_i, (n"-1) \cdot p_1(g_{11}, g_{21}, \lambda, \beta), (n"-1) \cdot p_2(g_{11}, g_{21}, \lambda, \beta))$$

wherein $n_{i2}$ is an allele count of nucleic acid sequence reads for the second allele at locus i; $p_1(g_{11}, g_{21}, \lambda, \beta)$ is a probability parameter indicating a probability of the first allele based on a first contributor's genotype for the first allele ($g_{11}$) and a second contributor's genotype for the first allele ($g_{21}$), as well as the sequencing error λ and the contributor fraction β; and $p_2(g_{11}, g_{21}, \lambda, \beta)$ is a probability parameter indicating a probability of the second allele based on the first contributor's genotype for the first allele ($g_{11}$) and the second contributor's genotype for the first allele ($g_{21}$), as well as the sequencing error λ and the contributor fraction β.

In some implementations, operation 214 includes quantifying the one or more fractions of nucleic acid of the one or more contributors in the nucleic acid sample using a likelihood function obtained using the first beta-binomial distribution, the likelihood function follows:

$$L(n_1, n_2|\beta, n", \lambda, \pi) = \Pi_i \Sigma_{g11g21} BB(n_{i1}, n_{i2}|n_i, (n"-1) \cdot p_1(g_{11}, g_{21}, \lambda, \beta), (n"-1) \cdot p_2(g_{11}, g_{21}, \lambda, \beta)) \cdot P(g_{11}, g_{21}|\pi)$$

wherein $L(n_1, n_2|\beta, n", \lambda, \pi)$ is the likelihood of observing an allele count for the first allele ($n_1$) and an allele count for the second allele ($n_2$) given parameters β, n", λ, and π; and $P(g_{11}, g_{21}|\pi)$ is a prior joint probability of observing the first contributor's genotype for the first allele ($g_{11}$) and the second contributor's genotype for the first allele ($g_{21}$) given a population allele frequency (π).

In some implementations, operation 214 includes estimating the total extracted genome copy number n" from a mass of the extracted nucleic acid molecules.

In some implementations, the probabilistic mixture model accounts for errors resulting from amplifying the nucleic acid molecules performed in 204, as well as the errors resulting from the sequencing operation in 206. In some implementations, the amplification process is modeled as follows:

$$x_{t+1} = x_t + y_{t+1}$$

wherein $x_{t+1}$ is the nucleic acid copies of a given allele after cycle t+1 of amplification; $x_t$ is the nucleic acid copies of a given allele after cycle t of amplification; $y_{t+1}$ is the new copies generated at cycle t+1, and it follows a binomial distribution $y_{t+1} \sim BN(x_t, r_{t+1})$; and $r_{t+1}$ is the amplification rate for cycle t+1.

In some implementations, the probabilistic mixture model uses a second beta distribution to model allele fractions of the amplified nucleic acid molecules for alleles at the one or more polymorphism loci. In some implementations, locus i is modeled as biallelic and the second beta distribution is expressed as follows:

$$n_{i1}'/(n_{i1}' + n_{i2}') \sim Beta(n" \cdot \rho_i \cdot p_{i1}, n" \cdot \rho_i \cdot p_{i2})$$

wherein $n_{i1}'$ is an allele count of amplified nucleic acid molecules for a first allele at locus i; $n_{i2}'$ is an allele count of amplified nucleic acid molecules for a second allele at locus i; n" is a total extracted nucleic acid molecule count at any locus; $\rho_i$ is a constant related to an average amplification rate r; $p_{i1}$ is the probability of the first allele at locus i; and $p_{i2}$ is a probability of the second allele at locus i. In some implementations, $\rho_i$ is $(1+r)/(1-r)/[1-(1+r)^{-r}]$. In some implementations, $\rho_i$ is approximated as $(1+r)/(1-r)$.

In some implementations, operation 214 includes combining the first binomial distribution and the second beta distribution to obtain a marginal distribution of $n_{i1}$ that follows a second beta-binomial distribution. In some implementations, the second beta-binomial distribution has the form:

$$BB(n_{i1}, n_{i2}|n_i, n" \cdot \rho_i \cdot p_{i1}, n" \cdot \rho_i \cdot p_{i2})$$

wherein $n_{i2}$ is an allele count of nucleic acid sequence reads for the second allele at locus i; $p_{i1}$ is a probability parameter indicating the probability of a first allele at locus i; and $p_{i2}$ is a probability parameter indicating the probability of a second allele at locus i.

In some implementations, operations 214 includes, by assuming the one or more polymorphism loci have a same amplification rate, re-parameterizing the second beta-binomial distribution as:

$$BB(n_{i1}, n_{i2}|n_i, (1+r)/(1-r) \cdot p_1(g_{11}, g_{21}, \lambda, \beta), (1+r)/(1-r) \cdot p_2(g_{11}, g_{21}, \lambda, \beta))$$

wherein r is an amplification rate; and $p_{i2}$ is a probability parameter indicating the probability of a second allele at locus i.

In some implementations, operation 214 includes quantifying the one or more fractions of nucleic acid of the one or more contributors in the nucleic acid sample using a likelihood function obtained using the second beta-binomial distribution, the likelihood function follows:

$$L(n_1, n_2|\beta, r, \lambda, \pi) = \Pi_i \Sigma_{g11g21}[BB(n_{i1}, n_{i2}|n_i, (1+r)/(1-r) \cdot p_1(g_{11}, g_{21}, \lambda, \beta), (1+r)/(1-r) \cdot p_2(g_{11}, g_{21}, \lambda, \beta)) \cdot P(g_{11}, g_{21}|\pi)]$$

wherein $L(n_1, n_2|\beta, r, \lambda, \pi)$ is the likelihood of observing an allele count for the first allele ($n_1$) and an allele count for the second allele ($n_2$) given parameters β, r, λ, and π.

In some implementations, operation 214 includes, by defining a relative amplification rate of each polymorphism locus to be proportional to a total reads per locus, re-parameterizing the second beta-binomial distribution as:

$$BB(n_{i1}, n_{i2}|n_i, c' \cdot n_i \cdot p_{i1}(g_{11}, g_{21}, \lambda, \beta), c' \cdot n_i \cdot p_{i2}(g_{11}, g_{21}, \lambda, \beta))$$

wherein c' is a parameter to be optimized; and $p_{i2}$ is a probability parameter indicating the probability of a second allele at locus i.

In some implementations, operation 214 includes quantifying the one or more fractions of nucleic acid of the one or more contributors in the nucleic acid sample using a likelihood function obtained using the second beta-binomial distribution, the likelihood function follows:

$$L(n1,n2|\beta,c'',\lambda,\pi)=\Pi_i\Sigma_{g11g21}[BB(n_{i1},n_{i2}|n_i,c'\cdot n_i\cdot p_1(g_{11},g_{21},\lambda,\beta),c'\cdot n_i\cdot p_2(g_{11},g_{21},\lambda,\beta))\cdot P(g_{11},g_{21}|\pi)].$$

In some implementations, the probabilistic mixture model accounts for errors resulting from extracting the nucleic acid molecules performed in 202 and amplifying the nucleic acid molecules performed in 204, as well as the errors resulting from the sequencing operation in 206. In some implementations, the probabilistic mixture model uses a third beta distribution to model allele fractions of the amplified nucleic acid molecules for alleles at the one or more polymorphism loci, accounting for the sampling errors resulting from extracting the nucleic acid molecules performed in 202 and amplifying the nucleic acid molecules performed in 204, as well as the errors resulting from the sequencing operation in 206.

In some implementations, locus i is modeled as biallelic and the third beta distribution has the form of:

$$n_{i1}'/(n_{i1}'+n_{i2}')\sim Beta([n'''\cdot(1+r_i)/2-1]p_{i1}, [n'''\cdot(1+r_i)/2-1]p_{i2})$$

wherein $n_{i1}'$ is an allele count of amplified nucleic acid molecules for a first allele at locus i; $n_{i2}'$ is an allele count of amplified nucleic acid molecules for a second allele at locus i; n''' is a total extracted nucleic acid molecule count; $r_i$ is the amplification rate at locus i; $p_{i1}$ is the probability of the first allele at locus i; and $p_{i2}$ is a probability of the second allele at locus i.

In some implementations, operation 214 includes combining the first binomial distribution and the third beta distribution to obtain a marginal distribution of $n_{i1}$ that follows a third beta-binomial distribution. In some implementations, the third beta-binomial distribution has the form:

$$BB(n_{i1},n_{i2}|n_i,(n'''\cdot(1+r_i)/2-1)\cdot p_1(g_{11},g_{21},\lambda,\beta), (n'''\cdot(1+r_i)/2-1)\cdot p_2(g_{11},g_{21},\lambda,\beta)).$$

In some implementations, operation 214 includes quantifying the one or more fractions of nucleic acid of the one or more contributors in the nucleic acid sample using a likelihood function obtained using the third beta-binomial distribution, the likelihood function comprising:

$$L(n_1,n_2|\beta,\lambda,\pi)=\Pi_i\Sigma_{g11g21}BB(n_{i1},n_{i2}|n_i,(n'''\cdot(1+r)/(2-1)\cdot p_1(g_{11},g_{21},\lambda,\beta),(n'''\cdot(1-r_i)/2-1)\cdot p_2(g_{11},g_{21},\lambda,\beta))\cdot P(g_{11},g_{21}|\pi).$$

wherein $L(n_1, n_2|\beta, n''', \lambda, \pi)$ is the likelihood of observing an allele count for the first allele $n_1$ and an allele count for the second allele $n_2$ given parameters $\beta$, n''', $\lambda$, and $\pi$;

In some implementations, process 200 further includes estimating, using the Cramer-Rao inequality, one or more confidence intervals of the one or more fractions of nucleic acid of the one or more contributors.

In some implementations, the mapping operation of 208 includes identifying reads among the nucleic acid sequence reads matching any sequence of a plurality of unbiased target sequences, wherein the plurality of unbiased target sequences includes sub-sequences of the reference sequence and sequences that differ from the subsequences by a single nucleotide.

In some implementations, the plurality of unbiased target sequences comprises five categories of sequences: (i) reference target sequences that are sub-sequences of the reference sequence, each reference target sequence encompassing a polymorphic locus and having a reference allele found on the reference sequence; (ii) alternative target sequences corresponding to reference target sequences, each alternative target sequence having an alternative allele different from a reference allele found on a corresponding reference target sequence, wherein corresponding sequences have a same length and a same location on the reference sequence; (iii) mutated reference target sequences comprising all possible sequences that each differ from a reference target sequence by only one nucleotide other than a nucleotide defining the difference between a reference allele and an alternative allele; (iv) mutated alternative target sequences comprising all possible sequences that each differ from an alternative target sequence by only one nucleotide other than a nucleotide defining the difference between a reference allele and an alternative allele; and (v) unexpected allele target sequences corresponding to reference target sequences, each unexpected allele target sequence having an unexpected allele different from a reference allele found on a corresponding reference target sequence and an alternative allele found on a corresponding alternative target sequence, wherein corresponding sequences have a same length and a same location on the reference sequence.

In some implementations, operation 208 includes using the identified reads and their matching unbiased target sequences to determine allele counts of the nucleic acid sequence reads for the alleles at the one or more polymorphism loci. In some implementations, the plurality of unbiased target sequences includes sequences that are truncated to have the same length as the nucleic acid sequence reads. In some implementations, the plurality of unbiased target sequences includes sequences stored in one or more hash tables, and the reads are identified using the hash tables.

In some implementations, the process 200 further includes determining an allele configuration at each of the one or more polymorphism loci, each allele configuration comprising allele status of two or more alleles for each of the one or more contributors.

Figure 3:
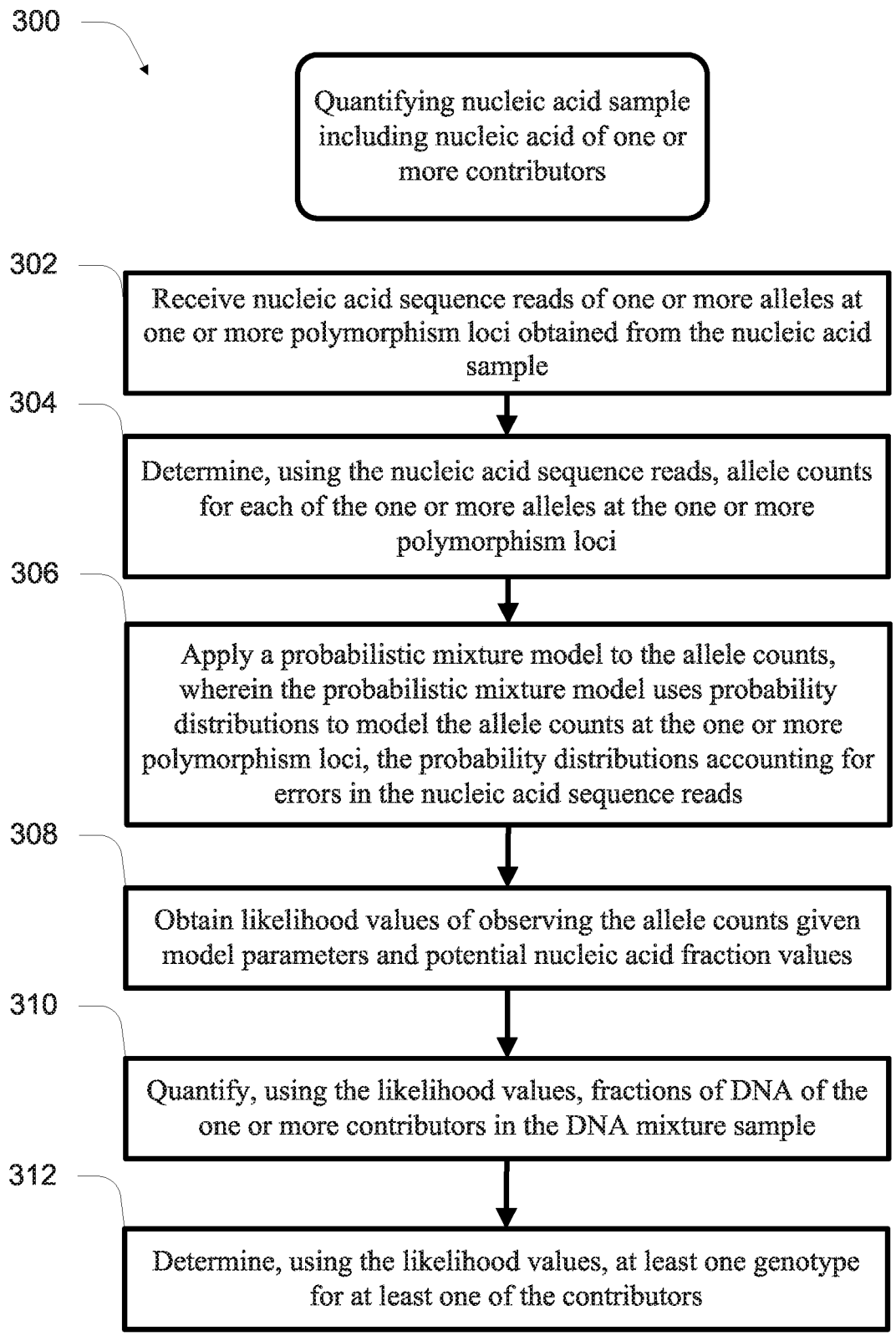
FIG. 3 shows a block diagram illustrating a process for evaluating a nucleic acid sample including nucleic acid of one or more contributors.

FIG. 3 shows a block diagram illustrating process 300 for evaluating a nucleic acid sample including nucleic acid of one or more contributors. Process 300 starts by receiving nucleic acid sequence reads of one or more alleles at one or more polymorphism loci obtained from the nucleic acid sample. See block 302. In some implementations, the nucleic acid sequence reads were obtained by sequencing the nucleic acid in the nucleic acid sample using various techniques described herein.

In some implementations, unique molecular indexes (UMIs) are attached to the extracted nucleic acid molecules, which are then amplified, sequenced, and mapped to the polymorphism loci or alleles. The unique molecular indices provide mechanisms to reduce the errors that can occur in the sample processing and analysis steps. For instance, different reads sharing a same unique molecular index (UMI) can be combined or collapsed to determine a sequence from which the reads are derived, effectively removing errors that have occurred during sample processing and sequencing. U.S. patent application Ser. No. 15/130, 668 filed Apr. 16, 2016, and U.S. Provisional Patent Application No. 62/447,851 filed Jan. 18, 2017 describe various methods and systems for sequencing nucleic acids using unique molecular indexes, which are incorporated by reference by their entireties for all purposes.

Process 300 further involves determining, using the nucleic acid sequence reads, allele counts for the one or more alleles at the one or more polymorphism loci.

Process 300 also involves applying the probabilistic mixture model to the allele counts. The probabilistic model uses probabilistic distributions to model allele counts of alleles at the one or more polymorphism loci. The probabilistic distributions count for errors in the allele data. The errors include errors originating from nucleic acid extraction, sample processing, and sequencing operations.

In some implementations, the probabilistic distributions include a first binomial distribution. In some implementations, the first binomial distribution includes a parameter indicating the total allele count at a locus and a probability parameter indicating the probability of the first allele at the locus. In some implementations, the probability parameter is a function of the fractions of nucleic acid of the one or more contributors in the nucleic acid sample. The probability parameter is also a function of genotypes of the one or more contributors, or G, and a function of errors in the nucleic acid sequence read data, or θ. In some implementations, the errors in the read data include errors originating from nucleic acid extraction, sample processing, and sequencing operations.

Process 300 also involves obtaining likelihood values of observing the allele data given model parameters and potential nucleic acid fraction values. See block 308.

In some implementations, process 300 involves quantifying, using the likelihood values, fractions of nucleic acid of the one or more contributors in the nucleic acid sample. See block 310.

In some implementations, process 300 further involves determining, using the likelihood values, at least one genotype for at least one of the contributors. See block 312.

In some implementations, genotypes of the contributors were unknown prior to process 300.

In some implementations, the probabilistic mixture model uses a beta distribution to model the errors in the allele data. In some implementations, the beta distribution is defined by a mean parameter and a concentration parameter. In some implementations, the concentration parameter has discrete prior representing different noise conditions. The concentration parameter varies across loci.

In some implementations, the quantification of operation 310 includes combining the first binomial distribution and the beta distribution to obtain a marginal distribution that follows a beta-binomial distribution.

In some implementations, the quantification of 310 includes quantifying the fractions of nucleic acid of the one or more contributors in the nucleic acid sample using a likelihood function of the allele data. In some implementations, the quantification involves calculating a plurality of likelihood values using a plurality of potential fraction values and a likelihood function of the allele counts. The quantification also involves identifying a potential fraction vector associated with the maximum likelihood value, and quantifying the fractions of nucleic acid of the one or more contributors in the nucleic acid sample using the identified potential fraction vector.

In some implementations, the likelihood function depends on $P(G|\pi)$, which is a prior probability of the genotype of the one or more contributors given a population allele frequency ($\pi$). In some implementations, the prior probability is calculated considering a dummy allele with a fixed prior probability representing mechanistic drop-out.

In some implementations, the one or more contributors include two or more contributors. In some implementations, process 300 includes an operation of determining a total number of contributors in the one or more contributors. In some implementations, one or more genotypes of the one or more contributors were unknown, and process 300 includes an operation of determining an allele configuration at each of the one or more polymorphism loci, the allele configuration comprising allele status of two or more alleles for each of the contributors. In some implementations, process 300 includes an operation of determining an estimated probability for the allele configuration.

In some implementations, process 300 further includes obtaining a posterior probability that a specific contributor among the one or more contributors has a specific genotype. In some implementations, process 300 further includes calling, based on the posterior probability, that the nucleic acid sample includes nucleic acid from the specific contributor. In some implementations, obtaining the posterior probability that a specific contributor among the one or more contributors has a specific genotype includes: (i) multiplying prior probabilities of genotype configurations by likelihoods of the genotype configurations; (ii) normalizing a product of (i) by a sum over genotype space; and (iii) summing over genotype configurations containing the specific genotype to obtain the posterior probability.

In some implementations, the specific genotype includes a multiple-locus genotype, and the method further includes: summing, over all contributors, a posterior probability that a contributor has the specific genotype at all loci; and determining, based on the summed probability, the specified multiple-locus genotype appears in any contributor.

In some implementations, the nucleic acid sample is a forensic sample and the data of the multiple-locus genotype is obtained from a person of interest. The process further includes determining that the person of interest is a contributor of the nucleic acid sample.

In some implementations, the probabilistic mixture model uses a second binomial distribution to model stutter errors in the allele data. In some implementations, the second binomial distribution is expressed as follows:

$$s_{ik} \sim BN(n_{i(k+1)}, r_i)$$

where $s_{ik}$ is a stutter allele count at locus i of a stutter allele that appears to be allele k but actually results from a stutter error of allele k+1; $n_{i(k+1)}$ is an original allele count of allele k+1 at locus i; and $r_i$ is a stutter rate for locus i.

In some implementations, the stutter rate r varies across loci and has a prior representing different noise conditions, the prior being shared across loci.

In some implementations, operation 310 includes quantifying fractions of nucleic acid of the one or more contributors in the nucleic acid sample using a likelihood function including a product of likelihoods of non-stutter allele counts and likelihoods of stutter allele counts.

In some implementations, applying the probabilistic mixture model includes adding a fixed number of molecules to an allele count assigned to allele k+1 when determining a number of molecules from which stutter can potentially originate.

In some implementations, the probabilistic mixture model uses a dummy out-of-sample allele to model natural dropout. In some implementations, the prior of the dummy out-of-sample allele is proportional to a number of unobserved alleles. In some implementations, the number of unobserved alleles is estimated by: interpolating all integers between the shortest and longest observed integer-valued alleles, adding any observed non-integer-valued alleles, and returning the maximum of the resulting value and a criterion value.

In some implementations, applying the probabilistic mixture model involves pruning genotype configurations from data used to quantify the fractions of nucleic acid of the one or more contributors in the nucleic acid sample. In some implementations, pruning genotype configurations involves: limiting genotype configurations that are plausible by constructing a list of required alleles and excluding loci with not enough contributors to explain all required alleles. In some implementations, the list of required alleles consists essentially of alleles having allele counts above a threshold and too high to be plausible due to stutter drop-in. In some implementations, the threshold is a sum of (i) a maximum non-stutter allele count, and (ii) a value multiplied by a count of potential stutter donor alleles. In some implementations, pruning genotype configurations involves removing genotype configurations that have poor matches between the allele data and expected allele counts. In some implementations, the genotype configurations that have poor matches have root mean squared error (RMSE) values larger than one or more thresholds.

In some implementations, the alleles at the one or more polymorphism loci include single nucleotide polymorphism (SNP) alleles and/or short tandem repeat (STR) alleles.

Method for Unbiased Mapping of Reads to Marker Sites

Conventional computational methods for mapping nucleic acid (e.g., DNA or RNA) sequencing reads to the genome can be biased by the reference genome used. Since only one allele (the reference allele) for each variant site is present in the reference genome, mismatches between the reads and references are treated as sequencing errors in existing read mapping algorithms. The problem is that when reads containing the non-reference alleles are treated as containing sequencing errors, the alignment confidence (score) is decreased, and hence they are less likely to be retained as confidently mapped reads in subsequent filtering steps. This mapping bias will skew the allele counts (FIG. 1B), and subsequently compromise the estimation of contributor DNA fractions.

To address the mapping bias issue and enable optimal CDQ, some implementations provide a novel workflow for mapping reads to variant sites. The new read mapping approach enables unbiased counting of alleles and estimation of sequencing error on variant sites and non-variant sites.

The read mapping workflow is as follows. The workflow first generates five types of sequences (see Table 1) based on 1) the reference sequences and 2) the known alleles of the variant sites. If more than one single mutation is allowed per sequence, more types of sequences will be generated. The five types of sequences are referred to as ref, alt, ref.mut, alt.mut, and snp.mut respectively. For example, for each biallelic SNP marker site covered by a target sequence of length L, there are one ref, one alt, [L−1]×3 ref.mut, [L−1]×3 alt.mut, and 2 snp.mut sequences. All five types of sequences are then included in the database of "unbiased target sequences" (FIG. 1B). Depending on the length of the reads from the sequencer, the unbiased target sequences are then truncated into two versions. Let r be the read length. Version 1 of the truncated target sequences comprises the r 5' bases of all unbiased target sequences, while version 2 of the truncated target sequences comprises the reverse complement of the r 3' bases of all unbiased target sequences. Redundant sequences in truncated target sequences are then removed. The unique sequences in the two truncated sequence databases are then recorded into two hash tables. Next, sequencing reads are counted using the hash tables. For pair end sequencing strategies, R1 reads and R2 reads are counted using the first and second hash tables respectively. For non-pair end sequencing, all reads are counted using the first hash table. Finally, for each marker site, the counts are aggregated into the five types defined above depending on which type the truncated unbiased target sequences corresponds to in Table 1.

A similar strategy can be implemented when sequence alignment tools are used instead of using hash table for the mapping. For each marker site, the ref and alt types of sequences are generated to form the unbiased sequence database. Each sequencing read is then aligned to this database with up to a predefined number of sequencing errors. The mapped reads are then categorized based on Table 1. For SNP markers only biallelic SNPs are considered here.

TABLE 1

Definition of five types of sequences to be generated from the reference sequence around a variant site.

| Type | Definition |
| --- | --- |
| ref | SNP site taking reference allele |
| alt | SNP site taking alternative allele |
| ref.mut | Single mutation on non SNP site when the SNP site is ref |
| alt.mut | Single mutation on non SNP site when the SNP site is alt |
| snp.mut | SNP site taking neither reference nor alternative alleles |

The proposed read mapping workflow addresses the read mapping bias issue when tested using real data. With the workflow, the observed error rates of the reference to alternative errors and the alternative to reference errors are identical. The sequencing error rate on the non-variant sites on the reference DNA copy and that on the alternative DNA copy are also identical.

Linking Contributor DNA Fraction with Allele Fractions

Assuming No Sequencing Error

We assume there are $n_d$ donor cells and $n_r$ recipient cells that supplied DNA to the sample. Based on these cells, the implementations define the minor contributor fraction as $\beta = n_d/(n_d + n_r)$. Depending on the genotypes of donor and recipient at each specific locus, the two alleles have different fractions (see Table 2 for details), and the generic formula for calculating them is $p_1 = [g_{11}(1-\beta) + c \cdot g_{21} \cdot \beta]/2$ and $p_2 = [g_{12}(1-\beta) + g_{22} \cdot \beta]/2$. Note that $g_{11}$ and $g_{12}$ are the recipient genotype, i.e. copies of allele 1 and 2 in the recipient genome; $g_{21}$ and $g_{22}$ are donor genotype, i.e. copies of allele 1 and 2 in the donor genome.

TABLE 2

The binomial model parameters $p_1$ and $p_2$ for the 9 possible genotype combinations between a donor and recipient pair for a given variant site

| $g_{11}$ | $g_{21}$ | $p_1$ | $p_2$ |
| --- | --- | --- | --- |
| 0 | 0 | 0 | 1 |
| 0 | 1 | $\beta/2$ | $1 - \beta/2$ |
| 0 | 2 | $\beta$ | $1 - \beta$ |
| 1 | 0 | $(1 - \beta)/2$ | $(1 + \beta)/2$ |
| 1 | 1 | 1/2 | 1/2 |
| 1 | 2 | $(1 + \beta)/2$ | $(1 - \beta)/2$ |
| 2 | 0 | $1 - \beta$ | $\beta$ |
| 2 | 1 | $1 - \beta/2$ | $\beta/2$ |
| 2 | 2 | 1 | 0 |

Modeling Sequencing Error

When there are two known alleles at a variant site, sequencing errors will convert one allele to another in addition to converting the two known alleles to the two remaining nucleotides at this locus. The consequence is that the allele fractions in the sequenced reads will deviate from the allele fractions in the NGS input DNA sample.

Figure 2C:
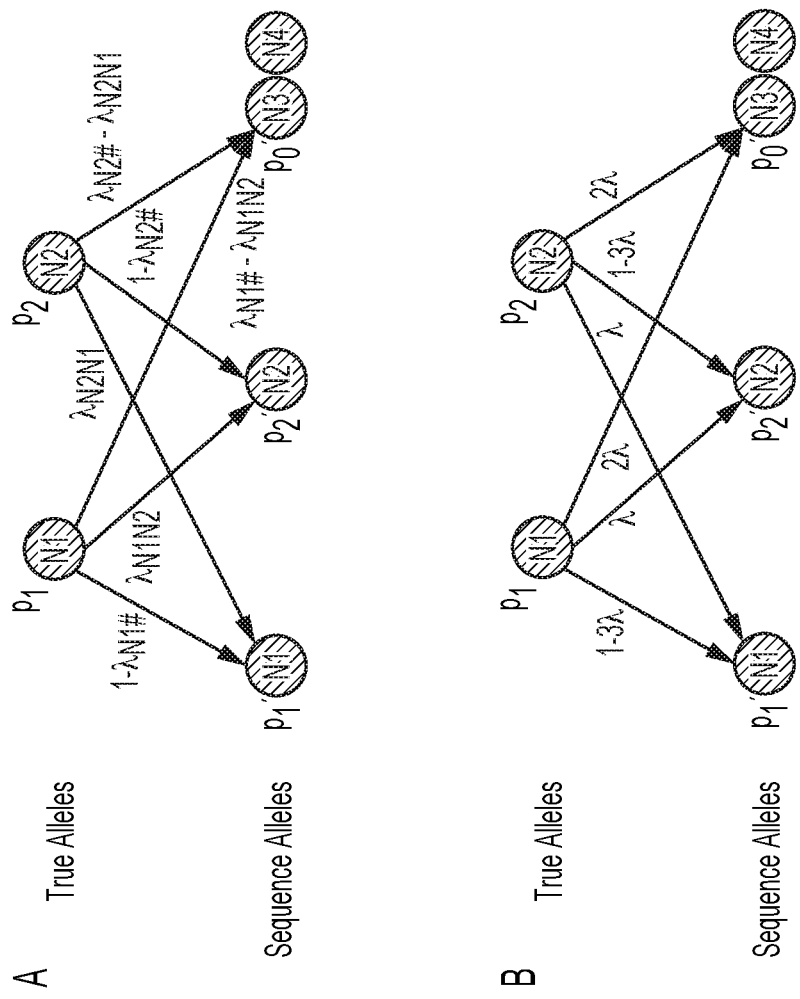
FIG. 2C schematically illustrates sequencing errors that convert one allele to another allele and true alleles to unexpected alleles.

FIG. 2C schematically illustrates sequencing errors that convert one allele to another allele and true alleles to unexpected alleles. Panel (A) shows nucleotide-dependent sequencing error, and panel (B) shows uniform sequencing error.

Let $N_1$, $N_2$ be the allele 1 and allele 2 nucleotides. Let $p_1'$, $p_2'$ be the probability of observing allele 1 and allele 2 reads respectively, whether it is real or due to sequencing error; and $p_0'=1-p_1'-p_2'$ be the probability of observing the two unexpected alleles due to sequencing error. Let $\lambda_{N1N2}$ be the mutation rate (probability) from $N_1$ to $N_2$, where $N_1$ and $N_2$ are unique to each SNP site, and $\lambda_{N1\#}$: mutation probability from $N_1$ to any of the 3 nucleotide non-$N_1$ nucleotides.

The transition diagram among the 4 nucleotide of a SNP site is shown in FIG. 2C. Based on this, the implementations obtain the following equations for converting from true allele fractions $p_1$, $p_2$ to observed allele fractions $p_1'$, $p_2'$, and $p_0'$:

$$p_1' = p_1 - p_1 \cdot \lambda_{N1\#} + p_2 \cdot \lambda_{N2N1}$$

$$p_2' = p_2 - p_2 \cdot \lambda_{N2\#} + p_1 \cdot \lambda_{N1N2}$$

$$p_0' = p_1 \cdot (\lambda_{N1\#} - \lambda_{N1N2}) + p_2 \cdot (\lambda_{N2\#} - \lambda_{N2N1}).$$

When the implementations assume uniform sequencing error rate that is independent to the nucleotide identity, the implementations have, $$p_1' = p_1 \cdot (1 - 3 \cdot \lambda) + p_2 \cdot \lambda$$

$$p_2' = p_2 \cdot (1 - 3 \cdot \lambda) + p_1 \cdot \lambda$$

$$p_0' = 2\lambda.$$

When the implementations ignore the unexpected alleles $$p_1' = (p_1 \cdot (1 - 3 \cdot \lambda) + p_2 \cdot \lambda)/(1 - 2\lambda)$$

$$p_2' = (p_2 \cdot (1 - 3 \cdot \lambda) + p_1 \cdot \lambda)/(1 - 2\lambda),$$

with $o(\lambda^2)$ approximation error, this is rewritten as $$p_1' = p_1 \cdot (1 - \lambda) + p_2 \cdot \lambda$$

$$p_2' = p_2 \cdot (1 - \lambda) + p_1 \cdot \lambda$$

Depending on the genotypes of the contributors, the formula linking contributor fraction $\beta$ with the observed allele fraction p1' is then listed in Table 3.

TABLE 3

Expected probability $\pi_1(g_{11}, g_{21}, \lambda, \beta)$ and $\pi_2(g_{11}, g_{21}, \lambda, \beta)$ of observing alleles 1 and 2 after considering sequencing errors, conditioned on each donor/recipient genotype combination. Here it is assumed that $\lambda_{N1N2} = \lambda$ for all $N_1$ and $N_2$. Since mutation rate $\lambda$ is small, a first order approximation is used.

| $g_{11}$ | $g_{21}$ | $p_1'$ | $p_2'$ |
|---|---|---|---|
| 0 | 0 | $\lambda$ | $1 - \lambda$ |
| 0 | 1 | $\beta/2 + \lambda - \beta\lambda$ | $1 - \beta/2 - \lambda + \beta\lambda$ |
| 0 | 2 | $\beta + \lambda - 2\beta\lambda$ | $1 - \beta - \lambda + 2\beta\lambda$ |
| 1 | 0 | $(1-\beta)/2 + \beta\lambda$ | $(1 + \beta)/2 - \beta\lambda$ |
| 1 | 1 | $1/2$ | $1/2$ |
| 1 | 2 | $(1 + \beta)/2 - \beta\lambda$ | $(1 - \beta)/2 + \beta\lambda$ |
| 2 | 0 | $1 - \beta - \lambda + 2\beta\lambda$ | $\beta + \lambda - 2\beta\lambda$ |
| 2 | 1 | $1 - \beta/2 - \lambda + \beta\lambda$ | $\beta/2 + \lambda - \beta\lambda$ |
| 2 | 2 | $1 - \lambda$ | $\lambda$ |

Overview of the DNA Extraction, PCR (Amplification), and Sequencing Models

Three probabilistic models (FIG. 1C) are provided to model the three major components in the generic experimental pipeline (FIG. 1A): 1) DNA extraction; 2) DNA amplification (e.g., PCR) as an approach for enriching target DNA; 3) sequencing (e.g., NGS sequencing).

The following notations are used in the mathematical models detailed in Table 4.

$p_1$, $p_{1i}$: allele 1 probability for locus i. Note that the subscript i is omitted when the implementations are focused on a single locus.

$p_1$, $p_{2i}$: allele 2 probability for locus i $n_1$, $n_{1i}$, $n_2$, $n_{2i}$: allele 1 and allele 2 read counts for locus i $n$, $n_i = n_{1i} + n_{2i}$: the total read count of the two known alleles for locus i $g_{11}$, $g_{12}$, $g_{11i}$, $g_{12i}$: recipient genotype, i.e. copies of allele 1 and 2 in the recipient genome $g_{21}$, $g_{22}$, $g_{21i}$, $g_{22i}$: donor genotype, i.e. copies of allele 1 and 2 in the donor genome B( ): beta function Beta( ), BN( ), Pois( ) Gamma( ): beta distribution, binomial distribution, and Poisson distribution, and Gamma distribution N: number of cells that supplied the DNA in the sample $\beta$: donor DNA fraction defined as the percentage of DNA that is of the donor origin in the sample.

$n_r = N \cdot (1 - \beta)$, $n_d = N \cdot \beta$: number of recipient and donor cells that supplied the DNA in the sample

TABLE 4

Statistical models for the three major components in the generic experimental pipeline. The model for each component is conditioned on the previous component. The models are per each locus.

| | | |
|---|---|---|
| gDNA or cfDNA extracted from a blood sample | Copies of allele 1: $n_1'' \sim \text{Pois}(c \cdot p_1)$ | Copies of allele 2: $n_2'' \sim \text{Pois}(c \cdot p_2)$ |
| | Copies of allele 1 given the total copipies of the locus: $n_1'' \| n'' \sim \text{BN}(n'', p_1)$, where $n'' = n_1'' + n_2''$. | |
| PCR amplified DNA | Copies of allele 1: $n_1' \sim \text{Gamma}(n_1'' \cdot \rho, \theta)$ | Copies of allele 2: $n_2' \sim \text{Gamma}(n_2'' \cdot \rho, \theta)$ |
| | Fraction of allele 1 of the locus in the PCR product, conditioning on allele 1 and allele 2 copies in the extracted DNA: $n_1'/n' \| n_1'', n_2'' \sim \text{Beta}(n_1'' \cdot \rho, n_2'' \cdot \rho)$, where $n' = n_1' + n_2'$. Ignoring DNA sampling variation (hence $n_1'' = n'' \cdot p_1$, $n_2'' = n'' \cdot p_2$): $n_1'/n' \sim \text{Beta}(n'' \cdot \rho \cdot p_1, n'' \cdot \rho \cdot p_2)$ | |
| Copies of sequenced reads mapped to the loci (without sequencing error) | Copies of allele 1 given the total copies of the locus, conditioning on fraction of allele 1 of a locus in the PCR product: $n_1 \| n, n_1'/n' \sim \text{BN}(n, p = n_1'/n')$, where $n = n_1 + n_2$. | |

DNA Extraction Model

When cfDNA or cellular DNA is extracted from a blood sample, the obtained DNA is a small sample from the large pool of DNA, and hence the implementations model the counts of two alleles at each locus as two Poisson distributions. Hence the DNA copy ($n_1''$) for allele 1 at a locus conditioned on the total counts $n''$ follows the binomial distribution: $n_1'' \sim BN(n'', p_1)$, with mean $\mu_0 = n'' \cdot p_1$ and variance $\delta_0^2 = n'' \cdot p_1 \cdot p_2$. When donor fraction $\beta < 0.2$, $\delta^2 \approx \mu_0$.

When gDNA is extracted from a sample, the resulting gDNA amount for each locus can again be variable due to extraction losses. Viewing $p_1$ as the fraction of allele 1 in the input sample, the amount of allele 1 in the extracted DNA can again be modeled by a binomial distribution: $n_1'' \sim BN(n'', p_1)$.

PCR Amplification Model

We model the PCR amplification process as a stochastic process in order to obtain a probabilistic distribution of allele 1 counts in the PCR product. Let $x_t$ be the DNA copies of a given allele after cycle t of PCR amplification, let rt be the amplification rate for cycle t, and let $y_t$ be the new copies generated at cycle t. By assuming each piece of DNA has a probability $r_t$ of getting amplified and added to the DNA pool, the implementations have the following model for amplification:

$x_{t+1} = x_t + y_{t+1}$, where $y_{t+1} \sim BN(x_t, r_{t+1})$ follows a binomial distribution with $x_t$ and $r_{t+1}$ as parameters.

Based on this model, the implementations claim that the DNA copy number for a locus in the PCR product follows the Gamma distribution approximately. Below is provide the justification.

Step 1: Using Yule process (a continuous time stochastic process) to approximate PCR (a discrete time stochastic process).

The PCR process $x_{t+1} = x_t + y_{t+1}$, where $y_{t+1} \sim BN(x_t, r_{t+1})$ is a discrete time pure-birth process: in a given cycle of time t, each copy of DNA "gives birth" independently at some rate rt. The continuous time version of the pure-birth process is well-known as the Yule-Furry Process. For the continuous time birth process, the final copy number for a locus at a given time t is known to follow a negative binomial distribution. The implementations can use the same distribution to approximate the discrete time birth process, when the number of PCR cycles is not close to 1.

Step 2: Using Gamma distribution (a continuous distribution) to approximate negative binomial distribution (a discrete distribution).

A negative binomial random variable (r.v.) can be written as a sum of i.i.d. geometric r.v.s. The exponential distribution is known to be the continuous version of the geometric distribution. Hence, the sum of i.i.d. exponential r.v.s, which follows the Gamma distribution, is the continuous version of the sum of binomial r.v.s, which is negative binomial.

Below the implementations estimate the parameters of the Gamma distributions of the allele counts in the PCR products.

Based on the law of total variance $\text{var}(x_{t+1}) = \text{var}(E(x_{t+1}|x_t)) + E(\text{var}(x_{t+1}|x_t))$, the implementations can derive the mean and variance of $x_t$ as follows:

$$\mu_{t+1} = \mu_t \cdot (1 + r_{t+1})$$

$$\delta_{t+1}^2 = \mu_t \cdot r_{t+1} \cdot (1 - r_{t+1}) + \delta_t^2 \cdot (1 + r_{t+1})^2,$$

where $\mu_t = E(x_t)$, $\delta_t^2 = \text{var}(x_t)$.

Assuming an average amplification rate per PCR cycle $r_{t-1} = r$, the implementations have $$\mu_t = \mu_0 \cdot (1 + r)^t$$

$$\delta_t^2 = \mu_0 \cdot (1+r)^t \cdot [(1+r)^t - 1] \cdot (1-r)/(1+r) + \delta_0^2 \cdot (1+r)^{2t}$$

Notice that $\mu_0$ and $\delta_0^2$ are the mean and variance of DNA allele counts in the PCR amplification input, and they can be computed based on the DNA extraction model described above. Alternatively, if the implementations do not treat cfDNA/cellular DNA allele counts as random variables, the implementations have $\mu_0 = n_1''$ or $n_2''$, and $\delta_0^2 = 0$.

The corresponding gamma distribution $G(x_t|k, \theta) = x^{k-1} e^{-x/\theta} / [\theta^k \cdot \Gamma(k)]$ that matches this mean and variance has parameters:

$$\theta = [(1+r)^t - 1] \cdot (1-r)/(1+r) + \delta_0^2 / \mu_0 \cdot (1+r)^t$$

$$k = \mu_0 \cdot (1+r)^t / [[(1+r)^t - 1] \cdot (1-r)/(1+r) + \delta_0^2 / \mu_0 \cdot (1+r)^t].$$

For a given locus with two alleles and two initial copies ($n_1''$, $n_2''$), assuming identical amplification rate $r_1 = r_2 = r$ for two alleles for each locus, the two corresponding gamma distributions $G(n_1'|k_1, \theta_1)$ and $G(n_2'|k_2, \eta_2)$ have the following parameters:

$$\theta_1 = [(1+r)^t - 1] \cdot (1-r)/(1+r) + p_2 \cdot (1+r)^t$$

$$\theta_2 = [(1+r)^t - 1] \cdot (1-r)/(1+r) + p_1 \cdot (1+r)^t$$

$$k_1 = n'' p_1 / [[1 - (1+r)^{-t}] \cdot (1-r)/(1+r) + p_2]$$

$$k_2 = n'' p_2 / [[1 - (1+r)^{-t}] \cdot (1-r)/(1+r) + p_1].$$

When the implementations condition the PCR model on the DNA extraction model, s.t. $\mu_0 = n_1''$ or $n_2''$ and $\delta_0^2 = 0$, the implementations then have $$\theta_1 = [(1+r)^t - 1] \cdot (1-r)/(1+r)$$

$$\theta_2 = [(1+r)^t - 1] \cdot (1-r)/(1+r)$$

$$k_1 = n_1'' \cdot (1-r)/(1+r) / [1 - (1+r)^{-t}]$$

$$k_2 = n_2'' \cdot (1-r)/(1+r) / [1 - (1+r)^{-t}].$$

Hence the allele copies $n_1'$ and $n_2'$ in the PCR product follow two Gamma distributions with identical scale parameters $\theta_1$ and $\theta_2$, which are only dependent on the PCR process (the number of cycles and amplification rate). Therefore, $$n_1'/(n_1' + n_2') \sim \text{Beta}(n_1'' \cdot \rho, n_2'' \cdot \rho),$$

where $\rho = (1+r)/(1-r)/[1-(1+r)^{-t}]$, or approximately $\rho = (1+r)/(1-r)$ when the number of cycles t is large, is a constant related to the amplification rate r, which is only dependent on the PCR process. For a specific locus, this is written as $n_{i1}'/(n_{i1}' + n_{i2}') \sim \text{Beta}(n_{i1}'' \cdot \rho_i, n_{i2}'' \cdot \rho_i)$, to capture the loci specific PCR amplification rate.

If the implementations ignore DNA sampling and assume all loci have the same total DNA copy number $n_i'' = n''$, then $n_{i1}'' = n'' \cdot \rho_i \cdot p_{i1}$ and $n_{i2}'' = n'' \cdot \rho_i \cdot p_{i2}$. The allele fraction for a locus in the PCR product follows:

$$n_{i1}'/(n_{i1}' + n_{i2}') \sim \text{Beta}(n'' \cdot \rho_i \cdot p_{i1}, n'' \cdot \rho_i \cdot p_{i2}).$$

Note that without the Gamma distribution approximation, the implementations have $n_1' \sim NB(r_1, p)$ and $n_2' \sim NB(r_2, p)$, and the ratio $n_1'/(n_1' + n_2')$ has no closed form distribution. With the Gamma distribution approximation, $n_1' \sim \text{Gamma}(n_1'' \cdot \rho, \theta)$ and $n_2' \sim \text{Gamma}(n_2'' \cdot \rho, \theta)$, and $n_1'/(n_1' + n_2')$ follows the beta distribution.

Sequencing Model for Read Counts

NGS sequencing is a process that samples from the pool of DNA molecules supplied to the sequencer and reads out the sequences of these molecules. The fraction of allele 1 for a locus i in the PCR product is $n_{i1}'/(n_{i1}' + n_{i2}')$. This fraction determines the probability that allele 1 reads occur in the sequencing results. Conditioning on $n_i$ the total number of reads per locus, the distribution of $n_{i1}$, the allele 1 read count of a locus, is then modeled as a binomial distribution $n_{i1} \sim BN(n_i, n_1'/(n_1'+n_2'))$.

Modeling the Genetic Relatedness between the Contributors as a Prior Distribution If the contributor (donor/recipient) genotypes are completely known, they can be directly incorporated (using Table 2 or Table 3) as parameters of the component models described above. However, when the genotypes are unknown, the implementations can make use of the genetic-relationship information between the donor and recipient, which is often available in clinical applications.

We formulate different types of donor-recipient relationships as distinct prior distributions on the space of possible genotype combinations of the donor and recipient. Assuming Hardy-Weinberg equilibrium, the genotype distribution for a single individual is $P(g_{Mother}=[0,1,2])=[(1-\pi)^2, 2\pi(1-\pi), \pi^2]$, assuming the population frequency of allele 2 to be $\pi$. Notice that all genetic relatednesses are the results of parent-child relationships. Based on the genetic-relationships between parent and child for a give biallelic marker site (Table 5), the implementations can compute the joint distribution for any genetic relationship.

TABLE 5

Probability distribution of child genotype given parents' genotypes for a given locus, as well as the joint distribution between father and mother assuming they are not relatives.

| $g_{Father}$ | $g_{Mother}$ | Child probability for genotype [0, 1, 2] respectively | $P(g_{Father}, g_{Mother})$ |
|---|---|---|---|
| 0 | 0 | [1, 0, 0] | $(1-\pi)^4$ |
| 0 | 1 | [1/2, 1/2, 0] | $2\pi(1-\pi)^3$ |
| 0 | 2 | [0, 1, 0] | $\pi^2(1-\pi)^2$ |
| 1 | 0 | [1/2, 1/2, 0] | $2\pi(1-\pi)^3$ |
| 1 | 1 | [1/4, 1/2, 1/4] | $4\pi^2(1-\pi)^2$ |
| 1 | 2 | [0, 1/2, 1/2] | $2\pi^3(1-\pi)$ |
| 2 | 0 | [0, 1, 0] | $\pi^2(1-\pi)^2$ |
| 2 | 1 | [0, 1/2, 1/2] | $2\pi^3(1-\pi)$ |
| 2 | 2 | [0, 0, 1] | $\pi^4$ |

Below are the prior distributions for the following types of genetic-relationship: parent-child, child-parent, siblings, uncle/aunt-nephew, nephew-uncle/aunt, and unrelated.

Joint Distribution between Father and Child Genotypes

As an example, the Father-Child donor-recipient genotype (GT) joint distribution is computed using the following formula:

$P$(Recipient=Me GT, Donor=Father GT)=
$\Sigma_{mother\ GT}[P$(Me GT|Father GT, Mother GT)$\cdot P$(Father GT, Mother GT)], where values of $P$(Me GT|Father GT, Mother GT) and $P$(Father GT, Mother GT) are taken from the Table 5 columns 3 and 4 respectively.

Joint Distribution between Sibling Genotypes

As a example, the Me-Sibling donor-recipient genotype joint distribution is computed using the following formula, based on the conditional independence of two sibling genotypes given parents genomes:

$P$(Recipient=Me GT, Donor=Sibling GT)=
$\Sigma_{mother\ GT}\Sigma_{father\ GT}[P$(Me GT|Father GT, Mother GT)$\cdot P$(Sibling GT|Father GT, Mother GT)$\cdot P$(Father GT, Mother GT)], Where values of $P$(Me GT|Father GT, Mother GT), $P$(Sibling GT|Father GT, Mother GT), and $P$(Father GT, Mother GT) are taken from the Table 5 columns 3, column 3, and column 4 respectively.

Joint Distribution Between Uncle-Nephew Genotypes

As a example, the Uncle/Aunt-Nephew/Niece donor-recipient genotype joint distribution is computed using the following formula:

$P$(Recipient=Me GT, Donor=Uncle GT)

=$\Sigma_{grand\ mother\ GT}\Sigma_{grand\ father\ GT}\Sigma_{mother\ GT}\Sigma_{father\ GT}[P$(Me GT|Father GT, Mother GT)$\cdot P$(Mother GT)$\cdot P$(Father GT|GrandFather GT, GrandMother GT)$\cdot P$(Uncle GT|GrandFather, GrandMother GT)$\cdot P$(GrandFather GT, GrandMother GT)]

=$\Sigma_{mother\ GT}\Sigma_{father\ GT}P$(Me GT|Father GT, Mother GT)$\cdot P$(Mother GT)$\cdot P$(Father GT, Uncle GT), where values of $P$(Me GT|Father GT, Mother GT) is taken from column 3 of table 5, and $P$(Father GT, Uncle GT) is the same as $P$(Recipient=Me GT, Donor=Sibling GT).

The results from the above derivations is summarized in Table 6, and the specific instances given population SNP allele frequency value $\pi=0.5$ is provided in Table 7. Additional relationships, such as grandparent-grandchild, grandchild-grandparent, half-siblings, and cousins, can be derived based on the same underlying principle.

TABLE 6

Prior distributions $P(g_{11}, g_{21})$ of related or unrelated genomes. Assuming 1) all SNPs are from autosomes, 2) All married couples are genetically-unrelated, g11 is the recipient genome, g21 is the donor genome.

| | | Donor's relationship to Recipient | | | |
|---|---|---|---|---|---|
| $g_{11}$ | $g_{21}$ | Parent or Child | Sibling | Uncle/Aunt or Nephew/Niece | Unrelated |
| 0 | 0 | $(1-\pi)^3$ | $(1-\pi)^2(1-\pi/2)^2$ | $(1-\pi)^3(1-\pi/2)$ | $(1-\pi)^4$ |
| 0 | 1 | $\pi(1-\pi)^2$ | $\pi(1-\pi)^2(1-\pi/2)$ | $\pi(1-\pi)^2(3/2-\pi)$ | $2\pi(1-\pi)^3$ |
| 0 | 2 | 0 | $\pi^2(1-\pi)^2/4$ | $\pi^2(1-\pi)^2/2$ | $\pi^2(1-\pi)^2$ |
| 1 | 0 | $\pi(1-\pi)^2$ | $\pi(1-\pi)^2(1-\pi/2)$ | $\pi(1-\pi)^2(3/2-\pi)$ | $2\pi(1-\pi)^3$ |
| 1 | 1 | $\pi(1-\pi)$ | $\pi(1-\pi)[1+\pi-\pi^2)]$ | $\pi(1-\pi)[1/2+2\pi-2\pi^2]$ | $4\pi^2(1-\pi)^2$ |
| 1 | 2 | $\pi^2(1-\pi)$ | $\pi^2(1-\pi)(1/2+\pi/2)$ | $\pi^2(1-\pi)(1/2+\pi)$ | $2\pi^3(1-\pi)$ |
| 2 | 0 | 0 | $\pi^2(1-\pi)^2/4$ | $\pi^2(1-\pi)^2/2$ | $\pi^2(1-\pi)^2$ |
| 2 | 1 | $\pi^2(1-\pi)$ | $\pi^2(1-\pi)(1/2+\pi/2)$ | $\pi^2(1-\pi)(1/2+\pi)$ | $2\pi^3(1-\pi)$ |
| 2 | 2 | $\pi^3$ | $\pi^2(1/2+\pi/2)^2$ | $\pi^3(1/2+C/2)$ | $\pi^4$ |

TABLE 7

Distributions P($g_{11}$, $g_{21}$) of related or unrelated genomes
when SNP population prior π = 0.5. Assuming 1)
all SNPs are from autosomes, 2) All couples are genetically-unrelated.

| | | Donor's relationship to Recipient | | | |
|---|---|---|---|---|---|
| $g_{11}$ | $g_{21}$ | Parent or Child | Sibling | Uncle/Aunt or Nephew/Niece | Unrelated |
| 0 | 0 | 8/64 | 9/64 | 6/64 | 4/64 |
| 0 | 1 | 8/64 | 6/64 | 8/64 | 8/64 |
| 0 | 2 | 0 | 1/64 | 2/64 | 4/64 |
| 1 | 0 | 8/64 | 6/64 | 8/64 | 8/64 |
| 1 | 1 | 16/64 | 20/64 | 16/64 | 16/64 |
| 1 | 2 | 8/64 | 6/64 | 8/64 | 8/64 |
| 2 | 0 | 0 | 1/64 | 2/64 | 4/64 |
| 2 | 1 | 8/64 | 6/64 | 8/64 | 8/64 |
| 2 | 2 | 8/64 | 9/64 | 6/64 | 4/64 |

Notice that the distributions for Parent/Child, siblings are quite different from unrelated, while uncle/aunt/nephew/niece are close to unrelated. In the case when the donor genotype is unknown, the implementations can infer the genetic relationship by evaluating the likelihood function of fitted models of each of the above genetic relationships. Alternatively, the implementations can allow multiple free parameters in the genetic priors distribution (with additional constraints that the marginal distributions should follow Hardy-Weinburg equilibrium), and estimate these parameters together with the estimation of donor fraction.

Integration of the Modeling Components

The components of the probabilistic mixture model are integrated to provide a solution to the contributor DNA quantification (CDQ) problem. The population allele frequency π for each SNP site can be obtained from public databases such as dbSNP. If one selects the most informative SNPs, i.e. SNPs with π=0.5, one can set π=0.5 for all loci and let P($g_{11}$,$g_{21}$) be the genetic-relatedness prior distribution as described in the previous section.

On a schematic level, FIG. 2B shows a block diagram illustrating various components of the probabilistic mixture model 200. Some components are optional in some implementations. The probabilistic mixture model 200 includes a binomial distribution 208 for modeling allelic counts of sequencing reads. In some implementations, the probabilistic mixture model also includes a component for modeling donor-donee (or recipient) relationship using a genetic relatedness prior distribution 202. In some implementations, the probabilistic mixture model also includes a binomial distribution 204 for modeling DNA extraction allelic counts. In some implementations, the probabilistic mixture model 200 also includes a beta distribution 206 for modeling PCR product or amplification product allelic fraction. See block 206.

In some implementations, the mixture model combines the binomial distribution 208 with binomial distribution 204 to model both the DNA extraction errors and sequencing errors. In such implementations, the mixture model uses a binomial distribution 210 to model the allelic counts of sequencing reads, which allelic counts of sequencing reads depend on the allelic counts of DNA extraction.

In some implementations, the probabilistic mixture model 200 combines beta distribution 206 and binomial distribution 208, and uses a beta-binomial distribution 212 to model both errors in the PCR or amplification process and errors of sequencing process.

In some implementations, the probabilistic mixture model 200 combines binomial distribution 204, beta distribution 206, and binomial distribution 208 to account for variance resulting from DNA extraction, amplification process, and sequencing process, respectively. In such implementations, probabilistic mixture model 200 first uses a beta distribution 214 to approximate the effects of binomial distribution 204 and beta distribution 206. The probabilistic mixture model 200 then combines beta distribution 214 and binomial distribution 208 using beta-binomial distribution 216.

The Seq Model

A basic version of the full model ignores the DNA extraction model and the PCR model, and only considers the sequencing model. For each locus, the sequencing read count for the reference allele is modeled by a binomial distribution (FIG. 1C), $n_{i1}$~BN($n_{i1}$, $p_{i1}$), where the value of parameter $p_{i1}$($g_{11}$, $g_{21}$, λ, β) is a function on the donor-recipient genotype combination for the loci (Table 2 and Table 3). Given that the genotypes are unknown, the implementations marginalize over the 9 possible genotype combinations for each locus with P($g_{11}$,$g_{21}$|π) as prior distribution (Table 6 and Table 7). The complete likelihood function across all loci is the product of the marginal distributions for all loci:

L($n_1$, $n_2$|β, π)=$\Pi_i$ $\Sigma_{g_{11}g_{21}}$ BN($n_{i1}$, $p_{i1}$($g_{11}$, $g_{21}$, λ, β))·P($g_{11}$, $g_{21}$|π), where π is a known parameters, and β is the donor DNA fraction.

The Extraction-Seq Compound Model

A more advanced model combines the DNA extraction model as well as the Sequencing model. The implementations ignore the PCR step (i.e. assume that, for each locus, the allele fraction in the PCR product is the same as the allele fraction in the DNA sample), and only model DNA sampling and sequencing steps For each locus, there is a binomial distribution for the allele counts in the input DNA sample. This captures the locus-to-locus variability of the allele fractions in the input DNA provided to the NGS sequencing.

For the DNA extraction model, the implementations have $n_{i1}$"~BN(n", $p_{i1}$), while conditioning on the DNA extraction model, the sequencing model is $n_{i1}$|$n_{i1}$", $n_i$"~BN($n_i$, $n_{i1}$"/$n_i$"), where $n_i$"=n" is the copies of haploid genomes the input DNA correspond to. Unfortunately, the marginal distribution of nu has no closed form formula. the implementations choose to approximate the distribution of $n_{i1}$"/n" with a beta distribution Beta(a, b), and the best Beta distribution is selected by matching the mean and variance of $n_{i1}$"/n" with those derived from the binomial model $n_{i1}$"~BN(n", $p_{i1}$):

$p_{i1}$=a/(a+b)

$p_{i1}$·(1−$p_{i1}$)/n"=ab/(a+b)²/(a+b+1).

Solving the equations gives the beta distribution Beta((n"−1)$p_{i1}$, (n"−1)$p_{i2}$) as the best approximation. With this approximation to the DNA extraction model, the marginal distribution of nu then follows a beta-binomial distribution of the form:

BB($n_{i1}$,$n_{i2}$|$n_i$,(n"−1)·$p_1$($g_{11}$,$g_{21}$,λ,β),
(n"−1)·$p_2$($g_{11}$,$g_{21}$,λ,β).

The corresponding full likelihood function considering the genetic-relatedness prior is then:

L($n_1$,$n_2$|β,n",λ,π)=$\Pi_i\Sigma_{g_{11}g_{21}}$BB($n_{i1}$,$n_{i2}$|$n_i$,(n"−1)·$p_1$($g_{11}$,$g_{21}$,λ,β),(n"−1)·$p_2$($g_{11}$,$g_{21}$,λ,⊕))·
P($g_{11}$,$g_{21}$|π).

Notice that both n" and π=0.5 are known parameters, and the final full likelihood function has only a single unknown parameter β, the donor DNA fraction.

The input DNA (haploid) copy numbers n" can be derived from the input DNA mass. When input DNA amount is 8 ng, n"=8 ng/[3.59×10⁻³ ng/copy]=2228.412.

PCR-Seq Compound Model

Ignoring the DNA extraction model, and assuming a known genotype combination for a given locus, then the PCR model: $n_{i1}'/(n_{i1}'+n_{i2}') \sim \text{Beta}(n" \cdot \rho_i \cdot p_{i1}, n" \cdot n \cdot \rho_i \cdot p_{i2})$ and Sequencing model $n_{i1} \sim BN(n_i, n_1'/(n_1'+n_2'))$ can be combined into the beta-binomial distribution: $BB(n_{i1}, n_{i2}|n_i n" \cdot \rho_i \cdot p_{i1}, n" \cdot \rho_i \cdot p_{i2})$. Notice that both the underlying loci specific PCR amplification rates $\rho_i$ are unknown. If the implementations assume all loci have the same inherent amplification rate, then the implementations have, $BB(n_{i1}, n_{i2}|n_i, c \cdot p_{i1}(g_{11}, g_{21}, \beta), c \cdot p_{i2}(g_{11}, g_{21}, \beta))$.

The complete likelihood model across all loci is then: $L(n_1, n_2|\beta, c, \pi) = \Pi_i \Sigma_{g11g21}[BB(n_{i1}, n_{i2}|n_i, c \cdot p_1(g_{11}, g21, \lambda, \beta), c \cdot p_2(g_{11}, g21, \lambda, \beta)) \cdot P(g_{11}, g_{21}|\pi)]$, where c and β are two parameters to be estimated.

Alternatively, the implementations can define the relative amplification rate of each locus to be proportional to the total reads per locus, and re-parameterize the beta-binomial as $BB(n_{i1}, n_{i2}|n_i, c' \cdot n_i \cdot p_{i1}(g_{11}, g_{21}, \beta), c' \cdot n_i \cdot p_{i2}(g_{11}, g_{21}, \beta))$.

The complete likelihood model across all loci is then: $L(n_1, n_2|\beta, c', \pi) = \Pi_i \Sigma_{g11g21}[BB(n_{i1}, n_{i2}|n_i, c' \cdot n_i p_1(g_{11}, g21, \lambda, \beta), c' \cdot n_i \cdot p_2(g_{11}, g21, \lambda, \beta)) \cdot P(g_{11}, g_{12}|\pi)]$, where c and β are two parameters to be estimated Extraction-PCR-Seq Compound Model All three components in the Extraction-PCR-sequencing generic experimental pipeline can be modeled together by a beta-binomial if the implementations combine DNA extraction and PCR models into one model and approximate it by a single beta distribution. Intuitively, although the expected value of allele 1 fraction in the PCR product ($n_1'/n'$, see Table 4) remains $p_1$, the uncertainty (variance) of $n_1'/n'$ originates from both the DNA extraction and the PCR steps. To obtain a beta distribution beta(a,b) to model DNA extraction and PCR together, the implementations compute the unconditional mean and variance of $n_{i1}'/n'$ based on the following laws: $E(n_{i1}'/n') = E(E(n_{i1}'/n"))$, and $\text{var}(n_{i1}'/n') = \text{var}(E(n_{i1}'n_i'|n_{i1}"/n")) + E(\text{var}(n_{i1}'n_i'/n_i'|n_{i1}"/n'))$. This gives: $E(n_{i1}'/n') = p_{i1}$, and $\text{var}(n_{i1}'/n') = p_{i1}p_{i2}/n" + p_{i1}p_{i2}/(n" \cdot \rho_i \cdot 1) - p_1 p_2/[n" \cdot (n" \cdot \rho_i+1)]$, where $\rho_i = (1+r_i)/(1-r_i) > 1$ is the constant related to the amplification rate $r_i$. Since n" is large, the implementations have the following approximation $\text{var}(n_{i1}'/n') = p_{i1}p_{i2}/[n" \cdot (1+r_i)/2]$. The best beta distribution that models DNA extraction and PCR is then $\text{Beta}([n" \cdot (1+r_i)/2-1]p_{i1}, [n" \cdot (1+r_i)/2-1]p_{i2})$. Notice this is close to the beta distribution for cfDNA/gDNA extraction $\text{Beta}((n"-1)p_{i1}, (n"-1)p_{i2})$, yet the variance is now larger. For a typical PCR reaction with $r_i = 0.8$ to 0.95, the implementations have $n" \cdot (1+r_i)/2 = 0.9 \cdot n"$ to $0.975 \cdot n"$.

The full likelihood function for cfDNA-PCR-Seq model is:

$$L(n_1,n_2|\beta,n",\pi) = \Pi_i \Sigma_{g11g21} BB(n_{i1},n_{i2}|n_i,(n" \cdot (1+r_i)/2-1) \cdot p_1(g_{11},g21,\lambda,\beta),(n" \cdot (1+r_i)/2-1) \cdot p_2(g_{11},g21,\lambda,\beta)) \cdot P(g_{11},g_{21}|\pi).$$

Algorithm for Estimating Contributor Nucleic Acid Fractions and their Confidence Intervals Numerical Optimization for Estimating Contributor DNA Fractions The contributor DNA fraction β is estimated as the value that maximize the full likelihood function $L(n_1, n_2|\beta)$. As mentioned above, although DNA is referred to in this and other examples, RNA and other nucleic acid molecules may be processed and analyzed similarly. Also, although the examples refer to nucleic acid mixture samples, the sample may include only a single contributor's nucleic acid, in which case the contributor fraction would be estimated as 1 or within a margin of error from 1. During the calculation of $L(n_1, n_2|\beta)$, multiple small probabilities values are multiplied. To avoid numerical underflowing when multiplying small probabilities, the implementations perform all summation and multiplications on log scale. The sum of small probability on log scale is performed as following. 1) obtain the max of the log probabilities as $x_{max}$; 2) subtract all the log probabilities by the max; 3) exponentiate and then sum the resulting values; 4) log transform the resulting sum; 5) add back the max of the log probabilities. $\log(\exp(x_1-x_{max}) + \exp(x_2-x_{max}) + \ldots + \exp(x_n-x_{max})) + x_{max}$.

To avoid negative values, the transformation $\beta = 1/(1+e^{-\eta})$ is used, and to avoid local minima, the full likelihood function is initialized with $\beta_0 = 1/(1+e^{-\eta_0})$, where $\eta_0$ is the value among $-10, -9.9, -9.8, \ldots, -0.1, 0$ that maximizes $L(n_1, n_2|1/(1+e^{-\eta_0}))$. Further numerical optimization of η is performed optimization using BFGS-quasi-Newton method is used to minimize $-\log 2(L)$.

Estimate the Confidence Interval

The lower bound of the confidence interval of the estimates are determined based on the Cramer-Rao inequality: $\text{var}(\theta_{ML}) \geq 1/I(\theta_{ML})$, where $\theta_{ML}$ is the maximum likelihood estimate of parameter θ, and $I(\theta_{ML})$ is fisher's information at $\theta_{ML}$. Based on this, one can estimate the variance of β and c in the above described likelihood functions. The standard error is estimated as sqrt(1/H) following the Cramér-Rao bound, where H is the Hessian matrix which can be approximated and is estimated in the BFGS-quasi-Newton method.

We use the following reparameterizations during the numerical optimization to estimate β and c, $$\beta = 1/(1+e^{-\eta}),$$

$$c = e^\kappa.$$

Let $I(\eta)$ and $I(\kappa)$ be the Fisher's information under parameterization η and κ, then the Fisher's information of the original parameters are $$I(\beta) = I(\eta)(1/(\beta(1-\beta))^2$$

$$I(c) = I(k)(1/c)^2.$$

Hence the implementations have the following transformation for estimated stand deviations, $$\text{std}(\beta) = \text{std}(\eta) \cdot \beta \cdot (1-\beta)$$

$$\text{std}(\beta) = \text{std}(\eta) \cdot c.$$

Forensic Application of Deconvolving Nucleic Acid Samples

Mixture deconvolution: Given the observed counts D, infer the contributor frequencies f and the per-locus genotype configurations G The following implementations are suitable for forensics applications. The processes described herein first obtain maximum likelihood estimates of f while marginalizing theta and G over their priors (described below), then calculate a posterior probability for every genotype configuration, conditioned on those estimates. The processes report the MLE of f along with a top-N list of plausible genotype configurations and associated probabilities. Genotype configurations are reported per locus (across all contributors) and also per contributor per locus. Contributor frequency f under this section corresponds to contributor fraction β described above. G denotes genotypes of contributors and corresponds to $g_{11}, g_{21}$ described above. Data D corresponds to allele counts n above.

Sample Inclusion Query: Given the Observed Counts D, an Inferred Point Estimate of f and a Query Genotype, Infer whether the Query Genotype is Present in the Sample.

Approach: the process involves calculating the prior probability $P(G_Q)$ of the query genotype being in an N-contributor sample drawn from the general population (using the known population allele frequencies) and the posterior probability $P(G_Q|D)$ of the query genotype being in the observed sample (with the other contributors drawn randomly from the population), then report the log-ratio between these two probabilities as a measure of evidence. Note that $P(G_Q|D) = P(D|G_Q)P(G_Q)/P(D)$, so that the reported evidence can also (equivalently) be described as the likelihood ratio $P(D|G_Q)/P(D|G_{random})$, because the marginal probability of the data $P(D)$ is the same thing as the probability of the data conditioned on contributors being drawn randomly from the population $P(D|G_{random})$.

Inference Approach

The core computation is a function that takes values off and theta as input and calculates, for every locus, the marginal log-probability of the data conditioned on f and theta (i.e. the log-likelihood marginalized over G) by performing a sum (weighted by genotype prior) over genotype-specific probabilities. These are then summed over the (discrete equal-weight) distribution for theta to obtain the log-likelihood marginalized over G and theta. The implementations also retain the sums (over theta) for individual values of G so that (after normalising) the implementations have posterior probabilities for every genotype at every locus, conditional on f but marginalized over theta. The per-locus marginal log-likelihoods are accumulated and returned as a single log-likelihood for the whole dataset, still conditioned on f. The implementations perform this calculation at every point in a grid of possible values for the frequency vector f and get the MLE for f by picking the grid point at which the likelihood is maximum. The frequency grid is set up at equally spaced intervals of 2.5%, plus an extra point at all frequencies equal (if not already represented), with the constraints that frequencies are listed in non-increasing order and that they sum to 1. This yields a grid of 21 points for 2 contributors or 155 points for 3 contributors (4-contributor case not yet implemented, may require a coarser grid; could also speed up 3-contributor case by using a coarser grid at first and then refining as a 2nd step after zooming in on the interesting part of the grid).

The per-locus posterior probabilities of genotype configurations, conditioned on the MLE of f, are used for mixture deconvolution queries and for sample queries.

Marginal Likelihood Calculation:

The overall log-likelihood is a sum over locus-specific log-likelihoods: log $P(D|theta,f)=\sum_l$ log $P(D_l|theta,f)$.

The locus-specific marginal likelihood is computed by summing over a large set of plausible genotype configurations: $P(D_l|theta,f)=\sum_{G_l} P(D_l|theta,f,G_l)P(G_l)$. For computational tractability, the following operations are employed.

Threshold out alleles with counts<=1. In prototype 1, for historical reasons, the implementations construct both an unpruned and a pruned list of genotype configurations. Only the unpruned list contains configurations with below-threshold alleles; some implementations only use the pruned list and even shorter (more aggressively pruned) versions described below.

Limit the genotype configurations that are considered plausible by constructing a list of "required" alleles and enumerating only those genotype configurations that contain every required allele at least once. An allele is placed on the list of required alleles if its UMI count is judged too high to be plausible via general "drop-in" N-1 stutter. The following hard thresholds are used.

An absolute threshold (count_threshold; set at 10). This is the maximum number of non-stutter UMIs the implementations are willing to explain at an allele not present in any contributor.

A relative threshold (stutter_threshold; set at 0.1). This value multiplied by the count of the potential stutter donor (see "handling stutter" below) is the maximum number of UMIs the implementations are willing to explain as N-1 stutter.

If an observed count is above the sum of the above two thresholds it is deemed real and must be present in all genotype configurations. If not, it may be omitted (leaving a larger number of genotype configurations to consider).

Construct an aggressively pruned list for use in the more computationally demanding parts (i.e. when inferring contributor frequencies but not for the final deconvolution step):

For each configuration:
  for each contributor frequency vector, the implementations compare the expected number of reads per allele with the observed number and calculate the RMSE over alleles
  this calculation takes stutter into account, but is much cheaper than the full likelihood calculation
  use the minimum RMSE over frequency vectors (is there a frequency vector for which the configuration is plausible?). For the "best RMSE" (see below) the implementations use the average over frequency vectors (breaks if using the best-fitting frequency vector, which may be a completely unrealistic one given the dataset as a whole).
  retain the configuration if observation is close enough to expectation according to both of the following criteria:
  absolute threshold (0.2): prune out configurations for which RMSE is more than this fraction of the largest read count
  relative threshold (5): prune out configurations for which RMSE is more than this factor from the "best RMSE" (see above)

The sets of plausible genotype configurations, along with their priors P(a) (see below), is constructed during preprocessing and reused every time a likelihood calculation is called.

Genotype-Specific Likelihood

The generative model stipulates a fixed number of potentially detectable molecules per locus in the "original" sample (which might correspond to the physical sample collected from the crime scene or at a later stage during processing). The implementations assume that these molecules are divided up per allele in proportion to the contributor frequencies of the contributors to which those alleles have been assigned in the genotype configuration. Each of these molecules is then either detected or not, so that the number of molecules detected for a given allele is governed by a binomial process. The detection probability (i.e. the binomial parameter) may vary from allele to allele (and from locus to locus) and at every locus the implementations assign a beta prior governed by two parameters:

mean (the average detection probability)

The coverage (total number of UMIs detected) varies from locus to locus. In principle this means that the mean of the beta distribution should vary from locus to locus. Some implementations keep the mean fixed across loci and instead allow the number of molecules in the sample to vary from locus to locus. This should come to the same thing (since the two parameters are expected to be highly correlated, treating them as separate parameters would make them mostly unidentifiable). The mean parameter is hardcoded to a value of 0.1; the total number of molecules is set by extrapolating from the observed coverage, taking account of this mean parameter as well as the stutter rate (see below).

concentration parameter (how much the detection probability varies from allele to allele: this is closely related but not identical to allele balance as measured in the lab)

This parameter varies from locus to locus and is assigned a 3-component discrete prior (shared across loci), representing low- medium- and high-noise conditions.

The other noise parameters are:

stutter_prob: for each of the total number of molecules as extrapolated above (allele N), the generative model stipulates that it will generate a UMI (allele N−1) with probability stutter_prob.

This parameter is shared between alleles at the same locus but varies from locus to locus. It is assigned a 3-component discrete prior (shared across loci), representing low- medium- and high-noise conditions.

expected_dropin: this is the expected number of spurious UMIs (not generated by either the molecules of that allele or of the stutter donor) observed at at an allele. The parameter is hardcoded (not inferred) and shared across alleles and loci.

Given the noise parameters above (which comprise $theta_1$), the genotype-specific likelihood $P(D_1|theta_1,f,G_1)$ is then calculated as a product of allele-specific likelihoods.

During likelihood calculation for a locus some implementations try many genotype configurations, some of which only differ from each other at a few alleles. As a result, allele-specific likelihoods are often required for exactly the same counts that have been used before. The implementations store the result of every allele-specific likelihood calculation in a lookup table and only compute likelihoods if they are not already in the table.

We support two allele-specific likelihood calculations: a simple (faster) stutter-free calculation and a full calculation that takes account of stutter.

Allele-Specific Likelihood: Stutter-Free Version:

The stutter-free version of the likelihood calculation for allele k is applicable if the stutter rate is zero and is also used as a computational shortcut when the expected amount of "real" (non-stutter) detections is nonzero (due to k being in the genotype of at least one contributor) and the expected amount of stutter detections (calculated from the stutter rate and the number of molecules assigned to the "stutter neighbour", allele k+1) is below a threshold.

Ultimately, each of the molecules assigned to allele k is detected or not detected as a UMI via a process that is modeled as binomial, i.e. detection of individual molecules occurs independently. The binomial process with beta-distributed frequency parameter and allele-specific number of potentially detectable molecules implies a beta-binomial distribution for the observed UMI count at every allele. The allele-specific likelihood is therefore calculated using the formula for the beta-binomial distribution.

We calculate probabilities only for observed alleles; penalties that should arise from unobserved alleles having nonzero probability of being observed are ignored.

Handling Stutter and Other Drop-In:

The second likelihood calculation is used in the minority of cases where stutter is determined to be relevant (see above). At an allele k with UMI count of M, some implementations consider all values m from 0 to M as possible values for the number of UMIs originating from the allele in question, with the remaining (M-m) UMIs originating from allele k+1. The likelihood for one of these cases is the product of the likelihood for the true counts and the likelihood for the stutter counts (under a binomial model with N equal to the number of original UMIs at allele k+1 and binomial frequency equal to the stutter rate). The overall likelihood is a (linear-domain) sum over all of these cases.

In practice, some implementations do not need to calculate all of the terms in the above sum. This is because the stutter rate is small, so that the distribution of the number of stutter observations reaches zero quickly (a large number of stutter observations is essentially impossible, and corresponding terms in the sum will be effectively zero). some implementations keep track of the cumulative distribution of the number of stutter observations and terminate the sum when the remaining probability weight falls below a threshold.

General drop-in is handled by adding a fixed number of molecules to the number of UMIs assigned to allele k+1 when determining the number of molecules from which stutter can potentially originate. The number is set to expected_dropin/stutter_prob, so that the expected number of drop-in UMIs is equal to expected_dropin.

Handling Drop-Out:

We distinguish two types of drop-out:

Natural drop-out: this is when the binomial process results in a count of zero for an allele that is present in the genotype of a contributor. Rather than explicitly representing every potential allele (impossible absent an exhaustive list of potential alleles, or would also be expensive) some implementations use a special "dummy" out-of-sample allele. This allele may be present in any genotype configuration, has a UMI count of zero, and is treated like an ordinary allele. Natural drop-out is likely for alleles of low-frequency contributors but highly unlikely for alleles of high-frequency contributors.

In order to assign a sensible prior probability for the out-of-sample allele some implementations make a guess for the total number of potential alleles, and set a uniform prior over these potential alleles. The out-of-sample prior is therefore proportional to the number of unobserved alleles. Currently the guess for the number of potential alleles is obtained by interpolating all integers between the shortest and longest observed integer-valued alleles, adding any observed non-integer-valued alleles, and returning the max of the resulting value and 5.

Mechanistic drop-out: some implementations incorporate a special mechanism into the model whereby an allele may be "invisible" to the sequencer (e.g. due to mutations in the primer region), in which case some implementations observe no UMIs for it regardless of its total molecule count (i.e. mechanistic drop-out is as likely for high-frequency contributors as for low-frequency contributors). The set of all invisible alleles is represented by a second dummy allele.

Since this allele is impossible to observe its likelihood is 1 regardless of the data; its only direct contribution to the joint probability is via its prior (which must therefore be set low). For computational convenience some implementations use a hardcoded parameter dropout_prob as the prior probability of the invisible allele, scaling the priors of visible alleles to sum to 1-dropout_prob. This allows calculation of the genotype prior probabilities (see below) during preprocessing, with the drop-out probability acting as an extra population allele frequency value.

For single-source samples, the inferred posterior probabilities of homozygous alleles depends strongly on the value of dropout_prob, because it determines the probability of the main alternative hypothesis (heterozygote with 1 allele invisible) that the model has to consider. Some implementation calibrated dropout_prob to 1e-4, based on an intuition that the resulting posterior probability for single-source homozygote alleles (around 0.999) is reasonable.

This allele may be present in any genotype configuration. It is given special treatment when calculating the prior of a configuration, and ignored during likelihood calculation.

During aggressive pruning of genotype configurations (see above; based on read counts), occurrences of this allele are penalized using an ad hoc conversion from their likelihood penalty (which depends on dropout_prob) to a "count" value meant to be comparable with the mismatch counts estimated for regular alleles. The conversion is based on the normal approximation to the binomial, by calculating how far from the peak you have to be to suffer a likelihood penalty of −log(dropout_prob). The conversion is 1.2876*sqrt(max(read_numbers)/avg_det_prob), where the constant is sqrt(−2p(1−p)ln(D)) where p is avg_det_prob=0.1 and D is dropout-prob=1e-4. Note the dependence on coverage; some implementations are using the coverage of the most abundant allele.

The list of genotype configurations that is generated during preprocessing includes genotypes in which one or more allele is the drop-out allele. The observed count for the drop-out allele is always 0 and its likelihood is always 1. Despite having a high likelihood the model does not frequently use the drop-out mechanism to explain the data, because the low drop-out probability induces a low prior.

Prior and Posterior Calculation:

The prior probability of the genotype of an individual contributor is calculated from the population allele frequencies under the Hardy-Weinberg model: $P(G)=p^2$ for a homozygous genotype with allele frequency p and $P(G)=2pq$ for a heterozygous genotype with allele frequencies p and q. The prior probability of a multi-contributor genotype configuration is the product of the per-contributor priors. This is calculated during preprocessing at the time that the genotype configurations are constructed and reused in every marginal likelihood calculation. To account for drop-out some implementations add a dummy drop-out allele with a fixed prior probability to be set based on experimental measurement; population allele frequencies are discounted accordingly.

The posterior probability of a genotype configuration is the prior multiplied by the likelihood, normalized by the sum over genotype space (computed explicitly because some implementations calculate the terms for every genotype configuration anyway). The posterior probability that a specific contributor (e.g. the major contributor) has a specific genotype is obtained by summing over genotype configurations containing that genotype.

For sample inclusion queries practitioners are interested in the posterior probability that the specified multiple-locus genotype appears in any contributor, provided that it is the same contributor at all loci. This is obtained by summing, over all contributors i, the probability that contributor i has the specified genotype at all loci (i.e. the order in which the loops are nested matters).

Samples used herein contain nucleic acids that are "cell-free" (e.g., cfDNA) or cell-bound (e.g., cellular DNA). Cell-free nucleic acids, including cell-free DNA, can be obtained by various methods known in the art from biological samples including but not limited to plasma, serum, and urine (see, e.g., Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]). To separate cell-free DNA from cells in a sample, various methods including, but not limited to fractionation, centrifugation (e.g., density gradient centrifugation), DNA-specific precipitation, or high-throughput cell sorting and/or other separation methods can be used. Commercially available kits for manual and automated separation of cfDNA are available (Roche Diagnostics, Indianapolis, IN, Qiagen, Valencia, CA, Macherey-Nagel, Duren, DE). Biological samples comprising cfDNA have been used in assays to determine the presence or absence of chromosomal abnormalities, e.g., trisomy 21, by sequencing assays that can detect chromosomal aneuploidies and/or various polymorphisms.

Samples

Samples used herein contain nucleic acids that are "cell-free" (e.g., cfDNA) or cell-bound (e.g., cellular DNA). Cell-free nucleic acids, including cell-free DNA, can be obtained by various methods known in the art from biological samples including but not limited to plasma, serum, and urine (see, e.g., Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]). To separate cell-free DNA from cells in a sample, various methods including, but not limited to fractionation, centrifugation (e.g., density gradient centrifugation), DNA-specific precipitation, or high-throughput cell sorting and/or other separation methods can be used. Commercially available kits for manual and automated separation of cfDNA are available (Roche Diagnostics, Indianapolis, IN, Qiagen, Valencia, CA, Macherey-Nagel, Duren, DE). Biological samples comprising cfDNA have been used in assays to determine the presence or absence of chromosomal abnormalities, e.g., trisomy 21, by sequencing assays that can detect chromosomal aneuploidies and/or various polymorphisms.

In various embodiments the DNA present in the sample can be enriched specifically or non-specifically prior to use (e.g., prior to preparing a sequencing library). Non-specific enrichment of sample DNA refers to the whole genome amplification of the genomic DNA fragments of the sample that can be used to increase the level of the sample DNA prior to preparing a DNA sequencing library. Non-specific enrichment can be the selective enrichment of one of the two genomes present in a sample that comprises more than one genome. For example, non-specific enrichment can be selective of the cancer genome in a plasma sample, which can be obtained by known methods to increase the relative proportion of cancer to normal DNA in a sample. Alternatively, non-specific enrichment can be the non-selective amplification of both genomes present in the sample. For example, non-specific amplification can be of cancer and normal DNA in a sample comprising a mixture of DNA from the cancer and normal genomes. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample comprising the mixture of cfDNA from different genomes is un-enriched for cfDNA of the genomes present in the mixture. In other embodiments, the sample comprising the mixture of cfDNA from different genomes is non-specifically enriched for any one of the genomes present in the sample.

The sample comprising the nucleic acid(s) to which the methods described herein are applied typically comprises a biological sample ("test sample"), e.g., as described above.

Accordingly, in certain embodiments the sample comprises or consists of a purified or isolated polynucleotide, or it can comprise samples such as a tissue sample, a biological fluid sample, a cell sample, and the like. Suitable biological fluid samples include, but are not limited to blood, plasma, serum, sweat, tears, sputum, urine, sputum, ear flow, lymph, saliva, cerebrospinal fluid, ravages, bone marrow suspension, vaginal flow, trans-cervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures, e.g., blood, plasma, serum, sweat, tears, sputum, urine, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples, e.g., a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments, samples can be obtained from sources, including, but not limited to, samples from different individuals, samples from different developmental stages of the same or different individuals, samples from different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent (e.g., HIV), and the like.

In one illustrative, but non-limiting embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples.

In another illustrative, but non-limiting embodiment, the maternal sample is a mixture of two or more biological samples, e.g., the biological sample can comprise two or more of a biological fluid sample, a tissue sample, and a cell culture sample. In some embodiments, the sample is a sample that is easily obtainable by non-invasive procedures, e.g., blood, plasma, serum, sweat, tears, sputum, urine, milk, sputum, ear flow, saliva and feces. In some embodiments, the biological sample is a peripheral blood sample, and/or the plasma and serum fractions thereof. In other embodiments, the biological sample is a swab or smear, a biopsy specimen, or a sample of a cell culture. As disclosed above, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acid(s) from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation.

Sequencing Library Preparation

In one embodiment, the methods described herein can utilize next generation sequencing technologies (NGS), that allow multiple samples to be sequenced individually as genomic molecules (i.e., singleplex sequencing) or as pooled samples comprising indexed genomic molecules (e.g., multiplex sequencing) on a single sequencing run. These methods can generate up to several hundred million reads of DNA sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

In various embodiments the use of such sequencing technologies does not involve the preparation of sequencing libraries.

However, in certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as non-coding regulatory sequences such as promoter and enhancer sequences. In certain embodiments, the primary polynucleotide molecules comprise human genomic DNA molecules, e.g., cfDNA molecules present in peripheral blood of a pregnant subject.

Preparation of sequencing libraries for some NGS sequencing platforms is facilitated by the use of polynucleotides comprising a specific range of fragment sizes. Preparation of such libraries typically involves the fragmentation of large polynucleotides (e.g. cellular genomic DNA) to obtain polynucleotides in the desired size range.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, J Biol. Chem 265:17323-17333 [1990]; Richards and Boyer, J Mol Biol 11:327-240 [1965]) which may need to be repaired as they may lack the requisite 5'-phosphate for the subsequent enzymatic reactions, e.g., ligation of sequencing adaptors, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols, e.g., protocols for sequencing using, for example, the Illumina platform as described elsewhere herein, instruct users to end-repair sample DNA, to purify the end-repaired products prior to dA-tailing, and to purify the dA-tailing products prior to the adaptor-ligating steps of the library preparation.

Various embodiments of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are examples of methods for preparation of a sequencing library, which can be found in patent application Ser. No. 13/555,037 filed on Jul. 20, 2012, which is incorporated by reference by its entirety.

Sequencing Methods

In some implementations, the prepared samples (e.g., Sequencing Libraries) are sequenced as part of the procedure for deconvolving mixtures of nucleic acid. Any of a number of sequencing technologies can be utilized.

Some sequencing technologies are available commercially, such as the sequencing-by-hybridization platform from Affymetrix Inc. (Sunnyvale, CA) and the sequencing-by-synthesis platforms from 454 Life Sciences (Bradford, CT), Illumina/Solexa (Hayward, CA) and Helicos Biosciences (Cambridge, MA), and the sequencing-by-ligation platform from Applied Biosystems (Foster City, CA), as described below. In addition to the single molecule sequencing performed using sequencing-by-synthesis of Helicos Biosciences, other single molecule sequencing technologies include, but are not limited to, the SMRT™ technology of Pacific Biosciences, the ION TORRENT™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM). Illustrative sequencing technologies are described in greater detail below.

In one illustrative, but non-limiting, embodiment, the methods described herein comprise obtaining sequence information for the nucleic acids in a test sample, e.g., cfDNA in a maternal sample, cfDNA or cellular DNA in a subject being screened for a cancer, and the like, using Illumina's sequencing-by-synthesis and reversible terminator-based sequencing chemistry (e.g. as described in Bentley et al., Nature 6:53-59 [2009]). Template DNA can be genomic DNA, e.g., cellular DNA or cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments approximately 170 base pairs (bp) in length (Fan et al., Clin Chem 56:1279-1286 [2010]), and no fragmentation of the DNA is required prior to sequencing. Circulating tumor DNA also exist in short fragments, with a size distribution peaking at about 150-170 bp. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchor oligos (not to be confused with the anchor/anchored reads in the analysis of repeat expansion). Under limiting-dilution conditions, adapter-modified, single-stranded template DNA is added to the flow cell and immobilized by hybridization to the anchor oligos. Attached DNA fragments are extended and bridge amplified to create an ultra-high density sequencing flow cell with hundreds of millions of clusters, each containing about 1,000 copies of the same template. In one embodiment, the randomly fragmented genomic DNA is amplified using PCR before it is subjected to cluster amplification. Alternatively, an amplification-free (e.g., PCR free) genomic library preparation is used, and the randomly fragmented genomic DNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about tens to a few hundred base pairs are aligned against a reference genome and unique mapping of the short sequence reads to the reference genome are identified using specially developed data analysis pipeline software. After completion of the first read, the templates can be regenerated in situ to enable a second read from the opposite end of the fragments. Thus, either single-end or paired end sequencing of the DNA fragments can be used.

Various embodiments of the disclosure may use sequencing by synthesis that allows paired end sequencing. In some embodiments, the sequencing by synthesis platform by Illumina involves clustering fragments. Clustering is a process in which each fragment molecule is isothermally amplified. In some embodiments, as the example described here, the fragment has two different adaptors attached to the two ends of the fragment, the adaptors allowing the fragment to hybridize with the two different oligos on the surface of a flow cell lane. The fragment further includes or is connected to two index sequences at two ends of the fragment, which index sequences provide labels to identify different samples in multiplex sequencing. In some sequencing platforms, a fragment to be sequenced is also referred to as an insert.

In some implementation, a flow cell for clustering in the Illumina platform is a glass slide with lanes. Each lane is a glass channel coated with a lawn of two types of oligos. Hybridization is enabled by the first of the two types of oligos on the surface. This oligo is complementary to a first adapter on one end of the fragment. A polymerase creates a compliment strand of the hybridized fragment. The double-stranded molecule is denatured, and the original template strand is washed away. The remaining strand, in parallel with many other remaining strands, is clonally amplified through bridge application.

In bridge amplification, a strand folds over, and a second adapter region on a second end of the strand hybridizes with the second type of oligos on the flow cell surface. A polymerase generates a complimentary strand, forming a double-stranded bridge molecule. This double-stranded molecule is denatured resulting in two single-stranded molecules tethered to the flow cell through two different oligos. The process is then repeated over and over, and occurs simultaneously for millions of clusters resulting in clonal amplification of all the fragments. After bridge amplification, the reverse strands are cleaved and washed off, leaving only the forward strands. The 3' ends are blocked to prevent unwanted priming.

After clustering, sequencing starts with extending a first sequencing primer to generate the first read. With each cycle, fluorescently tagged nucleotides compete for addition to the growing chain. Only one is incorporated based on the sequence of the template. After the addition of each nucleotide, the cluster is excited by a light source, and a characteristic fluorescent signal is emitted. The number of cycles determines the length of the read. The emission wavelength and the signal intensity determine the base call. For a given cluster all identical strands are read simultaneously. Hundreds of millions of clusters are sequenced in a massively parallel manner. At the completion of the first read, the read product is washed away.

In the next step of protocols involving two index primers, an index 1 primer is introduced and hybridized to an index 1 region on the template. Index regions provide identification of fragments, which is useful for de-multiplexing samples in a multiplex sequencing process. The index 1 read is generated similar to the first read. After completion of the index 1 read, the read product is washed away and the 3' end of the strand is de-protected. The template strand then folds over and binds to a second oligo on the flow cell. An index 2 sequence is read in the same manner as index 1. Then an index 2 read product is washed off at the completion of the step.

After reading two indices, read 2 initiates by using polymerases to extend the second flow cell oligos, forming a double-stranded bridge. This double-stranded DNA is denatured, and the 3' end is blocked. The original forward strand is cleaved off and washed away, leaving the reverse strand. Read 2 begins with the introduction of a read 2 sequencing primer. As with read 1, the sequencing steps are repeated until the desired length is achieved. The read 2 product is washed away. This entire process generates millions of reads, representing all the fragments. Sequences from pooled sample libraries are separated based on the unique indices introduced during sample preparation. For each sample, reads of similar stretches of base calls are locally clustered. Forward and reversed reads are paired creating contiguous sequences. These contiguous sequences are aligned to the reference genome for variant identification.

The sequencing by synthesis example described above involves paired end reads, which is used in many of the embodiments of the disclosed methods. Paired end sequencing involves two reads from the two ends of a fragment. When a pair of reads are mapped to a reference sequence, the base-pair distance between the two reads can be determined, which distance can then be used to determine the length of the fragments from which the reads were obtained. In some instances, a fragment straddling two bins would have one of its pair-end read aligned to one bin, and another to an adjacent bin. This gets rarer as the bins get longer or the reads get shorter. Various methods may be used to account for the bin-membership of these fragments. For instance, they can be omitted in determining fragment size frequency of a bin; they can be counted for both of the adjacent bins; they can be assigned to the bin that encompasses the larger number of base pairs of the two bins; or they can be assigned to both bins with a weight related to portion of base pairs in each bin.

Paired end reads may use insert of different length (i.e., different fragment size to be sequenced). As the default meaning in this disclosure, paired end reads are used to refer to reads obtained from various insert lengths. In some instances, to distinguish short-insert paired end reads from long-inserts paired end reads, the latter is also referred to as mate pair reads. In some embodiments involving mate pair reads, two biotin junction adaptors first are attached to two ends of a relatively long insert (e.g., several kb). The biotin junction adaptors then link the two ends of the insert to form a circularized molecule. A sub-fragment encompassing the biotin junction adaptors can then be obtained by further fragmenting the circularized molecule. The sub-fragment including the two ends of the original fragment in opposite sequence order can then be sequenced by the same procedure as for short-insert paired end sequencing described above. Further details of mate pair sequencing using an Illumina platform is shown in an online publication at the following URL, which is incorporated by reference by its entirety: res|.|illumina|.|com/documents/products/technotes/technote_nextera_matepair_data_processing. Additional information about paired end sequencing can be found in U.S. Pat. No. 7,601,499 and US Patent Publication No.

2012/0,053,063, which are incorporated by reference with regard to materials on paired end sequencing methods and apparatuses.

After sequencing of DNA fragments, sequence reads of predetermined length, e.g., 100 bp, are mapped or aligned to a known reference genome. The mapped or aligned reads and their corresponding locations on the reference sequence are also referred to as tags. In one embodiment, the reference genome sequence is the NCBI36/hg18 sequence, which is available on the world wide web at genome1.lucsc1.ledu/cgi-bin/hgGateway?org=Human&db=hg18&hgsid=166260105). Alternatively, the reference genome sequence is the GRCh37/hg19, which is available on the world wide web at genome.ucsc.edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, CA, USA). In one embodiment, one end of the clonally expanded copies of the plasma cfDNA molecules is sequenced and processed by bioinformatics alignment analysis for the Illumina Genome Analyzer, which uses the Efficient Large-Scale Alignment of Nucleotide Databases (ELAND) software.

In one illustrative, but non-limiting, embodiment, the methods described herein comprise obtaining sequence information for the nucleic acids in a test sample, e.g., cfDNA in a maternal sample, cfDNA or cellular DNA in a subject being screened for a cancer, and the like, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm2. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

In another illustrative, but non-limiting embodiment, the methods described herein comprise obtaining sequence information for the nucleic acids in the test sample, e.g., cfDNA in a maternal test sample, cfDNA or cellular DNA in a subject being screened for a cancer, and the like, using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting, embodiment, the methods described herein comprises obtaining sequence information for the nucleic acids in the test sample, e.g., cfDNA in a maternal test sample, cfDNA or cellular DNA in a subject being screened for a cancer, and the like, using the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting embodiment, the methods described herein comprise obtaining sequence information for the nucleic acids in the test sample, e.g., cfDNA in a maternal test sample, cfDNA or cellular DNA in a subject being screened for a cancer, and the like, using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW detector comprises a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting embodiment, the methods described herein comprise obtaining sequence information for the nucleic acids in the test sample, e.g., cfDNA in a maternal test sample, cfDNA or cellular DNA in a subject being screened for a cancer, and the like, using nanopore sequencing (e.g. as described in Soni G V and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting, embodiment, the methods described herein comprises obtaining sequence information for the nucleic acids in the test sample, e.g., cfDNA in a maternal test sample, cfDNA or cellular DNA in a subject being screened for a cancer, and the like, using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the present method comprises obtaining sequence information for the nucleic acids in the test sample, e.g., cfDNA in a maternal test sample, using transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

In another embodiment, the present method comprises obtaining sequence information for the nucleic acids in the test sample, e.g., cfDNA in a maternal test sample, using sequencing by hybridization. Sequencing-by-hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In some embodiments of the methods described herein, the mapped sequence tags comprise sequence reads of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence tags comprise sequence reads that are 36 bp. Mapping of the sequence tags is achieved by comparing the sequence of the tag with the sequence of the reference to determine the chromosomal origin of the sequenced nucleic acid (e.g. cfDNA) molecule, and specific genetic sequence information is not needed. A small degree of mismatch (0-2 mismatches per sequence tag) may be allowed to account for minor polymorphisms that may exist between the reference genome and the genomes in the mixed sample.

A plurality of sequence tags are typically obtained per sample. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between 20 and 40 bp reads, e.g., 36 bp, are obtained from mapping the reads to the reference genome per sample. In one embodiment, all the sequence reads are mapped to all regions of the reference genome. In one embodiment, the tags that have been mapped to all regions, e.g., all chromosomes, of the reference genome are analyzed.

Apparatus and System for Deconvolving Mixtures of Nucleic Acid from Multiple Sources Analysis of the sequencing data and the diagnosis derived therefrom are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, counts or densities of such tags that align with particular regions of a reference sequence (e.g., that align to a chromosome or chromosome segment), reference sequences (including reference sequences providing solely or primarily polymorphisms), chromosome and segment doses, calls such as SNV or aneuploidy calls, normalized chromosome and segment values, pairs of chromosomes or segments and corresponding normalizing chromosomes or segments, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for generating an output indicating the presence or absence of an SNV or aneuploidy associated with a cancer, in a test sample. The computer product may contain instructions for performing any one or more of the above-described methods for determining a chromosomal anomaly. As explained, the computer product may include a non-transitory and/or tangible computer readable medium having a computer executable or compilable logic (e.g., instructions) recorded thereon for enabling a processor to deconvolve mixtures of nucleic acid. In one example, the computer product comprises a computer readable medium having a computer executable or compilable logic (e.g., instructions) recorded thereon for enabling a processor to deconvolve mixtures of nucleic acid.

The sequence information from the sample under consideration may be mapped to chromosome reference sequences to identify a number of sequence tags for each of any one or more chromosomes of interest and to identify a number of sequence tags for a normalizing segment sequence for each of said any one or more chromosomes of interest. In various embodiments, the reference sequences are stored in a database such as a relational or object database, for example.

It should be understood that it is not practical, or even possible in most cases, for an unaided human being to perform the computational operations of the methods disclosed herein. For example, mapping a single 30 bp read from a sample to any one of the human chromosomes might require years of effort without the assistance of a computational apparatus.

The methods disclosed herein can be performed using a system for quantifying a nucleic acid sample comprising nucleic acid of one or more contributors. The system comprising: (a) a sequencer for receiving nucleic acids from the test sample providing nucleic acid sequence information from the sample; (b) a processor; and (c) one or more computer-readable storage media having stored thereon instructions for execution on said processor to carry out a method for deconvolving mixtures of nucleic acid.

In some embodiments, the methods are instructed by a computer-readable medium having stored thereon computer-readable instructions for carrying out a method for deconvolve mixtures of nucleic acid. Thus one embodiment provides a computer program product comprising one or more computer-readable non-transitory storage media having stored thereon computer-executable instructions that, when executed by one or more processors of a computer system, cause the computer system to implement a method for quantifying a nucleic acid sample comprising nucleic acid of one or more contributors. The method includes: (a) receiving, by the computer system, nucleic acid sequence reads obtained from the nucleic acid sample and mapped to one or more alleles at one or more polymorphism loci; (b) determining, using the nucleic acid sequence reads and by the one or more processors, allele counts for each of the one or more alleles at the one or more polymorphism loci; and (c) quantifying, using a probabilistic mixture model and by the one or more processors, one or more fractions of nucleic acid of the one or more contributors in the nucleic acid sample, wherein using the probabilistic mixture model comprises applying a probabilistic mixture model to the allele counts, and the probabilistic mixture model uses probability distributions to model the allele counts at the one or more polymorphism loci, the probability distributions accounting for errors in the nucleic acid sequence reads.

In some embodiments, the instructions may further include automatically recording information pertinent to the method in a patient medical record for a human subject providing the maternal test sample. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the maternal test sample was taken. This may involve performing one or more additional tests or analyses on additional samples taken from the subject. In certain embodiments treating the subject comprises surgically removing the neoplastic (e.g., tumor) cells. In certain embodiments treating the subject comprises performing radiotherapy or causing radiotherapy to be performed on said subject to kill the neoplastic cells. In certain embodiments treating the subject comprises administering or causing to be administered to said subject an anti-cancer drug (e.g., matuzumab, erbitux, vectibix, nimotuzumab, panitumumab, fluorouracil, capecitabine, 5-trifluoromethyl-2'-deoxyuridine, methotrexate, raltitrexed, pemetrexed, cytosine arabinoside, 6-mercaptopurine, azathioprine, 6-thioguanine, pentostatin, fludarabine, cladribine, floxuridine, cyclophosphamide, neosar, ifosfamide, thiotepa, 1.3-bis(2-chloroethyl)-1-nitosourea, 1,-(2-chloroethyl)-3-cyclohexyl-1-nitrosourea, hexamethylmelamine, busulfan, procarbazine, dacarbazine, chlorambucil, melphalan, cisplatin, carboplatin, oxaliplatin, bendamustine, carmustine, chloromethine, dacarbazine, fotemustine, lomustine, mannosulfan, medaplatin, nimustine, prednimustine, ranimustine, satraplatin, semustine, Streptozocin, temozolomide, treosulfan, triaziquone, triethylene melamine, thiotepa, triplatin tetranitrate, trofosfamide, uramustine, doxorubicin, daunorubicin, mitoxantrone, etoposide, topotecan, teniposide, irinotecan, camptosar, camptothecin, belotecan, rubitecan, vincristine, vinblastine, vinorelbine, vindesine, paclitaxel, docetaxel, abraxane, ixabepilone, larotaxel, ortataxel, tesetaxel, vinflunine, imatinib mesylate, sunitinib malate, sorafenib tosylate, nilotinib hydrochloride monohydrate, tasigna, semaxanib, vandetanib, vatalanib, retinoic acid, a retinoic acid derivative, and the like).

Disclosed methods can also be performed using a computer processing system which is adapted or configured to perform a method for quantifying a nucleic acid sample comprising nucleic acid of one or more contributors. One embodiment provides a computer processing system which is adapted or configured to perform a method as described herein. In one embodiment, the apparatus comprises a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store tag counts for various chromosomes or genomes, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:

Reads obtained by sequencing nucleic acids in a test sample

Tags obtained by aligning reads to a reference genome or other reference sequence or sequences The reference genome or sequence Sequence tag density—Counts or numbers of tags for each of two or more regions (typically chromosomes or chromosome segments) of a reference genome or other reference sequences Identities of normalizing chromosomes or chromosome segments for particular chromosomes or chromosome segments of interest Doses for chromosomes or chromosome segments (or other regions) obtained from chromosomes or segments of interest and corresponding normalizing chromosomes or segments Thresholds for calling chromosome doses as either affected, non-affected, or no call The actual calls of chromosome doses Diagnoses (clinical condition associated with the calls)

Recommendations for further tests derived from the calls and/or diagnoses

Treatment and/or monitoring plans derived from the calls and/or diagnoses

These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a doctor's office or other clinical setting. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed to produce calls. At this remote location, as an example, the reads are aligned to a reference sequence to produce tags, which are counted and assigned to chromosomes or segments of interest. Also at the remote location, the counts are converted to doses using associated normalizing chromosomes or segments. Still further, at the remote location, the doses are used to generate calls.

Among the processing operations that may be employed at distinct locations are the following:

Sample collection

Sample processing preliminary to sequencing

Sequencing

Analyzing sequence data and quantifying a nucleic acid sample comprising nucleic acid of one or more contributors Diagnosis Reporting a diagnosis and/or a call to patient or health care provider Developing a plan for further treatment, testing, and/or monitoring Executing the plan Counseling Any one or more of these operations may be automated as described elsewhere herein. Typically, the sequencing and the analyzing of sequence data and deconvolving DNA mixture sample will be performed computationally. The other operations may be performed manually or automatically.

Examples of locations where sample collection may be performed include health practitioners' offices, clinics, patients' homes (where a sample collection tool or kit is provided), and mobile health care vehicles. Examples of locations where sample processing prior to sequencing may be performed include health practitioners' offices, clinics, patients' homes (where a sample processing apparatus or kit is provided), mobile health care vehicles, and facilities of DNA analysis providers. Examples of locations where sequencing may be performed include health practitioners' offices, clinics, health practitioners' offices, clinics, patients' homes (where a sample sequencing apparatus and/or kit is provided), mobile health care vehicles, and facilities of DNA analysis providers. The location where the sequencing takes place may be provided with a dedicated network connection for transmitting sequence data (typically reads) in an electronic format. Such connection may be wired or wireless and have and may be configured to send the data to a site where the data can be processed and/or aggregated prior to transmission to a processing site. Data aggregators can be maintained by health organizations such as Health Maintenance Organizations (HMOs).

The analyzing and/or deriving operations may be performed at any of the foregoing locations or alternatively at a further remote site dedicated to computation and/or the service of analyzing nucleic acid sequence data. Such locations include for example, clusters such as general purpose server farms, the facilities of a DNA analysis service business, and the like. In some embodiments, the computational apparatus employed to perform the analysis is leased or rented. The computational resources may be part of an internet accessible collection of processors such as processing resources colloquially known as the cloud. In some cases, the computations are performed by a parallel or massively parallel group of processors that are affiliated or unaffiliated with one another. The processing may be accomplished using distributed processing such as cluster computing, grid computing, and the like. In such embodiments, a cluster or grid of computational resources collective form a super virtual computer composed of multiple processors or computers acting together to perform the analysis and/or derivation described herein. These technologies as well as more conventional supercomputers may be employed to process sequence data as described herein. Each is a form of parallel computing that relies on processors or computers. In the case of grid computing these processors (often whole computers) are connected by a network (private, public, or the Internet) by a conventional network protocol such as Ethernet. By contrast, a supercomputer has many processors connected by a local high-speed computer bus.

In certain embodiments, the diagnosis is generated at the same location as the analyzing operation. In other embodiments, it is performed at a different location. In some examples, reporting the diagnosis is performed at the location where the sample was taken, although this need not be the case. Examples of locations where the diagnosis can be generated or reported and/or where developing a plan is performed include health practitioners' offices, clinics, internet sites accessible by computers, and handheld devices such as cell phones, tablets, smart phones, etc. having a wired or wireless connection to a network. Examples of locations where counseling is performed include health practitioners' offices, clinics, internet sites accessible by computers, handheld devices, etc.

In some embodiments, the sample collection, sample processing, and sequencing operations are performed at a first location and the analyzing and deriving operation is performed at a second location. However, in some cases, the sample collection is collected at one location (e.g., a health practitioner's office or clinic) and the sample processing and sequencing is performed at a different location that is optionally the same location where the analyzing and deriving take place.

In various embodiments, a sequence of the above-listed operations may be triggered by a user or entity initiating sample collection, sample processing and/or sequencing. After one or more these operations have begun execution the other operations may naturally follow. For example, the sequencing operation may cause reads to be automatically collected and sent to a processing apparatus which then conducts, often automatically and possibly without further user intervention, the sequence analysis. In some implementations, the result of this processing operation is then automatically delivered, possibly with reformatting as a diagnosis, to a system component or entity that processes reports the information to a health professional and/or patient. As explained such information can also be automatically processed to produce a treatment, testing, and/or monitoring plan, possibly along with counseling information. Thus, initiating an early stage operation can trigger an end to end sequence in which the health professional, patient or other concerned party is provided with a diagnosis, a plan, counseling and/or other information useful for acting on a physical condition. This is accomplished even though parts of the overall system are physically separated and possibly remote from the location of, e.g., the sample and sequence apparatus.

Figure 4:
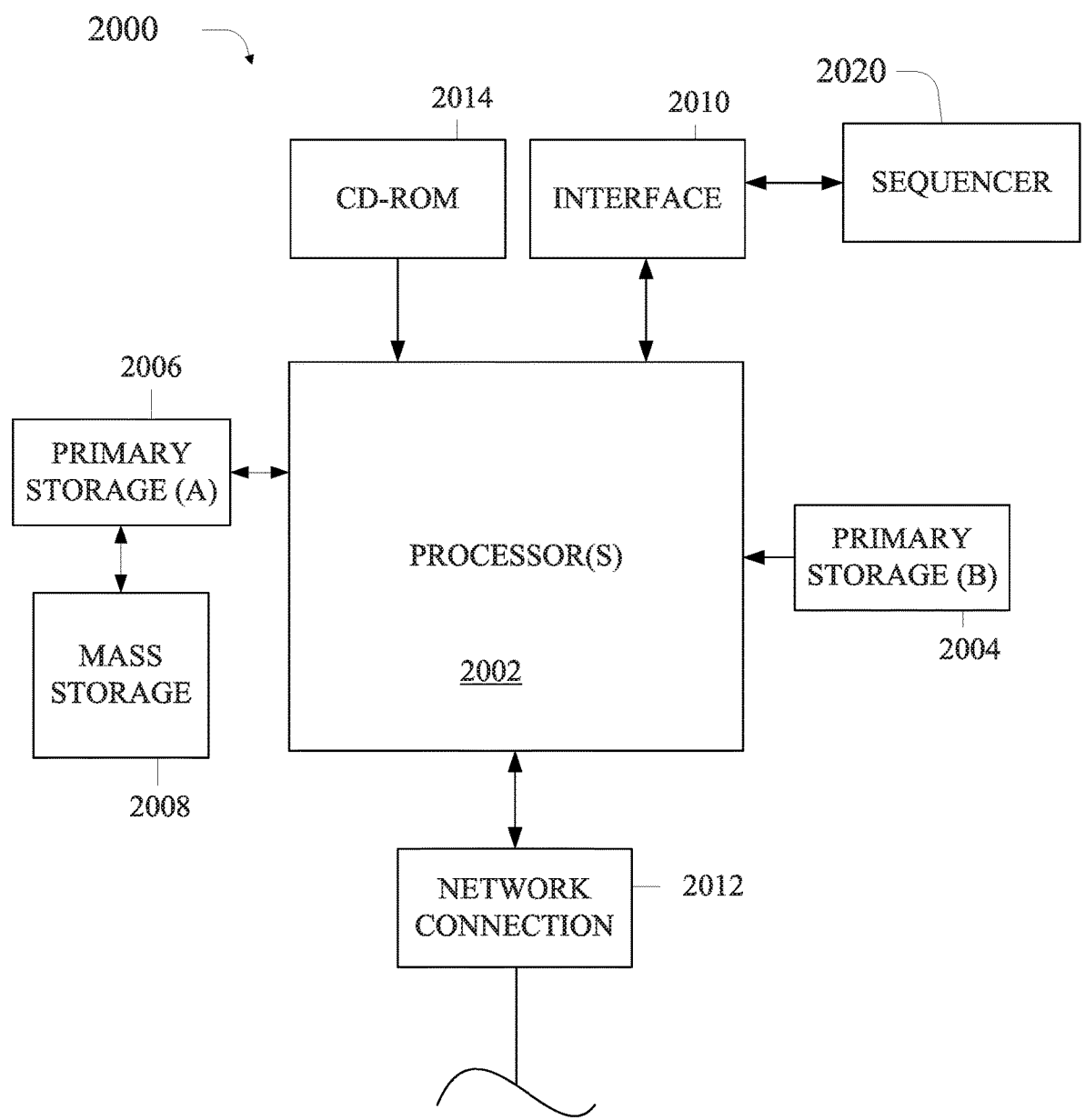
FIG. 4 shows block diagram of a typical computer system that can serve as a computational apparatus according to certain embodiments.

FIG. 4 illustrates, in simple block format, a typical computer system that, when appropriately configured or designed, can serve as a computational apparatus according to certain embodiments. The computer system 2000 includes any number of processors 2002 (also referred to as central processing units, or CPUs) that are coupled to storage devices including primary storage 2006 (typically a random access memory, or RAM), primary storage 2004 (typically a read only memory, or ROM). CPU 2002 may be of various types including microcontrollers and microprocessors such as programmable devices (e.g., CPLDs and FPGAs) and non-programmable devices such as gate array ASICs or general-purpose microprocessors. In the depicted embodiment, primary storage 2004 acts to transfer data and instructions uni-directionally to the CPU and primary storage 2006 is used typically to transfer data and instructions in a bi-directional manner. Both of these primary storage devices may include any suitable computer-readable media such as those described above. A mass storage device 2008 is also coupled bi-directionally to primary storage 2006 and provides additional data storage capacity and may include any of the computer-readable media described above. Mass storage device 2008 may be used to store programs, data and the like and is typically a secondary storage medium such as a hard disk. Frequently, such programs, data and the like are temporarily copied to primary memory 2006 for execution on CPU 2002. It will be appreciated that the information retained within the mass storage device 2008, may, in appropriate cases, be incorporated in standard fashion as part of primary storage 2004. A specific mass storage device such as a CD-ROM 2014 may also pass data uni-directionally to the CPU or primary storage.

CPU 2002 is also coupled to an interface 2010 that connects to one or more input/output devices such as such as a nucleic acid sequencer (2020), video monitors, track balls, mice, keyboards, microphones, touch-sensitive displays, transducer card readers, magnetic or paper tape readers, tablets, styluses, voice or handwriting recognition peripherals, USB ports, or other well-known input devices such as, of course, other computers. Finally, CPU 2002 optionally may be coupled to an external device such as a database or a computer or telecommunications network using an external connection as shown generally at 2012. With such a connection, it is contemplated that the CPU might receive information from the network, or might output information to the network in the course of performing the method steps described herein. In some implementations, a nucleic acid sequencer (2020) may be communicatively linked to the CPU 2002 via the network connection 2012 instead of or in addition to via the interface 2010.

In one embodiment, a system such as computer system 2000 is used as a data import, data correlation, and querying system capable of performing some or all of the tasks described herein. Information and programs, including data files can be provided via a network connection 2012 for access or downloading by a researcher. Alternatively, such information, programs and files can be provided to the researcher on a storage device.

In a specific embodiment, the computer system 2000 is directly coupled to a data acquisition system such as a microarray, high-throughput screening system, or a nucleic acid sequencer (2020) that captures data from samples. Data from such systems are provided via interface 2010 for analysis by system 2000. Alternatively, the data processed by system 2000 are provided from a data storage source such as a database or other repository of relevant data. Once in apparatus 2000, a memory device such as primary storage 2006 or mass storage 2008 buffers or stores, at least temporarily, relevant data. The memory may also store various routines and/or programs for importing, analyzing and presenting the data, including sequence reads, UMIs, codes for determining sequence reads, collapsing sequence reads and correcting errors in reads, etc.

In certain embodiments, the computers used herein may include a user terminal, which may be any type of computer (e.g., desktop, laptop, tablet, etc.), media computing platforms (e.g., cable, satellite set top boxes, digital video recorders, etc.), handheld computing devices (e.g., PDAs, e-mail clients, etc.), cell phones or any other type of computing or communication platforms.

In certain embodiments, the computers used herein may also include a server system in communication with a user terminal, which server system may include a server device or decentralized server devices, and may include mainframe computers, mini computers, super computers, personal computers, or combinations thereof. A plurality of server systems may also be used without departing from the scope of the present invention. User terminals and a server system may communicate with each other through a network. The network may comprise, e.g., wired networks such as LANs (local area networks), WANs (wide area networks), MANs (metropolitan area networks), ISDNs (Intergrated Service Digital Networks), etc. as well as wireless networks such as wireless LANs, CDMA, Bluetooth, and satellite communication networks, etc. without limiting the scope of the present invention.

Figure 5:
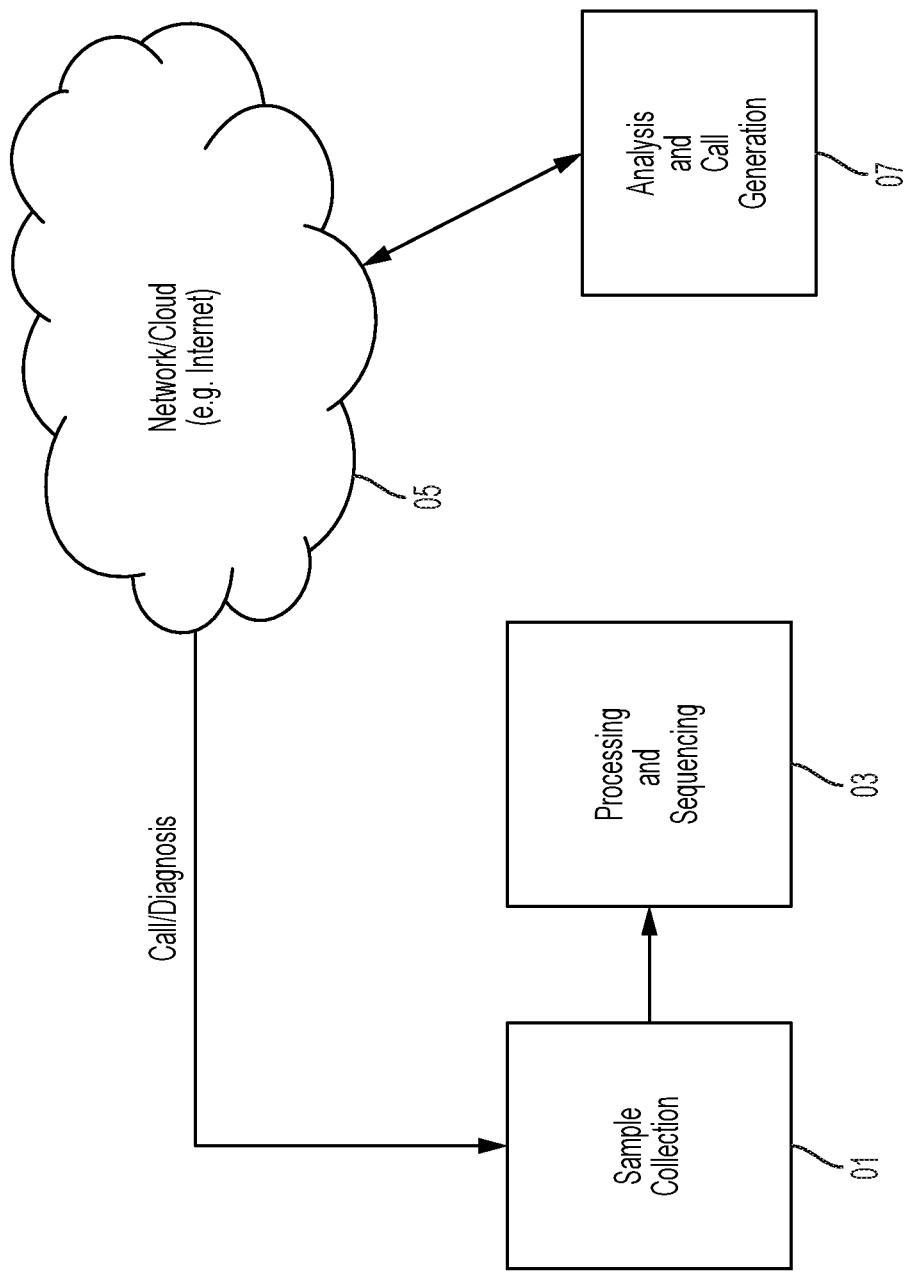
FIG. 5 shows one implementation of a dispersed system for producing a call or diagnosis from a test sample.

FIG. 5 shows one implementation of a dispersed system for producing a call or diagnosis from a test sample. A sample collection location 01 is used for obtaining a test sample. The samples then is provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 5.

The sequence data is provided to a remote location 07 where analysis and call generation are performed. This location may include one or more powerful computational devices such as computers or processors. After the computational resources at location 07 have completed their analysis and generated a call from the sequence information received, the call is relayed back to the network 05. In some implementations, not only is a call generated at location 07 but an associated diagnosis is also generated. The call and or diagnosis are then transmitted across the network and back to the sample collection location 01 as illustrated in FIG. 5. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

Figure 6:
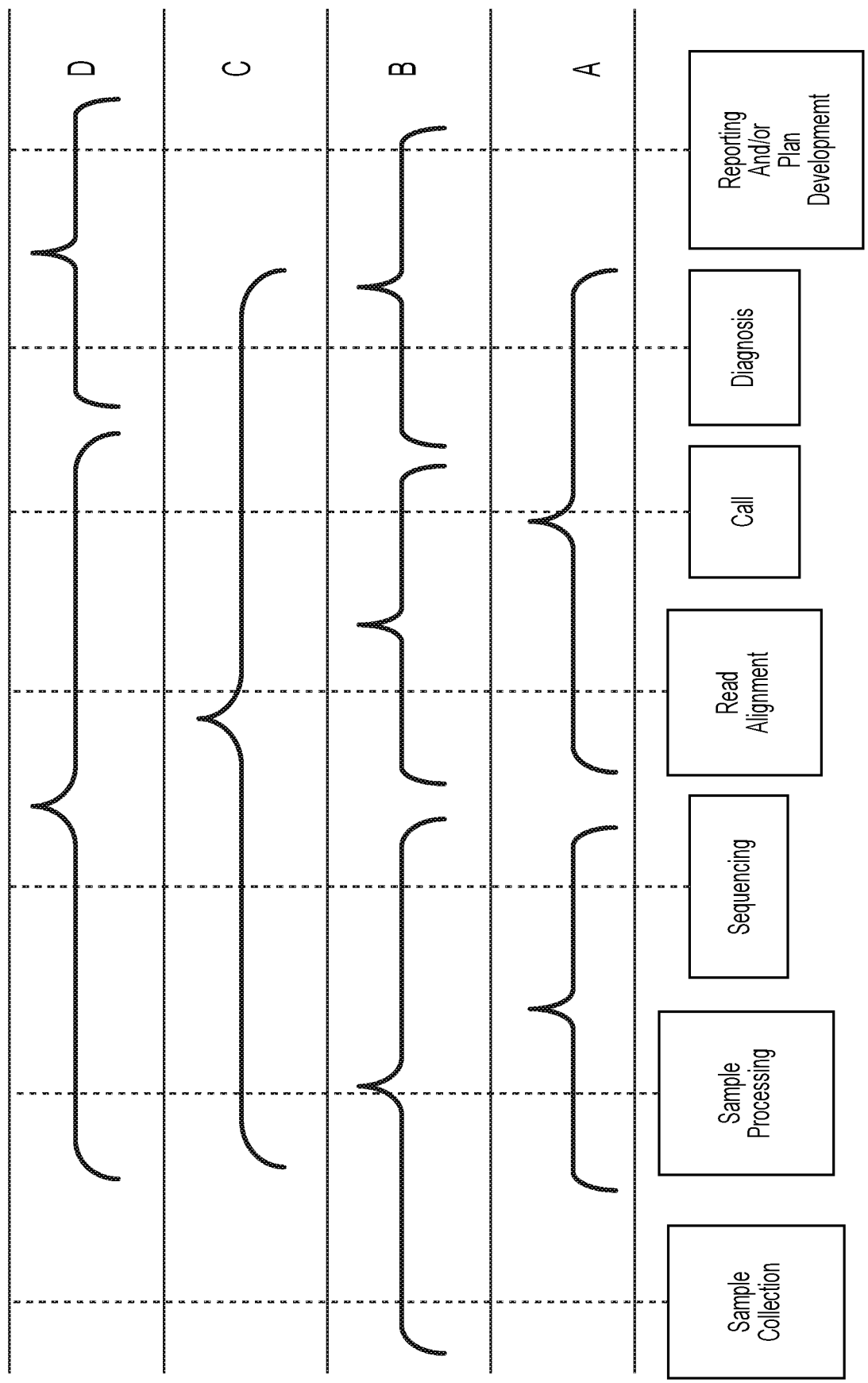
FIG. 6 shows options for performing various operations of some implementations at distinct locations.

FIG. 6 elaborates on the options for performing various operations at distinct locations. In the most granular sense depicted in FIG. 6, each of the following operations is performed at a separate location: sample collection, sample processing, sequencing, read alignment, calling, diagnosis, and reporting and/or plan development.

In one embodiment that aggregates some of these operations, sample processing and sequencing are performed in one location and read alignment, calling, and diagnosis are performed at a separate location. See the portion of FIG. 6 identified by reference character A. In another implementation, which is identified by character B in FIG. 6, sample collection, sample processing, and sequencing are all performed at the same location. In this implementation, read alignment and calling are performed in a second location. Finally, diagnosis and reporting and/or plan development are performed in a third location. In the implementation depicted by character C in FIG. 6, sample collection is performed at a first location, sample processing, sequencing, read alignment, calling, and diagnosis are all performed together at a second location, and reporting and/or plan development are performed at a third location. Finally, in the implementation labeled D in FIG. 6, sample collection is performed at a first location, sample processing, sequencing, read alignment, and calling are all performed at a second location, and diagnosis and reporting and/or plan management are performed at a third location.

One embodiment provides a system for analyzing cell-free DNA (cfDNA) for simple nucleotide variants associated with tumors, the system including a sequencer for receiving a nucleic acid sample and providing nucleic acid sequence information from the nucleic acid sample; a processor; and a machine readable storage medium comprising instructions for execution on said processor, the instructions comprising: (a) code for receiving nucleic acid sequence reads obtained from the nucleic acid sample and mapped to one or more alleles at one or more polymorphism loci; (b) code for determining, using the nucleic acid sequence reads, allele counts for each of the one or more alleles at the one or more polymorphism loci; and (c) code for quantifying, using a probabilistic mixture model, one or more fractions of nucleic acid of the one or more contributors in the nucleic acid sample. In some implementations, using the probabilistic mixture model comprises applying a probabilistic mixture model to the allele counts. The probabilistic mixture model uses probability distributions to model the allele counts at the one or more polymorphism loci, the probability distributions accounting for errors in the nucleic acid sequence reads.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

EXPERIMENTAL

Example 1

This example uses data obtained from actual DNA mixture samples to illustrate that some implementations can provide higher accuracy and reliability, as well as lower empirical bias, in quantifying DNA mixture samples, than conventional technologies that do not use the probabilistic approaches disclosed herein.

The DNA mixture samples included two DNA from genomes (contributors), and the minor fractions are 0.1%, 0.2%, 0.4%, and 2% in different samples. Some samples included 3 ng of input DNA, and others included 10 ng. The samples were processed in two experimental procedures labeled as Nack or Nack2 to indicate two primer designs, where the numbers of target loci are different for the two designs. Some samples were processed using the MiSeq sequencing platform and some using the MiniSeq platform.

The sample data were analyzed using three different methods. Table 2 shows the average of coefficient of variance (CV, defined as standard_deviation_of_predictions/true_fraction) values over multiple mixture fractions and the average of coefficient of variation+bias (CVB, commonly denoted as CV(RMSD) and defined as RMSD/true_fraction) values over multiple mixture fractions for the three different methods using various samples and experimental procedures. The first method applies a probabilistic model including a binomial distribution for modeling sequencing errors. The first method corresponds to some implementations descried as the Seq Model above. The data for the first method (Seq) are shown in the third row of Table 8. The second method applies a probabilistic mixture model including probability distributions accounting for DNA extraction errors, PCR amplification errors, and sequencing errors. The second method corresponds to some implementations descried as the Extraction-PCR-Seq Model above. The data for the second method (EPS) are shown in the fourth row of Table 8.

The third method applies a deterministic linear regression model to describe the allele account data. It estimates the summed squared error of the data as follows.

$$E = [r_i - p_i(\beta)]T \cdot [r_i - p_i(\beta)]$$

where r is the observed allele fraction, $p_i = G \cdot \beta$ is the expected allele fraction for locus i, which is a linear function of $\beta$, where G is a matrix of genotypes for n loci and d donors, and $\beta$ is a length d vector of unknown contributor fraction. The data for the third method (NaiveLM) are shown in the fifth row of Table 8.

It is worth noting that the genotype information of the contributors was not used to quantify the contributor fractions in the Seq or EPS method, but it was used in the NaiveLM method. Despite the fact that the Seq method and the EPS method did not need to use the genotype information of the contributors, they produced more reliable results as indicated by the smaller coefficient of variation values than the NaiveLM method. Moreover, the Seq method and the EPS method had lower bias as indicated by the smaller CVB values than the NaiveLM method. The best results among the three methods are bolded in Table 8. In short, the two methods using probabilistic mixture models produced more reliable, accurate, and less biased results than the linear regression method. Table 8.

| Algorithm | Genotype | Nack (3 ng, 10 ng) | | Nack2 (3 ng, 10 ng) | | Nack2 MiniSeq (3 ng, 10 ng) | | Nack2 Validation (3 ng, 10 ng) | |
|---|---|---|---|---|---|---|---|---|---|
| | | CV | CVB | CV | CVB | CV | CVB | CV | CVB |
| Seq | Not used | 0.151 | 0.796 | 0.214 | 0.688 | 0.175 | 0.414 | 0.21 | 0.488 |
| EPS | Not used | 0.139 | 0.207 | 0.126 | 0.193 | 0.125 | 0.216 | 0.165 | 0.253 |
| NaiveLM | Used | 0.771 | 1.117 | 0.889 | 1.388 | 3.818 | 1.03 | 8.83 | 1.407 |

Example 2

FIGS. 7A-7F shows the results of an example that used data obtained from actual DNA mixture samples to illustrate that some implementations can effectively quantify and deconvolve DNA mixture samples. This example shows that some implementations can provide improved signal level for DNA mixture deconvolution. In this example, data were analyzed using a narrow prior.

The samples included DNA from two contributors, various samples having 60%-40%, 75%-25%, 90%-10%, and 95%-5% fractions for the two contributors. The samples included 3 replicates each of subjects NA12878 and NA18507.

Figure 7A:
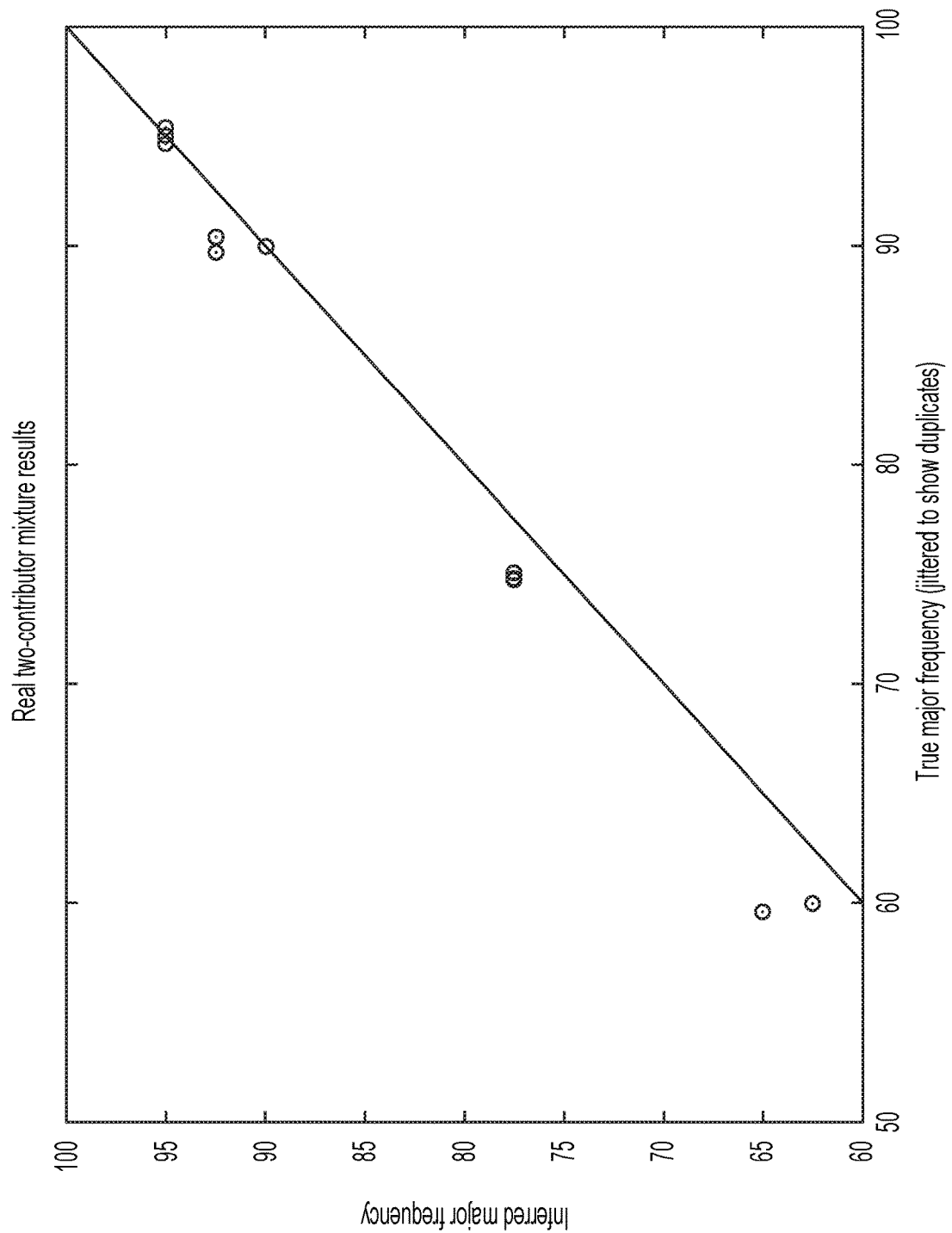
FIGS. 7A-7F shows the results of an example that used data obtained from actual DNA mixture samples to illustrate that some implementations can effectively quantify and deconvolve DNA mixture samples.

FIG. 7A shows the major contributor fraction (or referred to as "major frequency" in the figure) quantified by some implementations. The horizontal axis shows the actual contributor frequency of the major contributor. The vertical axis shows the major contributor fraction inferred (to the nearest 2.5%) by the probabilistic mixture model. The data demonstrate that the probabilistic mixture model provides predictions that are very close to the true fractions, as indicated by the data points positioned near the identity line.

Figure 7B:
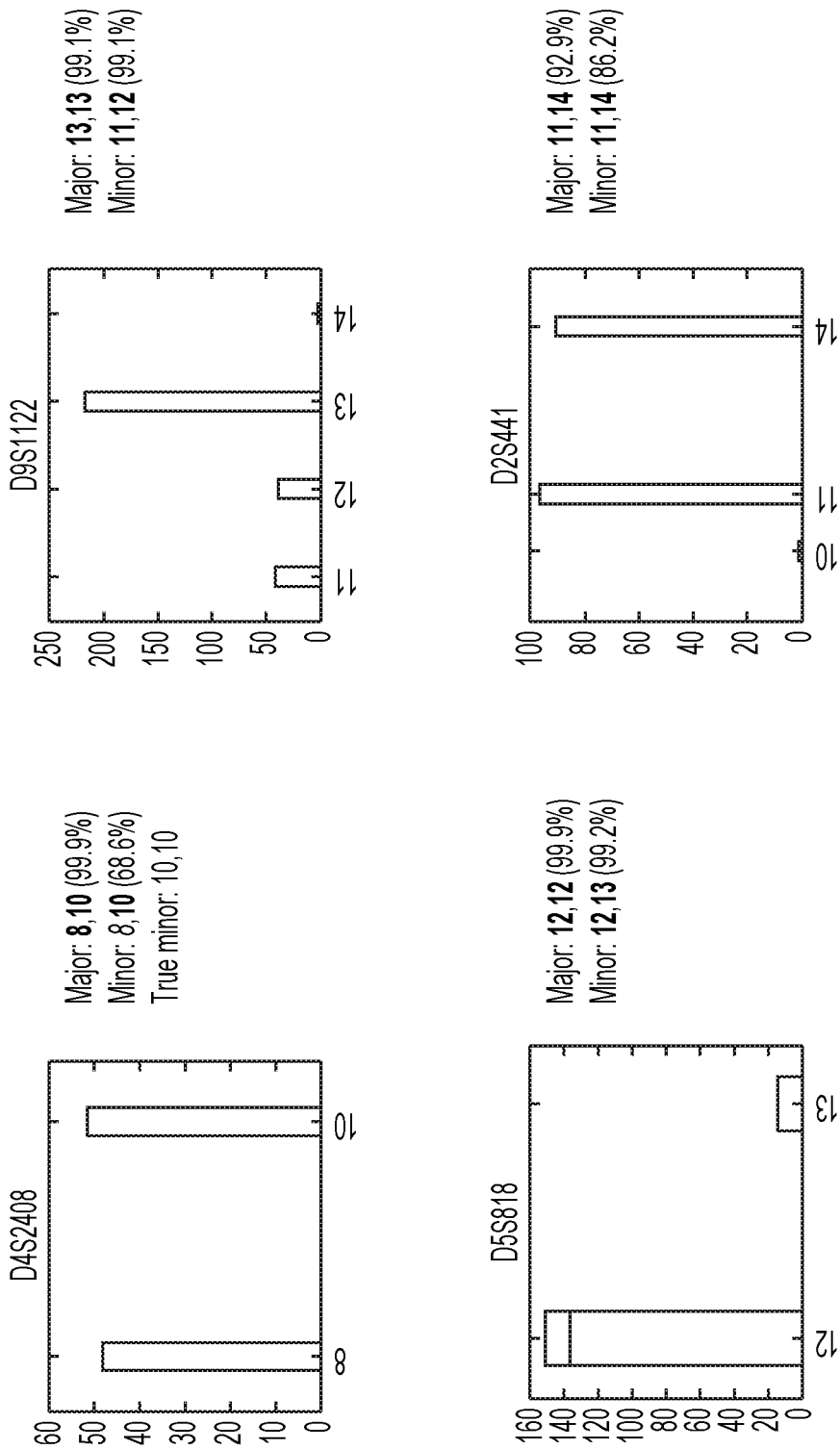

FIG. 7B shows the genotype for the major contributor and the minor contributor as predicted by the probabilistic mixture model for four different alleles in four subplots. The two subplots on the left show results obtained from a sample of 75-25 contributor fractions. The two subplots on the right show results obtained from a mixture sample of 60-40 fractions. The horizontal axis indicates the labels for the different alleles at a locus. The vertical axis shows the allele counts for a locus. All genotypes predicted by the model were correct except for one allele of the minor contributor at locus D4S2408 shown in the upper left subplot. At that locus, the true minor contributor's genotype is (10, 10), but the model predicted it as (8, 10). Interestingly, the confidence level of the prediction for this locus for the minor contributor is at a relatively low level of 68.6%. In this example, it is possible to remove the erroneous prediction by setting a call criterion to be above 70%.

Figure 7C:
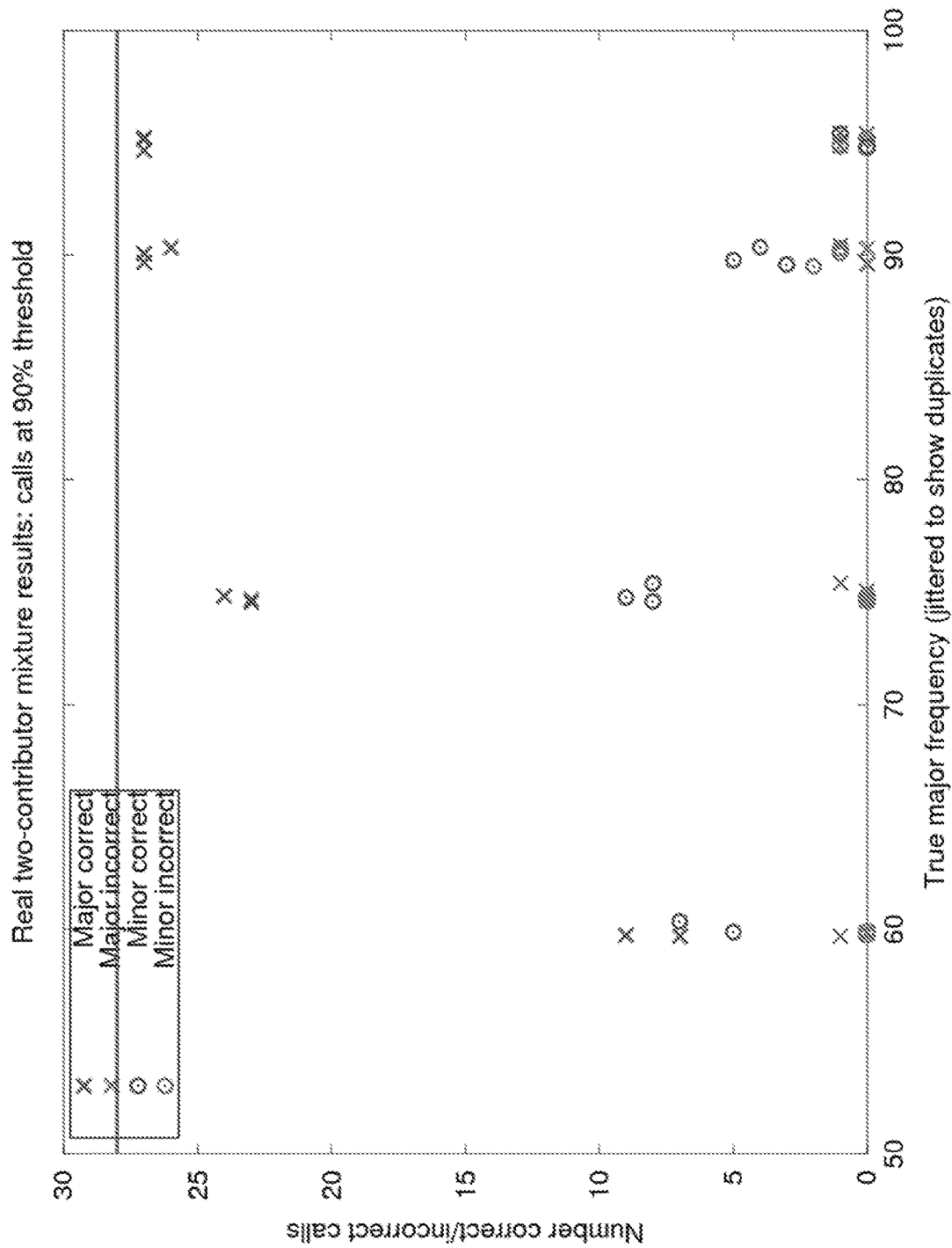

FIG. 7C shows the number of correct and incorrect calls of the contributors' genotypes. The horizontal axis shows the actual contributor fraction for the major contributor (labeled as "major frequency" in the figure). The vertical axis shows the number of correct and incorrect calls. The "x" signs show the data for the major contributor, and the circle signs show the data for the minor contributor. The black symbols show the correct calls, while the gray symbols show the data for the incorrect calls. The horizontal line at 28 indicates the theoretical maximum correct calls. FIG. 7C shows data for calls made at a threshold value of 90% confidence. The data of FIG. 7C shows that the correct numbers of calls are relatively high across the different contributor fractions, while the incorrect calls are relatively low and consistently below five. FIG. 7C also shows that as the contributor fraction goes up from 60% to 95%, the correct calls for the major contributor increased and approached the theoretical maximum level.

Figure 7D:
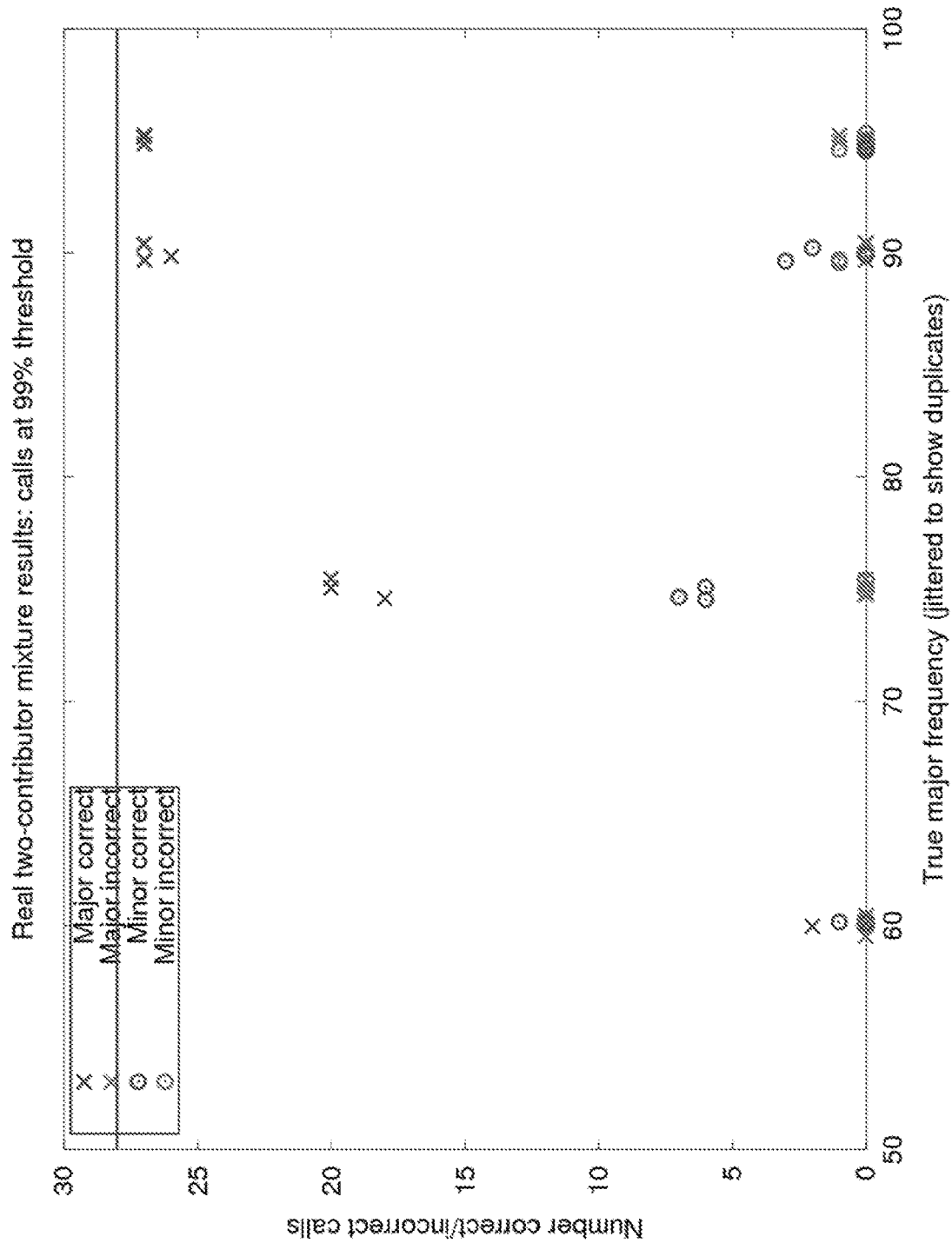

FIG. 7D shows correct and incorrect calls using the same data but a higher call criterion at 99%. Again, the numbers of correct calls are consistently high across the different major contributor fractions and the incorrect call numbers are relatively low and consistently below five. Because the call criterion in FIG. 7D is higher than the criterion FIG. 7C, both the correct calls and incorrect calls have lower numbers. However, the correct calls for the major contributor at 90% and 95% fractions remained high and near the theoretical maximal value.

Figure 7E:
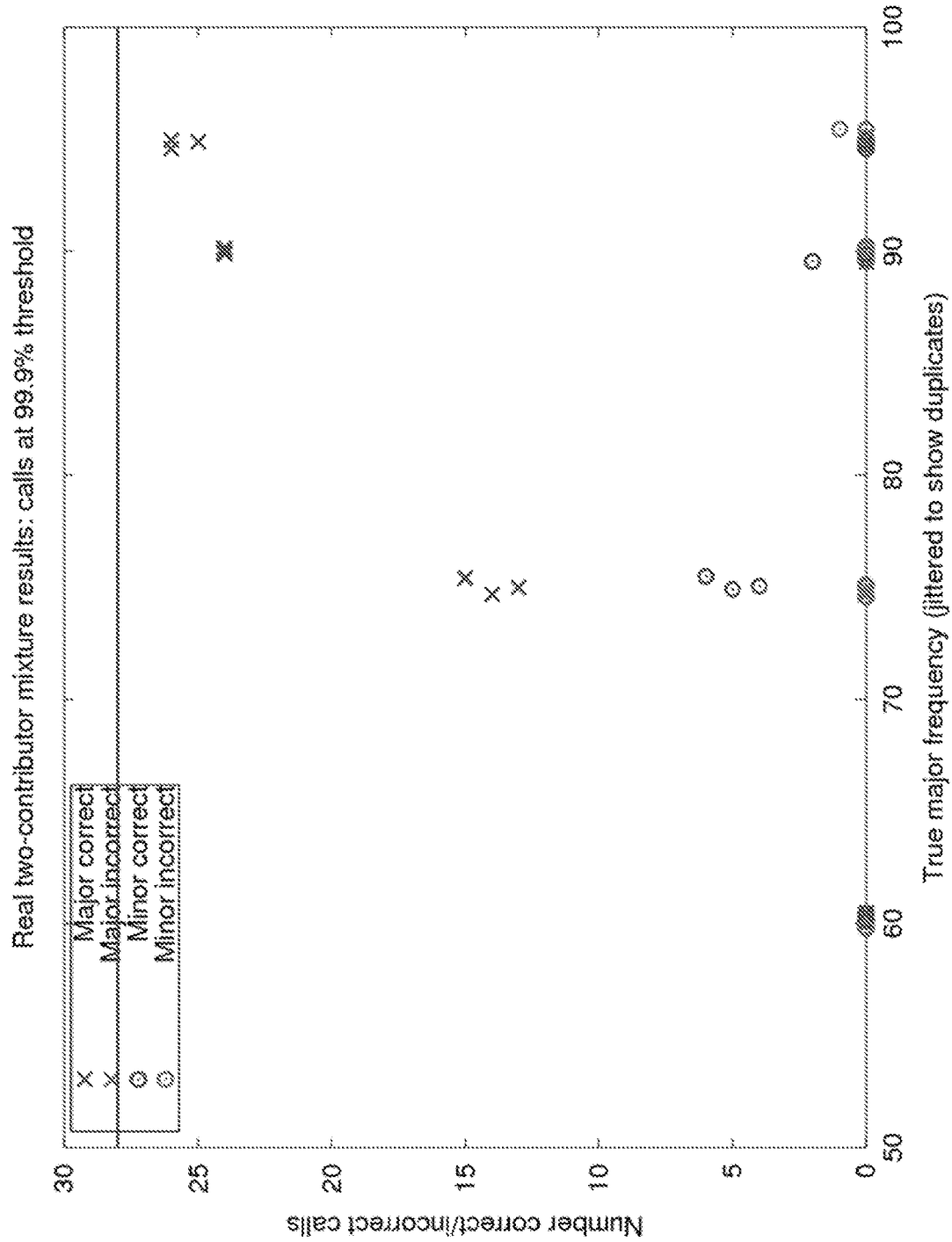

FIG. 7E shows data that are similar to FIGS. 7C and 7D, except that the call criterion was increased to 99.9%. Due to the even higher call threshold value, the number of correct and incorrect calls are slightly lower than results of FIG. 7D. Importantly, there are no incorrect calls at this level of confidence, except at three loci that are known to deviate from model assumptions for known reasons. These loci can be avoided in analysis. Apart from these cases, the model never ascribes high confidence to incorrect calls. So it is quantifying the uncertainty in the genotype calls appropriately.

The results from FIGS. 7C-7E show that the probabilistic mixture model can accurately determine genotypes of contributors. Based on different needs in different applications, different call criterion values may be adopted to achieve the desirable sensitivity and selectivity.

Figure 7F:
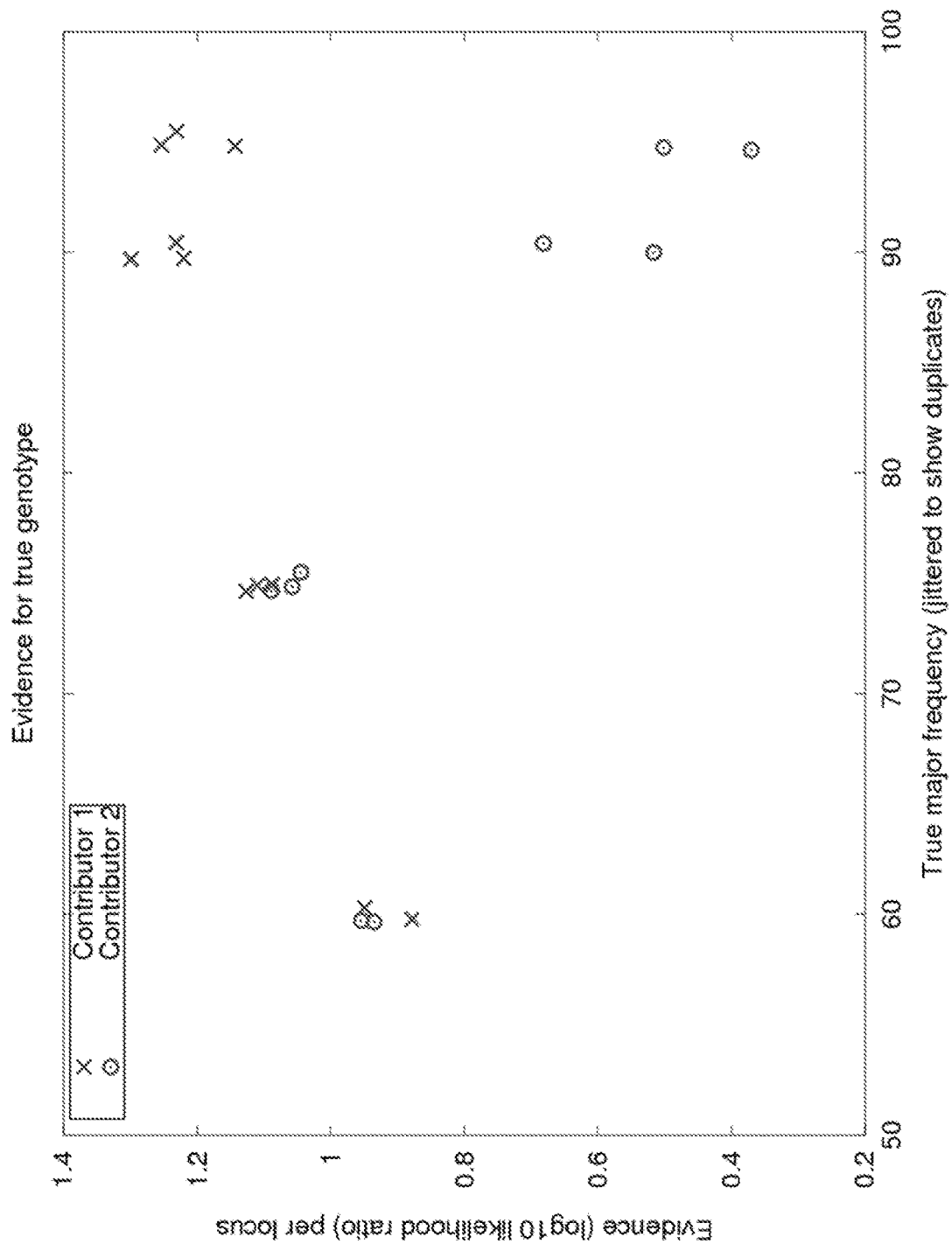

FIG. 7F shows the number of correct and incorrect calls regarding whether a known contributor's DNA is included in the DNA mixture sample. The horizontal axis shows the actual contributor fraction for the major contributor (labeled as "true major frequency"). The vertical axis shows the evidence value per locus that the sample includes the genotype. The "x" signs show the data for the major contributor, and the circle signs show the data for the minor contributor. The data of FIG. 7F shows that there were relatively high levels of evidence that the sample included the two contributors. Not surprisingly, the evidence level was relatively low for the minor contributor when the major contributor's fractions were at 90% and 95%.

Example 3

FIGS. 8A-8D shows the results of an example that used simulated data to illustrate that some implementations can effectively quantify and deconvolve DNA mixture samples. This example shows that some implementations can provide improved signal level for DNA mixture deconvolution.

The simulations have four different designs: Easy 2-contributor (80-20); Difficult 2-contributor (55-45); Easy 3-contributor (60-30-10); and Difficult 3-contributor (50-30-20). The easy designs have the contributor fractions that are further apart than the difficult designs.

The simulations include data for 50 loci and 6 alleles. Allele balance depends on: number of molecules in original sample (fixed: 6000), average molecule detection rate (fixed at 10%; i.e. 600 molecules detected a locus on average), allele-to-allele variation of molecule detection rate (varies over a range), and sampling noise. The stutter rates were simulated as 1% or 2%, and the dropout rate is 1%. The results were obtained assuming a broad prior.

For the easy 3-contributor (60-30-10) mixture samples, all contributor frequencies were inferred within 2.5% of the true values. For the difficult 3-contributor (50-30-20) mixture samples, all contributor frequencies were inferred within 7.5% of the true values.

Figure 8A:
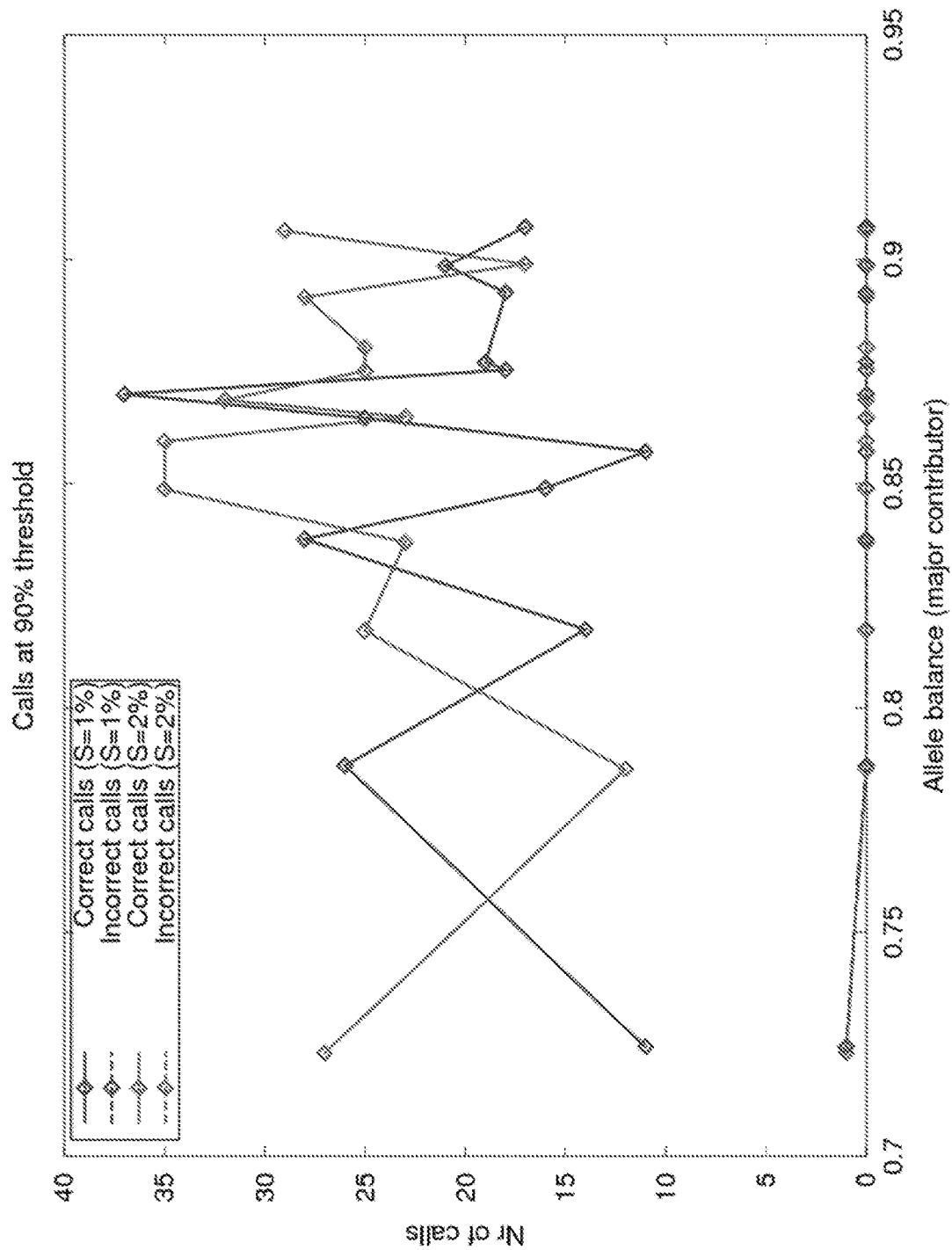
FIGS. 8A-8D shows the results of an example that used simulated data to illustrate that some implementations can effectively quantify and deconvolve DNA mixture samples.

FIGS. 8A-8D show data for the easy 3-contributor (60-30-10) mixture samples. FIG. 8A shows the number of correct and incorrect calls of the contributors' genotypes. The horizontal axis shows the allele balance for the major contributor. The vertical axis shows the number of correct and incorrect calls. The black symbols show the data for 1% stutter rate, and the gray symbols show the data for 2% stutter rate. The solid lines show the correct calls, while the dashed lines show the data for the incorrect calls. FIG. 8A shows data for calls made at a threshold value of 90% confidence. The data of FIG. 8A shows that the correct numbers of calls are relatively high across the different allele balance values, while the incorrect calls are consistently near zero.

Figure 8B:
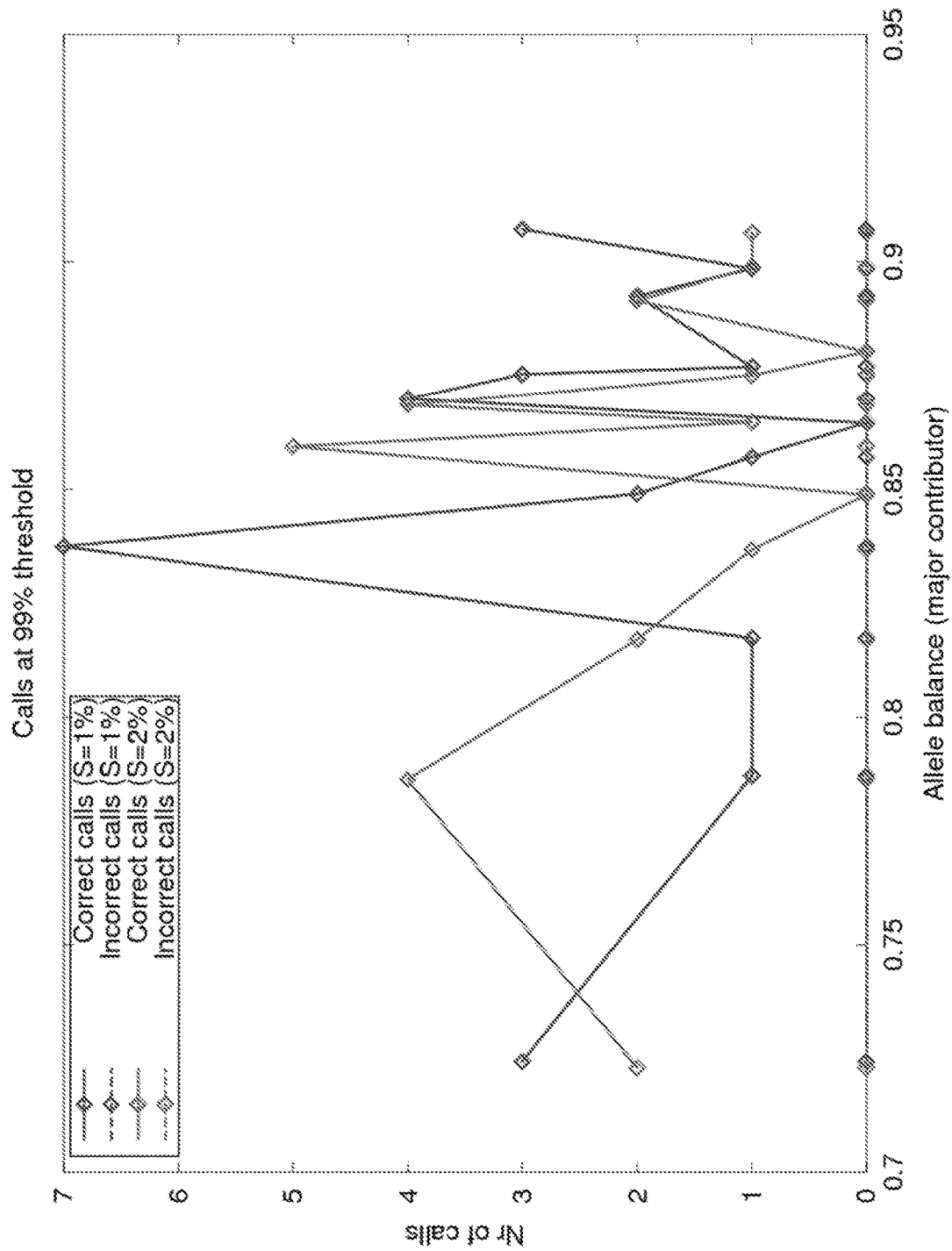
Figure 8C:
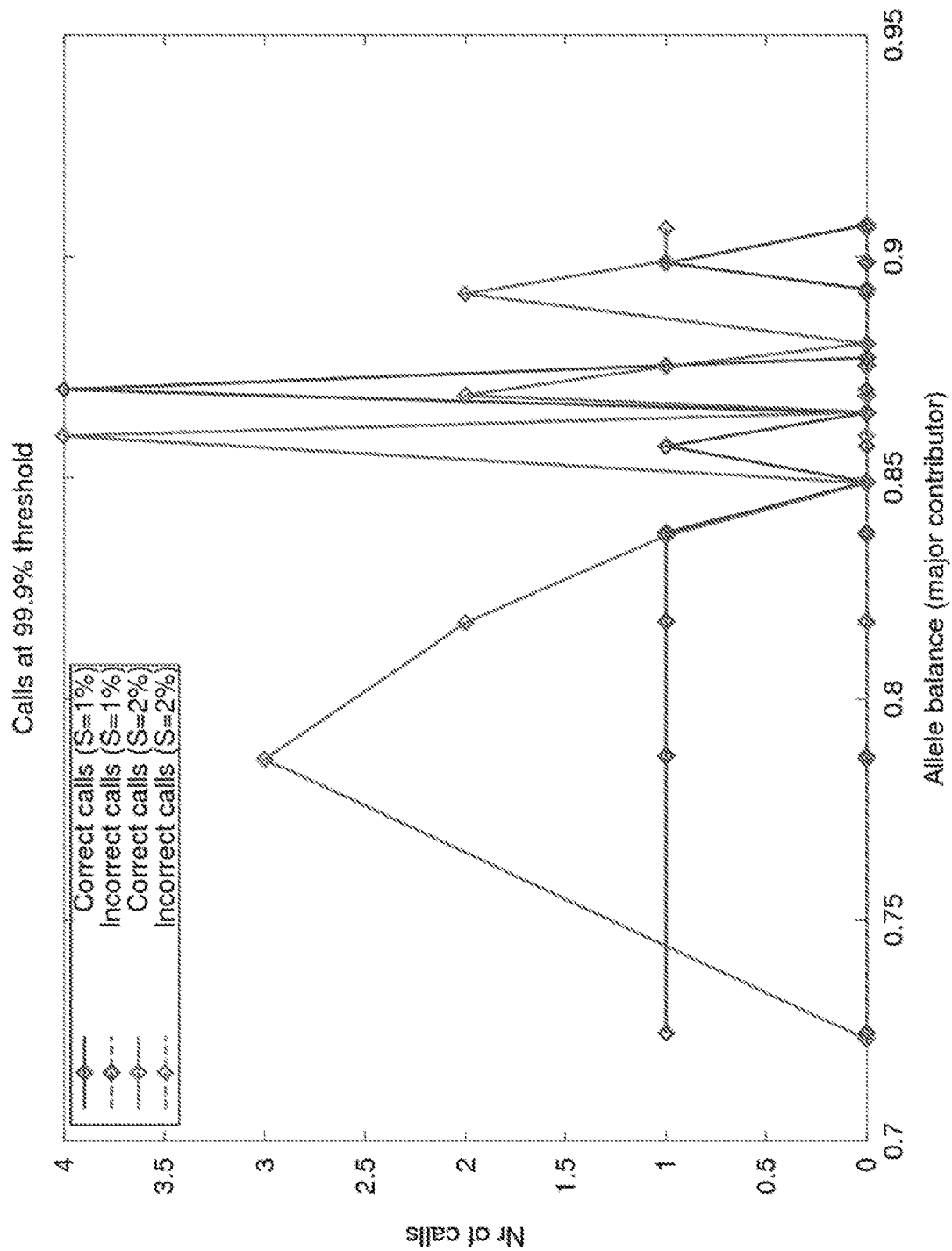

FIG. 8B shows correct and incorrect calls using the same data as FIG. 8A but a higher call criterion at 99%. The numbers of correct calls are significantly lower than those in FIG. 8A, while the incorrect calls are bottomed out, indicating that the threshold value at 99% may be too stringent in this application. FIG. 8C shows data that are similar to FIGS. 8A and 8B, except that the call criterion was increased to 99.9%. Due to the even higher call threshold value, the number of correct calls are further decreased. The results from FIGS. 3A-3C show that the probabilistic mixture model can accurately determine genotypes of contributors, and the suitable threshold values in this example can be set near 90% or less than 99%.

Figure 8D:
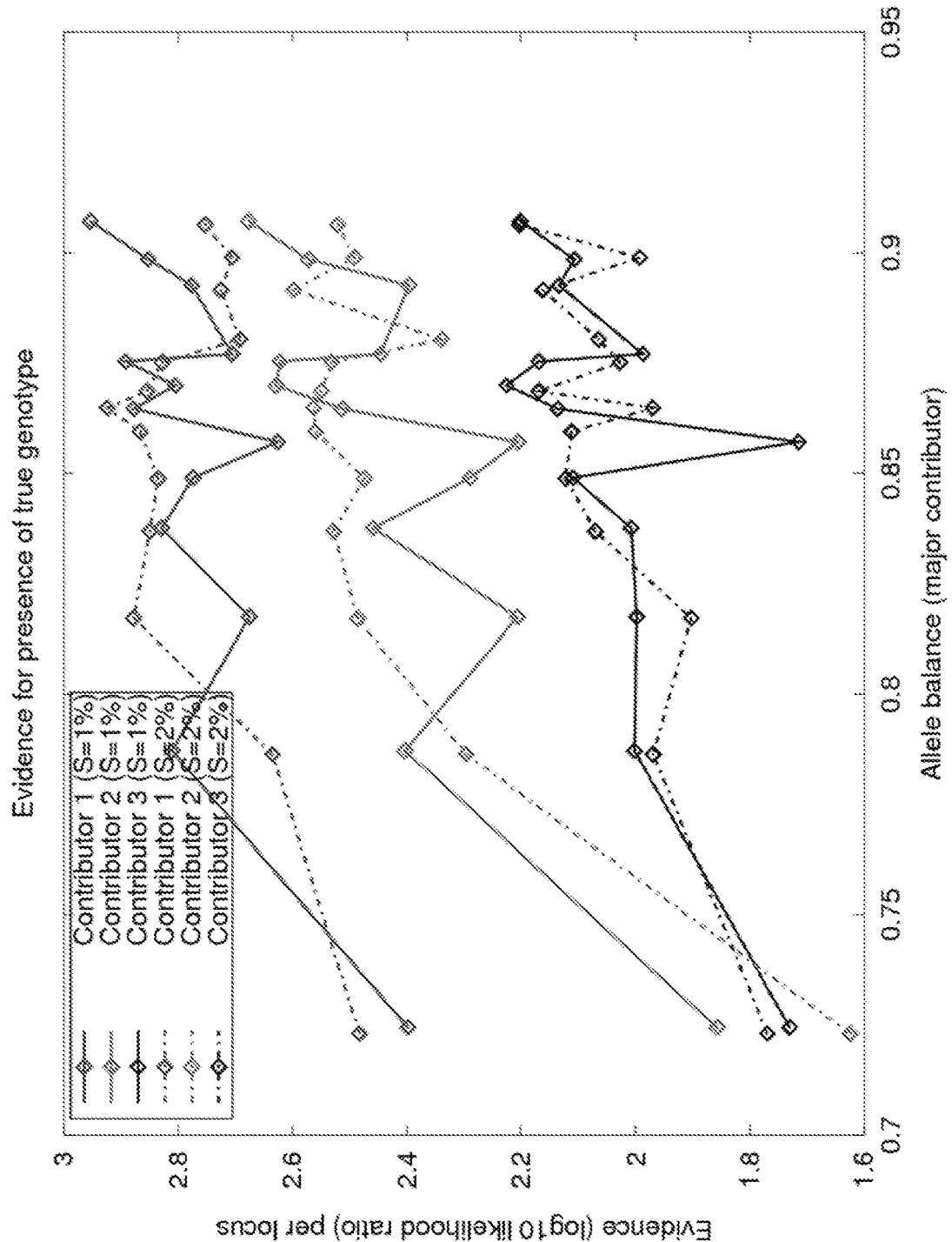

FIG. 8D shows the number of correct and incorrect calls regarding whether one of the three contributors' DNA is included in the DNA mixture sample. The horizontal axis shows the allele balance for the major contributor. The vertical axis shows the evidence value per locus that the sample includes the genotype. The solid lines show the data for 1% stutter error, and the dashed lines show the data for 2% stutter error. Three different shades of gray show data for the three different contributors. The data of FIG. 8D shows that there were relatively high levels of evidence that the sample included the three contributors for both stutter error conditions.

What is claimed is:

1. A method, implemented at a computer system that includes one or more processors and system memory, of quantifying a nucleic acid sample comprising tumor DNA and non-tumor DNA from a cell-free DNA (cfDNA) sample of an individual, the method comprising:

(a) mapping nucleic acid sequence reads generated from the nucleic acid sample to one or more alleles at one or more polymorphism loci on a reference sequence so as to identify reads among the nucleic acid sequence reads matching any sequence of a plurality of unbiased target sequences (b) determining, using the nucleic acid sequence reads, allele counts for each of the one or more alleles at the one or more polymorphism loci;

(c) applying a probabilistic mixture model to the allele counts, wherein the probabilistic mixture model uses probability distributions to model the allele counts at the one or more polymorphism loci, the probability distributions comprising a first probability distribution accounting for errors in the nucleic acid sequence reads, a second probability distribution accounting for nucleic acid extraction errors, and a third probability distribution accounting for nucleic acid amplification errors and wherein the probabilistic mixture model quantifies fractions of nucleic acid of one or both of the tumor DNA or non-tumor DNA in the nucleic acid sample using a likelihood function comprising a product of likelihoods of non-stutter allele counts and likelihoods of stutter allele counts, and wherein the probabilistic mixture model prunes genotype configurations from data to be used to quantify the fractions of nucleic acid of the tumor DNA and non-tumor DNA in the nucleic acid sample, wherein pruning genotype configurations comprises limiting genotype configurations that are plausible by constructing a list of required alleles, wherein the list of required alleles consists essentially of alleles having allele counts above a threshold and too high to be plausible due to stutter drop-in, wherein the threshold is a sum of (i) a maximum non-stutter allele count, and (ii) a value multiplied by a count of potential stutter donor alleles;

(d) quantifying, using the probabilistic mixture model, a tumor DNA fraction in the nucleic acid sample; and (e) determining a posterior probability that one or both of the tumor DNA fraction or a non-tumor DNA fraction has a specific genotype at the one or more polymorphism loci by performing steps comprising:

(i) multiplying prior probabilities of genotype configurations by likelihoods of the genotype configurations, wherein the prior probabilities are based on population data of allele frequencies of the genotype configurations;

(ii) normalizing a product of (i) by a sum over genotype space, wherein the genotype space is based on possible genotypes as a function of a relationship between the tumor DNA and non-tumor DNA; and (iii) summing over genotype configurations containing the specific genotype to obtain the posterior probability; and (f) developing and executing a plan for treatment of the individual based on the tumor DNA fraction in the nucleic acid sample from step (d) and the posterior probability of step (e), wherein executing the plan comprises administering a cancer treatment comprising one or more of surgically removing neoplastic cells from the individual, performing radiotherapy or causing radiotherapy to be performed on the individual, or administering or causing to be administered an anti-cancer drug to the individual.

2. The method of claim 1, wherein the probability distributions comprise a first binomial distribution expressed as follows:

$$n_{ij} \sim BN(n_i, p_{ij})$$

wherein
$n_{ij}$ is an allele count for allele j at locus I;
$n_i$ is a total allele count at locus I; and
$p_{ij}$ is a probability parameter indicating the probability of allele j at locus i.

3. The method of claim 2, wherein the probability parameter $p_{ij}$ is a function of one or more of:
(i) a fraction of nucleic acid of one of the tumor DNA or the non-tumor DNA in the nucleic acid sample, or β;
(ii) genotypes of the tumor DNA or non-tumor DNA, or G; or
(iii) errors in the nucleic acid sequence reads, or θ.

4. The method of claim 3, wherein the probabilistic mixture model uses a beta distribution to model the errors in the nucleic acid sequence reads, wherein the beta distribution is defined by a mean parameter, μ, and a concentration parameter, k having a prior representing different noise conditions.

5. The method of claim 4, wherein the probabilistic mixture model uses a combined first binomial distribution and the beta distribution to obtain a marginal distribution of $n_{ij}$ that follows a beta-binomial distribution to generate a combined error model that models the errors in the nucleic acid sequence reads and errors in DNA extraction of the nucleic acid sample.

6. The method of claim 5, wherein the beta-binomial distribution has the form:

$$BB(n_{ij}|n_i, \mu, k).$$

7. The method of claim 2, wherein the probabilistic mixture model uses a second binomial distribution to model stutter errors in the allele counts.

8. The method of claim 7, wherein the second binomial distribution is expressed as follows:

$$s_{ik} \sim BN(n_{i(k=1)}, r_i)$$

wherein
$s_{ik}$ is a stutter allele count at locus I of a stutter allele that appears to be allele k but actually results from a stutter error of allele k+1;
$n_{i(k+1)}$ is an original allele count of allele k+1 at locus I; and
$r_i$ is a stutter rate for locus i.

9. The method of claim 8, wherein the stutter rate r varies across loci and has a prior representing different noise conditions, the prior being shared across loci.

10. The method of claim 8, wherein the probabilistic mixture model adds a fixed number of molecules to an allele count assigned to allele k+1 when determining a number of molecules from which stutter can potentially originate.

11. The method of claim 1, wherein (c) comprises:
calculating a plurality of likelihood values using a plurality of potential fraction values and a likelihood function of the allele counts determined in (b);
identifying a potential fraction vector associated with a maximum likelihood value; and
quantifying the one or more fractions of nucleic acid of the tumor DNA or non-tumor DNA in the nucleic acid sample using the identified potential fraction vector, wherein the likelihood function depends on P(G|π), which is a prior probability of the genotype of one or both of the tumor DNA or non-tumor DNA given a population allele frequency (π).

12. The method of claim 11, wherein the prior probability P(G|π) is calculated using marginal distributions that satisfy the Hardy-Weinberg equilibrium or calculated considering a dummy allele with a fixed prior probability representing mechanistic drop-out.

13. The method of claim 1, wherein the probabilistic mixture model uses a dummy out-of-sample allele to model natural drop-out.

14. The method of claim 13, wherein the number of unobserved alleles is estimated by:
interpolating all integers between the shortest and longest observed integer-valued alleles, adding any observed non-integer-valued alleles, and
returning the maximum of the resulting value and a threshold value.

15. The method of claim 1, wherein pruning genotype configurations comprises: removing genotype configurations that have poor matches between the allele counts and expected allele counts.

16. The method of claim 1, wherein the probability distributions further comprise a probability distribution accounting for nucleic acid extraction errors and a probability distribution accounting for nucleic acid amplification errors.

17. The method of claim 1, wherein the plurality of unbiased target sequences comprise: a reference target sequence that is a sub-sequence of the reference sequence, the reference target sequence having a reference allele with a reference nucleotide at a polymorphic site; alternative target sequences each having an alternative allele with an alternative nucleotide at the polymorphic site; mutated reference target sequences comprising possible sequences that each differ from the reference target sequence by only one nucleotide at a site that is not the polymorphic site; mutated alternative target sequences comprising possible sequences that each differ from one or more of the alternative target sequences by only one nucleotide at a site that is not the polymorphic site; and one or more unexpected allele target sequences each having an unexpected allele different from the reference allele and the alternative allele.

18. The method of claim 1, wherein executing the plan further comprises conducting further cancer testing on the individual.

19. The method of claim 1, wherein executing the plan further comprises further monitoring the individual for cancer.

20. A computer system comprising system memory and one or more processors configured to:
(a) map nucleic acid sequence reads generated from a nucleic acid sample to one or more alleles at one or more polymorphism loci on a reference sequence so as to identify reads among the nucleic acid sequence reads matching any sequence of a plurality of unbiased target sequences, wherein the nucleic acid sample comprises tumor DNA and non-tumor DNA from a cell-free DNA (cfDNA) sample of an individual;
(b) determine, using the nucleic acid sequence reads, allele counts for each of the one or more alleles at the one or more polymorphism loci;
(c) apply a probabilistic mixture model to the allele counts, wherein the probabilistic mixture model uses probability distributions to model the allele counts at the one or more polymorphism loci, the probability distributions comprising a first probability distribution accounting for errors in the nucleic acid sequence reads, a second probability distribution accounting for nucleic acid extraction errors, and a third probability distribution accounting for nucleic acid amplification errors and wherein the probabilistic mixture model quantifies fractions of nucleic acid of one or both of the tumor DNA or non-tumor DNA in the nucleic acid sample using a likelihood function comprising a product of likelihoods of non-stutter allele counts and likelihoods of stutter allele counts, and wherein the probabilistic mixture model prunes genotype configurations from data to be used to quantify the fractions of nucleic acid of the tumor DNA and non-tumor DNA in the nucleic acid sample, wherein pruning genotype configurations comprises limiting genotype configurations that are plausible by constructing a list of required alleles, wherein the list of required alleles consists essentially of alleles having allele counts above a threshold and too high to be plausible due to stutter drop-in, wherein the threshold is a sum of (i) a maximum non-stutter allele count, and (ii) a value multiplied by a count of potential stutter donor alleles;

(d) quantify, using the probabilistic mixture model, a tumor DNA fraction in the nucleic acid sample; and (e) determine a posterior probability that one or both of the tumor DNA fraction or a non-tumor DNA fraction has a specific genotype at the one or more polymorphism loci by performing steps comprising:
  (i) multiplying prior probabilities of genotype configurations by likelihoods of the genotype configurations, wherein the prior probabilities are based on population data of allele frequencies of the genotype configurations;
  (ii) normalizing a product of (i) by a sum over genotype space, wherein the genotype space is based on possible genotypes as a function of a relationship between the tumor DNA and non-tumor DNA; and
  (iii) summing over genotype configurations containing the specific genotype to obtain the posterior probability; and (f) generating and outputting a plan to be executed for treating the individual based on the tumor DNA fraction in the nucleic acid sample from step (d) and the posterior probability of step (e), wherein executing the plan comprises administering a cancer treatment comprising one or more of surgically removing neoplastic cells from the individual, performing radiotherapy or causing radiotherapy to be performed on the individual, or administering or causing to be administered an anti-cancer drug to the individual.

21. The system of claim 20, wherein the one or more processors are further configured to determine an allele configuration at each of the one or more polymorphism loci.

22. A non-transitory computer-readable medium storing program code that, when executed by one or more processors of a computer system, causes the computer system to implement a method of quantifying a nucleic acid sample comprising tumor DNA and non-tumor DNA from a cell-free DNA (cfDNA) sample of an individual, said program code comprising:
  (a) code for mapping nucleic acid sequence reads generated from the nucleic acid sample to one or more alleles at one or more polymorphism loci on a reference sequence so as to identify reads among the nucleic acid sequence reads matching any sequence of a plurality of unbiased target sequences;
  (b) code for determining, using the nucleic acid sequence reads, allele counts for each of the one or more alleles at the one or more polymorphism loci;
  (c) code for applying a probabilistic mixture model to the allele counts, wherein the probabilistic mixture model uses probability distributions to model the allele counts at the one or more polymorphism loci, the probability distributions comprising a first probability distribution accounting for errors in the nucleic acid sequence reads, a second probability distribution accounting for nucleic acid extraction errors, and a third probability distribution accounting for nucleic acid amplification errors and wherein the probabilistic mixture model quantifies fractions of nucleic acid of one or both of the tumor DNA or non-tumor DNA in the nucleic acid sample using a likelihood function comprising a product of likelihoods of non-stutter allele counts and likelihoods of stutter allele counts, and wherein the probabilistic mixture model prunes genotype configurations from data to be used to quantify the fractions of nucleic acid of the tumor DNA and non-tumor DNA in the nucleic acid sample, wherein pruning genotype configurations comprises limiting genotype configurations that are plausible by constructing a list of required alleles, wherein the list of required alleles consists essentially of alleles having allele counts above a threshold and too high to be plausible due to stutter drop-in, wherein the threshold is a sum of (i) a maximum non-stutter allele count, and (ii) a value multiplied by a count of potential stutter donor alleles;
  (d) code for quantifying, using the probabilistic mixture model, a tumor DNA fraction in the nucleic acid sample; and
  (e) code for determining a probability that one or both of the tumor DNA fraction or a non-tumor DNA fraction has a specific genotype at the one or more polymorphism loci by performing steps comprising:
    (i) multiplying prior probabilities of genotype configurations by likelihoods of the genotype configurations, wherein the prior probabilities are based on population data of allele frequencies of the genotype configurations;
    (ii) normalizing a product of (i) by a sum over genotype space, wherein the genotype space is based on possible genotypes as a function of a relationship between the tumor DNA and non-tumor DNA; and
    (iii) summing over genotype configurations containing the specific genotype to obtain the posterior probability; and
  (f) code for generating and outputting a plan to be executed for treating the individual based on the tumor DNA fraction in the nucleic acid sample from step (d) and the posterior probability of step (e), wherein executing the plan comprises administering a cancer treatment comprising one or more of surgically removing neoplastic cells from the individual, performing radiotherapy or causing radiotherapy to be performed on the individual, or administering or causing to be administered an anti-cancer drug to the individual.

* * * * *

UNITED STATES PATENT AND TRADEMARK OFFICE
CERTIFICATE OF CORRECTION

PATENT NO. : 11,990,208 B2
APPLICATION NO. : 16/622814
DATED : May 21, 2024
INVENTOR(S) : Konrad Scheffler, Johann Felix Wilhelm Schlesinger and Ryan Matthew Kelley It is certified that error appears in the above-identified patent and that said Letters Patent is hereby corrected as shown below:

In the Claims

1. In Column 64, Line 6, Claim 1, replace "sequences" with --sequences;--.

2. In Column 65, Line 41 (Approx.), Claim 26, replace "$s_{ik} \sim BN(n_{(i(k=1))}, r_i)$" with --$s_{ik} \sim BN(n_{i(k+1)}, r_i)$--.

Signed and Sealed this
Twenty-ninth Day of October, 2024

Katherine Kelly Vidal
*Director of the United States Patent and Trademark Office*